US012342240B2

(12) United States Patent
Williams

(10) Patent No.: US 12,342,240 B2
(45) Date of Patent: *Jun. 24, 2025

(54) SYSTEMS AND METHODS FOR MONITORING FOR AND LOWERING THE RISK OF ADDICTION-RELATED OR RESTRICTION VIOLATION-RELATED BEHAVIOR(S)

(71) Applicant: Conquer Your Addiction LLC, Kirkwood, MO (US)

(72) Inventor: David H. Williams, Kirkwood, MO (US)

(73) Assignee: Conquer Your Addiction LLC, Kirkwood, MO (US)

(*) Notice: Subject to any disclaimer, the term of this patent is extended or adjusted under 35 U.S.C. 154(b) by 336 days.

This patent is subject to a terminal disclaimer.

(21) Appl. No.: 17/861,559

(22) Filed: Jul. 11, 2022

(65) Prior Publication Data

US 2022/0353632 A1 Nov. 3, 2022

Related U.S. Application Data

(63) Continuation-in-part of application No. 16/700,601, filed on Dec. 2, 2019, now Pat. No. 11,388,546, (Continued)

(51) Int. Cl.
*H04L 9/00* (2022.01)
*A61B 5/00* (2006.01)
(Continued)

(52) U.S. Cl.
CPC .......... *H04W 4/021* (2013.01); *A61B 5/0022* (2013.01); *A61B 5/4842* (2013.01);
(Continued)

(58) Field of Classification Search
CPC ...................................................... H04W 4/021
(Continued)

(56) References Cited

U.S. PATENT DOCUMENTS 5,601,598 A  2/1997 Fisher
5,980,447 A  11/1999 Trudeau
(Continued)

FOREIGN PATENT DOCUMENTS

JP  5867847 B2  2/2016
JP  5877528 B2  3/2016
(Continued)

OTHER PUBLICATIONS

Ayyar, Ranjani, One Heart on YuppTV, Chennai girl makes it to Forbes list with tool to combat addictions, https://timesofindia.indiatimes/city/chennai/chennai-girl-makes-it-to-forbes-list-with . . . , Nov. 16, 2017, 42 pages.
(Continued)

*Primary Examiner* — Christopher J Brown
(74) *Attorney, Agent, or Firm* — Harness, Dickey & Pierce, P.L.C.; Anthony G. Fussner

(57) ABSTRACT

Exemplary embodiments are disclosed of systems and methods for monitoring for and lowering the risk of addiction-related or restriction violation-related behavior(s).

41 Claims, 36 Drawing Sheets

Related U.S. Application Data which is a continuation of application No. 15/840,775, filed on Dec. 13, 2017, now Pat. No. 10,555,112.

(60) Provisional application No. 62/480,206, filed on Mar. 31, 2017, provisional application No. 62/435,042, filed on Dec. 15, 2016.

(51) Int. Cl.

| | | |
|---|---|---|
| *A63F 9/12* | (2006.01) | |
| *G06F 21/36* | (2013.01) | |
| *G06Q 10/0635* | (2023.01) | |
| *G06Q 20/32* | (2012.01) | |
| *G06Q 20/40* | (2012.01) | |
| *G07F 17/32* | (2006.01) | |
| *G16H 40/67* | (2018.01) | |
| *G16H 50/30* | (2018.01) | |
| *H04L 9/40* | (2022.01) | |
| *H04L 67/12* | (2022.01) | |
| *H04W 4/021* | (2018.01) | |
| *H04W 4/029* | (2018.01) | |
| *H04W 12/08* | (2021.01) | |
| *H04W 12/06* | (2021.01) | |

(52) U.S. Cl.
CPC .......... *A61B 5/6802* (2013.01); *A61B 5/7264* (2013.01); *A61B 5/747* (2013.01); *A63F 9/12* (2013.01); *G06F 21/36* (2013.01); *G06Q 10/0635* (2013.01); *G06Q 20/3224* (2013.01); *G06Q 20/401* (2013.01); *G06Q 20/4014* (2013.01); *G06Q 20/4016* (2013.01); *G07F 17/3237* (2013.01); *G16H 40/67* (2018.01); *G16H 50/30* (2018.01); *H04L 63/107* (2013.01); *H04L 63/20* (2013.01); *H04L 67/12* (2013.01); *H04W 4/029* (2018.02); *H04W 12/08* (2013.01); *G06F 2221/2111* (2013.01); *H04W 12/06* (2013.01)

(58) Field of Classification Search
USPC .......................................................... 726/7
See application file for complete search history.

(56) References Cited

U.S. PATENT DOCUMENTS

| | | |
|---|---|---|
| 6,425,764 B1 | 7/2002 | Lamson |
| 6,437,696 B1 | 8/2002 | Lemelson et al. |
| 6,639,516 B1 | 10/2003 | Copley |
| 7,219,368 B2 | 5/2007 | Juels et al. |
| 7,343,365 B2 | 3/2008 | Farnham et al. |
| 7,633,076 B2 | 12/2009 | Huppi et al. |
| 7,908,645 B2 | 3/2011 | Varghese et al. |
| 8,798,593 B2 | 8/2014 | Haney |
| 8,862,393 B2 | 10/2014 | Zhou et al. |
| 9,017,078 B2 | 4/2015 | Gross |
| 9,104,788 B2 | 8/2015 | Friedman et al. |
| 9,288,196 B2 | 3/2016 | Shuster |
| 9,341,050 B2 | 5/2016 | Al-Buraik |
| 9,917,824 B2 | 3/2018 | Britt |
| 10,114,351 B2 | 10/2018 | Fadell et al. |
| 10,218,844 B1 | 2/2019 | Edwards et al. |
| 10,395,221 B1 | 8/2019 | Price et al. |
| 10,477,342 B2 | 11/2019 | Williams |
| 10,497,242 B2 | 12/2019 | Williams |
| 10,555,112 B2 | 2/2020 | Williams |
| 11,388,546 B2 | 7/2022 | Williams |
| 11,599,953 B1 | 3/2023 | McNair |
| 2005/0068169 A1 | 3/2005 | Copley et al. |
| 2006/0004680 A1 | 1/2006 | Robarts et al. |
| 2008/0146193 A1 | 6/2008 | Bentley et al. |
| 2009/0265326 A1 | 10/2009 | Lehrman et al. |
| 2010/0076968 A1 | 3/2010 | Boyns et al. |
| 2010/0125563 A1 | 5/2010 | Nair et al. |
| 2010/0227629 A1 | 9/2010 | Cook et al. |
| 2011/0022540 A1 | 1/2011 | Stern et al. |
| 2012/0083911 A1 | 4/2012 | Louboutin et al. |
| 2012/0135756 A1 | 5/2012 | Rosso et al. |
| 2012/0268269 A1 | 10/2012 | Doyle |
| 2013/0144470 A1* | 6/2013 | Ricci ....................... G06F 16/29 701/2 |
| 2013/0145441 A1 | 6/2013 | Mujumdar et al. |
| 2013/0216989 A1* | 8/2013 | Cuthbert ............... A61B 5/1113 434/238 |
| 2014/0094192 A1 | 4/2014 | Annett |
| 2014/0142729 A1 | 5/2014 | Lobb et al. |
| 2014/0192325 A1 | 7/2014 | Klin et al. |
| 2014/0248904 A1 | 9/2014 | Meredith et al. |
| 2014/0278212 A1 | 9/2014 | Torgersrud et al. |
| 2014/0322676 A1 | 10/2014 | Raman |
| 2014/0331278 A1 | 11/2014 | Tkachev |
| 2014/0347265 A1 | 11/2014 | Aimone et al. |
| 2015/0009028 A1 | 1/2015 | Gehrke et al. |
| 2015/0065822 A1 | 3/2015 | Blenkush |
| 2015/0230086 A1 | 8/2015 | Bentley et al. |
| 2015/0367230 A1 | 12/2015 | Bradford et al. |
| 2016/0019382 A1 | 1/2016 | Chan et al. |
| 2016/0063532 A1 | 3/2016 | Loeb et al. |
| 2016/0063874 A1* | 3/2016 | Czerwinski ............ G16H 50/20 434/236 |
| 2016/0066864 A1 | 3/2016 | Frieder et al. |
| 2016/0070245 A1* | 3/2016 | Lee ....................... A61B 5/0004 700/49 |
| 2016/0078781 A1 | 3/2016 | McCartney |
| 2016/0140353 A1 | 5/2016 | Biswas et al. |
| 2016/0140404 A1 | 5/2016 | Rosen |
| 2016/0260135 A1 | 9/2016 | Zomet et al. |
| 2016/0330601 A1 | 11/2016 | Srivastava |
| 2016/0381502 A1 | 12/2016 | Kern, Jr. et al. |
| 2017/0020442 A1 | 1/2017 | Flitsch et al. |
| 2017/0134832 A1 | 5/2017 | Briggs et al. |
| 2017/0221336 A1* | 8/2017 | Ogaz ....................... G10L 17/00 |
| 2017/0276489 A1 | 9/2017 | Breed |
| 2017/0365182 A1* | 12/2017 | Lavi ................... G09B 19/0092 |
| 2018/0103341 A1 | 4/2018 | Moiyallah, Jr. et al. |
| 2018/0140241 A1 | 5/2018 | Hamalainen et al. |
| 2018/0165476 A1 | 6/2018 | Carey et al. |
| 2018/0166176 A1 | 6/2018 | Flippen et al. |
| 2018/0173866 A1 | 6/2018 | Williams |
| 2018/0176727 A1 | 6/2018 | Williams |
| 2018/0240544 A1 | 8/2018 | Lo et al. |
| 2019/0101985 A1 | 4/2019 | Sajda et al. |
| 2019/0122258 A1 | 4/2019 | Bramberger et al. |
| 2020/0160223 A1 | 5/2020 | McGavran et al. |

FOREIGN PATENT DOCUMENTS

| | | |
|---|---|---|
| KR | 100692803 B1 | 3/2007 |
| KR | 101581772 B1 | 1/2016 |
| KR | 1020160046690 A | 4/2016 |
| WO | WO-2015171702 A1 | 11/2015 |
| WO | WO-2018112047 A2 | 6/2018 |
| WO | WO-2018112048 A1 | 6/2018 |

OTHER PUBLICATIONS

Campbell, Discovering addiction: The science and politics of substance abuse research, 2007, Abstract, 2 pages.

Carise et al., Development a National Addiction Treatment Information System: An Introduction to the Drug Evaluation Network System; Journal of Substance Abuse Treatment; 1999; Abstract; 2 pages.

Cartreine, PhD., et al., A Roadmap to Computer-Based Psychotherapy in the United States, Copyright 2010 President and Fellows of Harvard College; 16 pages.

Conquer Your Alcoholism, conqueryouraddiction.com, accessed Dec. 7, 2017 3 pages.

(56) References Cited

OTHER PUBLICATIONS

D. H. Williams, How to Conquer Your Alcoholism—Made Simple! The Practical Way to Get and Stay Sober; paperback—Aug. 3, 2017; 259 pages; 1 page attached.

D. H. Williams, How to Conquer your Alcoholism: A Complete and Useable Program and Reference Guide to Getting & Staying Sober; Jan. 16, 2015; 654 pages; (1 page attached).

Dackis, et al., Neurobiology of addiction: treatment and public policy ramifications; Nature Neuroscience vol. 8, No. 11, Nov. 2005; 1 page.

DiClemente, Ph.D., et al., Readiness and Stages of Change in Addiction Treatment, *The American Journal on Addictions*, Coypright 2004; 13: 103-119.

Fussel, Sidney; The Next Data Mine is Your Bedroom, Nov. 17, 2018, 6 pages.

Gainsbury, A systematic Review of Internet-based therapy for the Treatment of Addictions, Southern Cross University, 2011, vol. 31, No. 3, pp. 490-498.

Gotham, Diffusion of mental health and substance abuse treatments; development, dissimentation, and implementation; 2004; absract; 1 page.

Gravenhorst et al., Mobile Phones as Medical Devices in Mental Disorder Treatment: an Overview; Personal and Ubiquitous Computing, 2015, abstract: 2 pages.

Gustafson et al., An E-Health Solution for People with Alcohol Problems; ARCR/Alcohol Research Current review; 2011; 33(4): pp. 327-337.

Gustafson, Ph.D., et al., Explicating an Evidence-Based, Theoretically Informed, Mobile Technology-Based System to Improve Outcomes for People in Recovery for Alcohol Dependence; NIH Public access, Author Manuscript, Subst Use Misuse. 2011; 46(1):96-111. doi:10.3109/10826084.2011.521413.

Heron et al., Ecological Momentary Interventions: Incorporating Mobile Technology in to PSychosocial and Health Behavnior Treatments; HHS Public Access; Author Manuscript; Published on-line 2009; Br J Health Psychol. Feb. 2010: 15(Pt 1): 22 pages.

International Search Report and Written Opinion for PCT/US2017/066134 filed Dec. 13, 2017 which claims priority to the same parent application as the instant application, dated Mar. 29, 2018, 11 pages.

International Search Report and Written Opinion for PCT/US2017/066136 filed Dec. 13, 2017 which claims priority to the same parent application as the instant application, dated Apr. 9, 2018, 15 pages.

Kaplan et al., Bringing the Laboratory and Clinic to the Community: mobile technologies for health promotion and disease prevention; Annual Review of Psychology; 2013; abstract; 2 pages.

Kelly, Laura; Teen suicide rate suddenly arises with heavy use of smartphones, social media, The Washington Times—Tuesday, Nov. 14, 2017; https://www.washingtontimes.com/news/2017/nov/14/teen-suicides-rise-with—smartphone; 4 pages.

Lee et al., The SAMS: Smartphone addicion mangement System and Verification; Journal of Medical Systems; 2014, abstract; 2 pages.

Luxton et al., mHealth for Mental Health: Integrating Smartphone Technology in Behavioral Healthcare, Professional Psychology: Research and Practice, 2011, vol. 42, No. 6. pp. 505-512.

McClure et al., Utilization of Communication Technology by Patients Enrolled in Substance Abuse Treatment, NIH Public Access, Author Manuscript, Drug Alcohol Depend. Apr. 1, 2013: 129(1-2): 145-150. doi:10.1016/j.drugalcdep.2012.10.003.

McKay et al., Conceptual, methodological, and analytical issues in the study of relapse, Copyright 2005, www.sciencedirect.com, 19 pages.

McLellan, et al., Reconsidering the evaluation of addiction treatment: from retrospective follow-up to concurrent recovery monitoring; Copyright 2005 Society for the Study of Addiction; Addiction, 100, 447-458.

Stacy et al., Implicit Cognition and Addiction: A Tool for Explaining Paradoxical Behavior; HHS Public access, Author Manuscript, Ann. Rev. Clin. Psychol. 2010: 6: 22 pages.

The Conquer Quiz, Test for Alcoholism, conqueryouraddiction.com, accessed Dec. 7, 2017, 2 pages.

Nonfinal Office Action for U.S. Appl. No. 16/654,708 which names the same inventor/applicant but is not related through a priority claim; dated Jul. 15, 2020, 38 pages.

Final Office Action for U.S. Appl. No. 16/700,561 which names the same inventor but is not related through a priority claim; dated Oct. 8, 2020; 52 pages.

Notice of Allowance for U.S. Appl. No. 16/654,708, filed Oct. 16, 2019 (issued as U.S. Appl. No. 10/853,897 on Dec. 1, 2020) which names the same inventor/assignee but is not related through a priority claim; dated Oct. 26, 2020; 8 pages.

WO 2016/178617; Andersson, Karl; Method and Device for Estimating a Risk of Relapse of Addictive Behavior; Nov. 10, 2016, pp. 1-44 (Year: 2016).

USPTO Nonfinal Office Action for U.S. Appl. No. 17/192,381 that names the same inventors and assignee but is not related through a priority claim, dated Aug. 4, 2022, 62 pages.

\* cited by examiner

- ASSESS TRIGGER/RELAPSE RISK
- LEARN/MODIFY RISK ALGORITHMS

| DETERMINE/PREDICT TRIGGER RELAPSE RISK | ☐ - REPRESENTS MAJOR STEP, PROCESS, OR OPERATION |
|---|---|

| ADDICT #243 TRIGGERS | RISK PRIORITY/ SEVERITY (H/M/L, 1-10) (10 HIGHEST) | LOCATION/CONTEXT ELEMENTS/SENSORS MONITORED/ANALYZED | RISK FORMULA; RISK ACTION CLASSIFICATION |
|---|---|---|---|
| BOREDOM | RP = HIGH (RP SCORE=9) | A. ADDICT STAYS IN ONE PLACE MORE THAN X HOURS (EXCEPT SLEEP HOURS) = A=X-2; ZERO LOWEST VALUE) <br>B. LOW BLOOD PRESSURE (BELOW 100/70 (YES/NO = 1/0) <br>C. BOREDOM BUTTON PUSHED = 10) | RISK = RP/5*(A +(B*2)+C) <br>RISK CLASS: >=6 THEN TRIGGER BASED; <6 THEN RESOURCE-BASED |
| DEPRESSION | MED (5-) | A. SENSOR 1 VALUE <br>B. SENSOR 2 VALUE <br>C. DEPRESSION BUTTON PUSHED =10 | RISK = A +(B*2)+C/RP <br>RISK CLASS: TRIGGER-BASED (DEFAULT) |
| INSOMNIA | LOW (3) | A. UNUSUAL NIGHT-TIME MOVEMENT <br>B. HIGH RESTLESS SLEEP SCORES (E.G. VIA SLEEP NUMBER BED) | RISK = A +(B*3) – RP <br>RISK CLASS: ACTION CATEGORY BASED |
| YELLING/ CONFLICT | MED (6) | A. LOUD NOISES DETECTED <br>B. DISTRESS DETECTED (ELEVATED BLOOD PRESSURE, RAPID RISE IN SKIN TEMPERATURE) | RISK = A +(B*4) + RP <br>RISK CLASS: INTERFACE-BASED |

NOTE/LEGEND

| ▨ | INDICATES EMERGENCY-TYPE SITUATION OR PROCESS |
|---|---|

| MODIFY FREQUENCY AND SCOPE OF MONITORING |
|---|

- IDENTIFY/REFINE POSSIBLE ACTION(S)
- IDENTIFY/REFINE POSSIBLE RESOURCE(S)
- IDENTIFY/REFINE POSSIBLE INTERFACE(S)

RESOURCE-BASED ACTION PARAMETERS, W/ SUPPORTED ACTIONS & INTERFACE REQS

| SUPPORT RESOURCE | LOGISTICAL CONSTRAINTS, PREFERENCES | SUPPORTED ACTION(S) (PREFERRED SEQUENCE) | INTERFACE REQUIREMENTS / PREFERRED INTERFACE (S) |
|---|---|---|---|
| SPONSOR 1 | NO WEEKENDS | 1. LIVE, FACE-TO-FACE VISITS WITHIN 30 MINUTES OF CURRENT LOCATION | • FACE-TO-FACE<br>• HOLOGRAM<br>• PHONE CALL |
| MEDICAL PROFESSIONAL 3 (DR. D) | • AFTER 5PM<br>• TRIGGER(S):ANXIETY, DISORDER ONLY<br>• RELAPSE RISK >=8 | 1. PROTOCOLS A, D | 1. PHONE CALL ONLY |
| MOTHER | NONE | 1. FACE-TO-FACE MEETING<br>2. LIVE VIDEO/CALL<br>2. SEND MOM "MEDITATION MESSAGE" (VIA BEST "HUMAN" I/F, E.G. HOLOGRAM VOICE SYNTHESIS, VIDEO MESSAGE ETC.) | 1. LIVE VISIT<br>2. HOLOGRAM<br>3. SKYPE<br>4. PHONE CALL<br>4. VIDEO-BASED I/F IF LIVE NOT POSSIBLE |
| PROBATION OFFICER | ONLY IF RELAPSE IS EMERGENCY AND MEETS CONDITIONS OF PROBATION | 1. AUTO GENERATE CALL CONNECTING PROBATION OFFICER TO ADDICT CONTROLLER OFFICER<br>2. EVALUATE FURTHER OPTIONS UNDER PROTOCOLS E, F, G | 1. ANY |
| BOWLING @BRUNSWICK LANES (5 LOCATIONS) | MONDAY-SATURDAY 9AM – 11PM, SUNDAY 10AM-6 PM | 1. PROMPT FOR ANY HOBBY USAGE REQUIREMENT IN BAD WEATHER, OR BOREDOM IN GENERAL.<br>2. BRUNSWICK LOCATION B GOOD FOR SPORTS VIEWING-RELATED ACTIONS | 1. IN PERSON<br>2. USE WII VIDEO GAME AS A OPTION IF NO SUPPORT PERSONS AVAILABLE |
| SOCIAL MEDIA C | ALL MEMBERS OF GROUP C HAVE BEEN THROUGH PRIVACY PROTOCOL TRAINING AND VETTING | 1. PROMPT POSTS FROM ADDICT TO GROUP X FOR IDENTIFIED TRIGGER(S)<br>2. GENERATE AUTOMATED POSTS REQUESTING HELP; ROUTE RESPONSES TO ADDICT | POSTS AUTOMATICALLY DELETED AFTER 5 MINUTES |

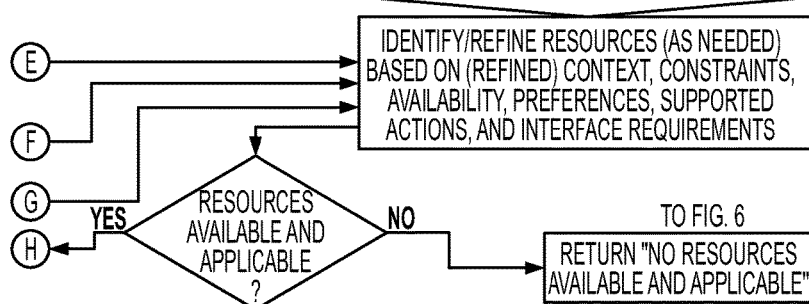

FIG. 7 (Cont.)

POSSIBLE ACTION – ADDICTION COMMUNITY MEETING
MEETING CRITERIA

| PERSON | SEVERITY THRESHOLD | MEETING CONTEXT CONSTRAINTS/LIMITATIONS | LOCATION LIMITATION |
|---|---|---|---|
| ADDICT 1 | HIGH (IMMEDIATE OR TRENDING) | 1. WOMEN-ONLY<br>2. ANXIETY, DEPRESSION-THEMED MEETINGS PREFERRED<br>3. AFTER 5 PM WEEKDAYS<br>4. PARTICULARLY INTERESTED IN ANXIETY-DEPRESSION DUAL TRIGGER MEETINGS | < 5 MILES CURRENT |
| SUPPORT PERSON 5 | MEDIUM OR ABOVE (IMMEDIATE OR TRENDING) | 1. CLOSED MEETINGS<br>2. HATES COFFEE | < 15 MILES CURRENT OR WITHIN 30 MINUTES |
| ADDICT 26 | MEDIUM OR ABOVE (IMMEDIATE ONLY) | 1. ONLY WHEN OUT-OF-TOWN (OUTSIDE OF HOME/WORK GEOFENCE)<br>2. OPEN, CLOSED MEETINGS | <10 MILES WITHIN 2 HOURS |
| ADDICT 62 | ANYTIME | 1. WHEN DRIVING<br>2. WHEN SPOUSE NOT NEARBY | BETWEEN 20 AND 50 MILES FROM HOME |

FLASH MEETING POTENTIAL SITES (COMMUNITY MEETING DB)

| POTENTIAL MEETING SITE | DESCRIPTION | CONSTRAINTS/ LIMITATIONS | COORDINATOR |
|---|---|---|---|
| X1, Y1 | STARBUCKS, CORNER OF LINDBERGH AND WALLEY STREETS | 1. STARBUCKS HOURS (LINK)(<br>2. NO MORE THAN 4 PEOPLE<br>3. COFFEE-DRINKERS PREFERRED | ADDICT 53 (LINK) |
| X3, Y3 | MISSOURI BAPTIST CHURCH (WEBSTER GROVES) | 1. ANYTIME EXCEPT SUNDAY<br>2. PROVIDE KEY CODE TO NEAREST INDIVIDUAL; CYCLE CODE AFTER MEETING (LINK) | MEDICAL PROFESSIONAL 5 (LINK) |
| X7, Y7, Z7 | 123 MAIN STREET, CITY HALL BUILDING, FLOOR 3, ROOM 312 | 1. PUBLIC ACCESS HOURS (LINK)<br>2. SECURITY GUARD NEEDS 30 MINUTE LEAD TIME (LINK) | FACILITY MANAGER'S OFFICE (LINK) |
| VIRTUAL 9 | ANYTIME | 1. NONE | TRIGGERMEETING.COM COORDINATORS |

FIG. 7A

IDENTIFY, IMPLEMENT BEST INTERFACE FOR ACTION

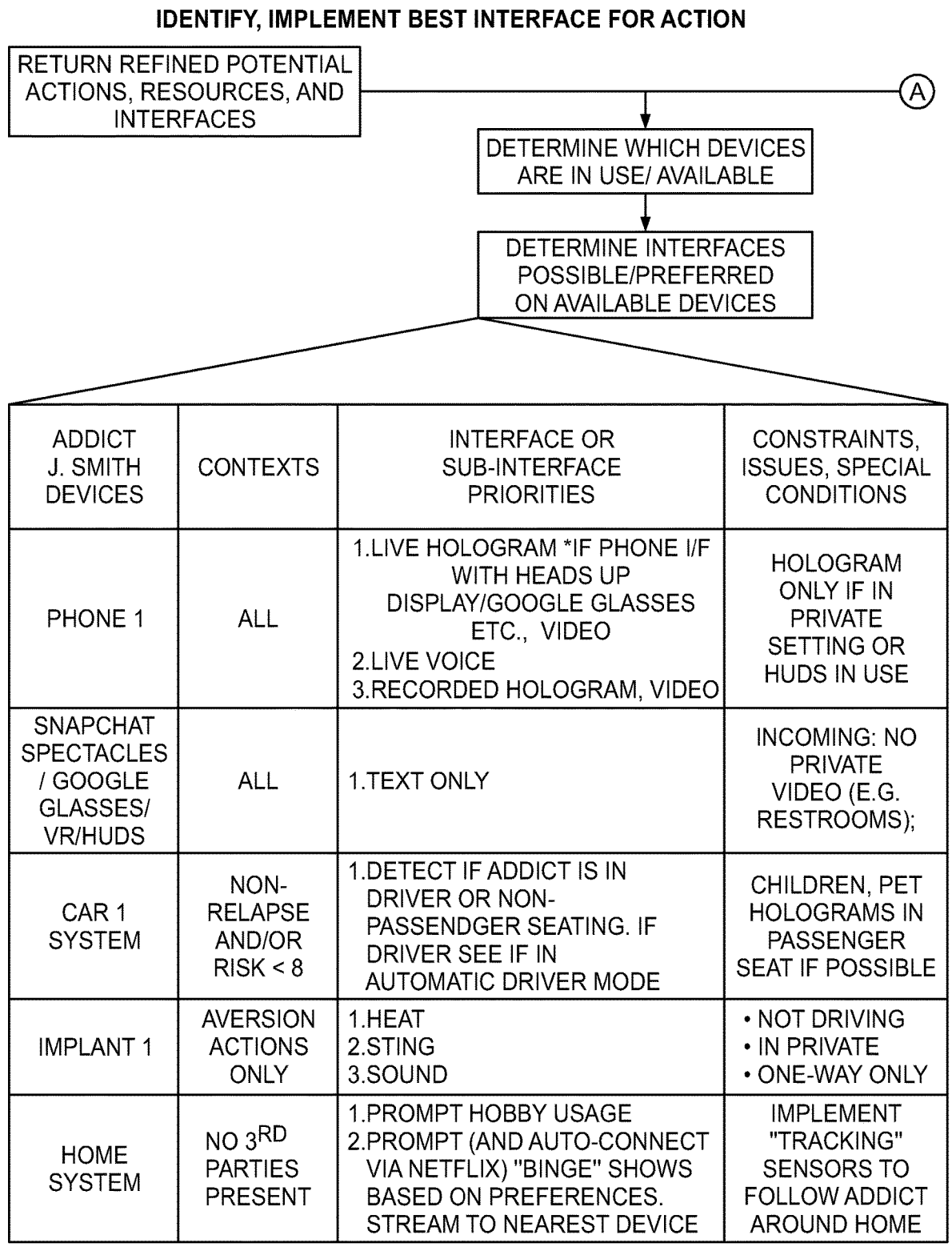

| ADDICT J. SMITH DEVICES | CONTEXTS | INTERFACE OR SUB-INTERFACE PRIORITIES | CONSTRAINTS, ISSUES, SPECIAL CONDITIONS |
|---|---|---|---|
| PHONE 1 | ALL | 1. LIVE HOLOGRAM *IF PHONE I/F WITH HEADS UP DISPLAY/GOOGLE GLASSES ETC., VIDEO<br>2. LIVE VOICE<br>3. RECORDED HOLOGRAM, VIDEO | HOLOGRAM ONLY IF IN PRIVATE SETTING OR HUDS IN USE |
| SNAPCHAT SPECTACLES / GOOGLE GLASSES/ VR/HUDS | ALL | 1. TEXT ONLY | INCOMING: NO PRIVATE VIDEO (E.G. RESTROOMS); |
| CAR 1 SYSTEM | NON-RELAPSE AND/OR RISK < 8 | 1. DETECT IF ADDICT IS IN DRIVER OR NON-PASSENDGER SEATING. IF DRIVER SEE IF IN AUTOMATIC DRIVER MODE | CHILDREN, PET HOLOGRAMS IN PASSENGER SEAT IF POSSIBLE |
| IMPLANT 1 | AVERSION ACTIONS ONLY | 1. HEAT<br>2. STING<br>3. SOUND | • NOT DRIVING<br>• IN PRIVATE<br>• ONE-WAY ONLY |
| HOME SYSTEM | NO 3RD PARTIES PRESENT | 1. PROMPT HOBBY USAGE<br>2. PROMPT (AND AUTO-CONNECT VIA NETFLIX) "BINGE" SHOWS BASED ON PREFERENCES. STREAM TO NEAREST DEVICE | IMPLEMENT "TRACKING" SENSORS TO FOLLOW ADDICT AROUND HOME |

FIG. 8

LOCATION/CONTEXT-BASED PRIVACY AND SECURITY

LOCATION/CONTEXT-BASED VERIFICATION QUESTION EXAMPLES

- WHERE HAVE YOU BEEN IN THE LAST (WEEK, MONTH, YEAR, ETC.)?
- WHERE HAVE YOU BEEN WITH YOUR YOUNGEST DAUGHTER (TIMEFRAME)?
- WHERE HAVE YOU NOT BEEN IN THE LAST MONTH?
- PLEASE SELECT YOUR VACATION-RELATED IMAGES (TIMEFRAME OPTIONAL)?
- PLEASE SELECT IMAGES* THAT ARE FAMILY ACTIVITY-RELATED.
- PLEASE SELECT IMAGES OF LOCATION(S) WHERE YOU CURRENTLY RESIDE.
- PLEASE SELECT IMAGES OF LOCATION(S) WHERE YOU HAVE NEVER BEEN
- PLEASE SELECT VACATION IMAGES BETWEEN X AND Y DATES
- PLEASE SELECT PICTURES OF YOUR FIRST DAUGHTER'S WEDDING LOCALES (CHURCH, RECEPTION, HONEYMOON)

LOCATION/CONTEXT-BASED VERIFICATION ANSWER EXAMPLES

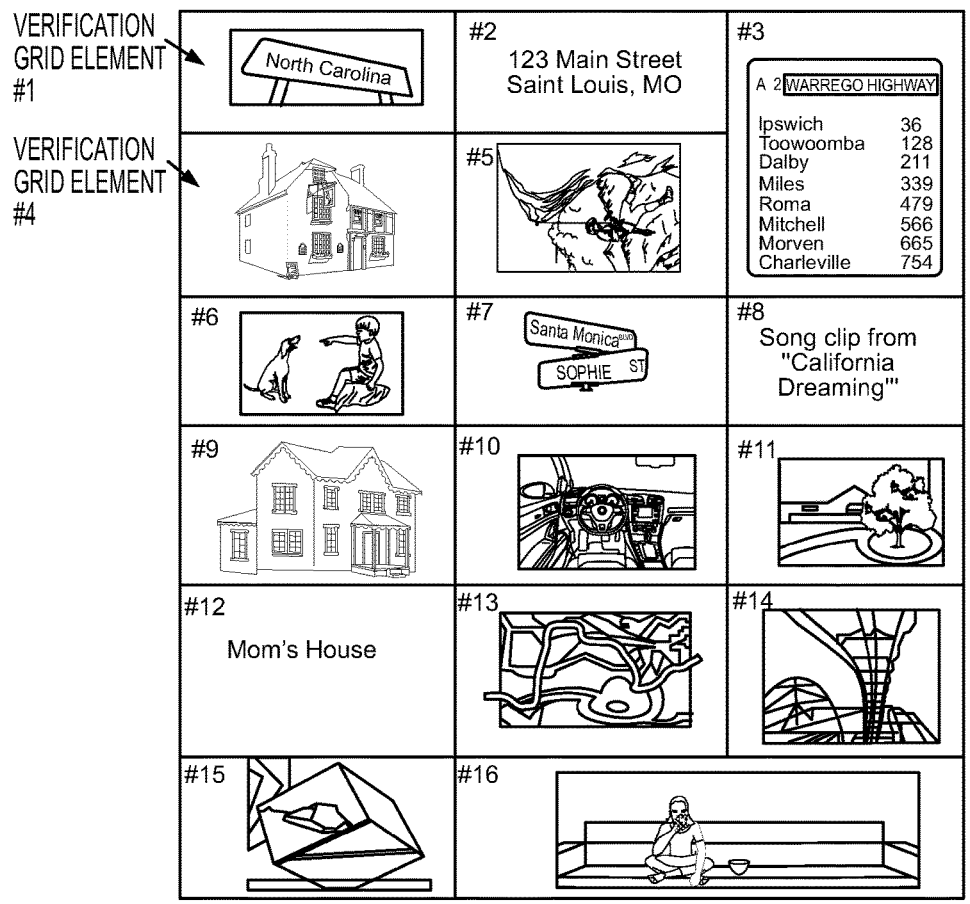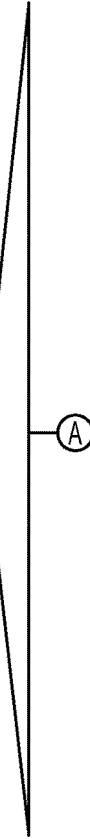

FIG. 11

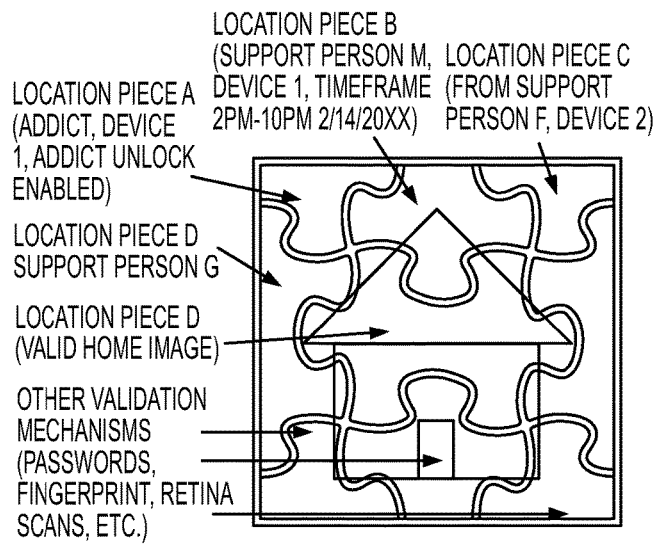

JIGSAW PUZZLE LOCATION/CONTEXT-BASED SECURITY

LOCATION/CONTEXT-BASED P/S MEMORY PROFILE

PRIORITY 1: HISTORICAL VACATION IMAGES (< 1 YEAR OLD; HAWAII, SKIING PREFERRED)

PR #2: ROAD SIGNS (NEAR MOTHER'S HOUSE) (NO TIME LIMIT)

PR #3 SONGS WITH LOCATIONS IN THEM (E.G. CALIFORNIA DREAMING, SWEET HOME ALABAMA, ETC.)

NO IMAGES FROM NORTH/SOUTH DAKOTA, BROTHER'S WEDDING

LOCATION PIECE A (ADDICT, DEVICE 1, ADDICT UNLOCK ENABLED)

LOCATION PIECE B (SUPPORT PERSON M, DEVICE 1, TIMEFRAME 2PM-10PM 2/14/20XX)

LOCATION PIECE C (FROM SUPPORT PERSON F, DEVICE 2)

LOCATION PIECE D SUPPORT PERSON G

LOCATION PIECE D (VALID HOME IMAGE)

OTHER VALIDATION MECHANISMS (PASSWORDS, FINGERPRINT, RETINA SCANS, ETC.)

| GRID # | SOURCE (DEVICE, PROCESS, ETC.) |
|---|---|
| #1 | GEOFENCE EXCEPTION DATA FROM CAR 1/DEVICE B |
| #2 | LAT/LONG TO ADDRESS TRANSLATION OF IMAGE #4 |
| #3 | ALGORITHMIC DERIVATION AND GRAPHICAL IMAGE CREATION FROM LAT/LONG CENTERPOINT OF VACATION X (ALL DEVICES) |
| #4 | PICTURE OF MOM'S HOUSE (DEVICE A) |
| #5 | VACATION PHOTO (FROM PERSON C HELMET CAM) |
| #6 | PICTURE OF PET (WHO DIED IN 2002) AT HOME XYZ |
| #7 | GRAPHICAL/AUGMENTED REALITY SIMULATION DERIVED FROM DRIVERLESS CAR C LOCATION OR IMAGE CAPTURE |
| #8 | AUDIO CLIP INDICATING VISIT TO CALIFORNIA IN TIMEFRAME P (MOBILE SOCIAL NETWORKING POST FROM FRIEND E |
| #9 | RANDOM LOCATION SAMPLE OF RETAIL "VISITS", WITH ADDRESS MATCHED WITH STORE NAME AND IMAGE PULLED FROM INTERNET |
| #10 | IMAGE TAKEN FROM CHILD DEVICE B, OR CAR SYSTEM A |
| #11 | SATELLITE IMAGE FROM GOOGLE MAPS OF HOMESTEAD A |
| #12 | COLLOQUIAL NAME OF MOM'S HOUSE (MANUALLY INPUT, TAGGED FROM PICTURE IN #4 OR FROM IMPORTED FROM FAMILYMAP APP (SEE RIGHT) |
| #13 | DELIBERATE DISTORTION/OBSTRUCTION OF CURRENT HOMESTEAD |
| #14 | 3D IMAGE OF SIX-FLAGS ROLLERCOASTER RIDE (3D DEVICE D) |
| #15 | A REVOLVING 3D IMAGE WITH DIFFERENT LOCATIONS (COMPOSITE) |
| #16 | VIDEO OF ME WATCHING TV IN LIVING ROOM (TV DEVICE 1) |

TIMEFRAME EXAMPLES
• SINCE D (DATE AND /OR TIME)
• LAST 24 HOURS
• LAST WEEK/MO/YR
• SINCE MOVE TO MOST RECENT ADDRESS
• BETWEEN X & Y
• NOT SINCE D OR BETWEEN X & Y

3RD PARTY APP IMPORT (AT&T FAMILYMAP EX.)

FIG. 11 (Cont.)

LOCATION/CONTEXT-BASED PRIVACY AND SECURITY (3D AND/OR JIGSAW)

EXAMPLE CONTROLLER KEYS FOR JANUARY 6TH

| CONTROLLER | LOCATION / CONTEXT (TIME) ZONE | KEY | DEVICE (SOURCE, ACCESS) | IMAGE TYPE | TIME STAMP | LOCATION/ CONTEXT TAGS |
|---|---|---|---|---|---|---|
| 1 (ADDICT JANE DOE, SUPPORT LIST G, SUPPORT PERSON #4) | A (00:01 TO 04:00 CST) | 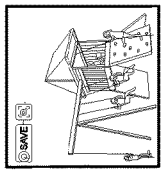 | S: IPHONE 2 A: PHOTOCAPABLE | 2D, VISUAL, PHOTO, COLOR, STRUCTURE, PERSONS | 7/3/20XX (SUMMER 20XX, 4TH OF JULY HOLIDAY) | OUTSIDE, SWINGSET, BACKYARD, PLAY, KIDS, SUMMER, NO RAIN, TREES, GRASS |
| 1 (ADDICT JANE DOE, SUPPORT LIST G, SUPPORT PERSON #4) | B (04:01 TO 08:01 CST) |  | S: GOOGLE GLASS; A: 3D ONLY | 3D, VISUAL, PHOTO/VIDEO, STRUCTURE, PERSONS | >2 YEARS ROLLING | OUTSIDE, SWINGSET, PLAY, KIDS, SUMMER, OCEAN, BEACH, VACATION |
| 2 (ADDICT JANE DOE, SUPPORT LIST G, SUPPORT PERSON #6) | C (8:01 TO 11:01 AM CST 1/6); | 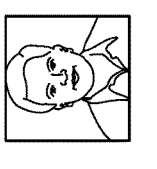 | S: IOT DEVICE X A: COMPUTER/LAPTO PS A OR D) | 2D, VISUAL ACCOMPANIED BY VOICE VERIFICATION; PERSON (1) | CURRENT (REALTIME STREAM, LESS THAN 1 HOUR HOLD) | SELFIE, NO BACKGROUND PICTURES, GLASSES; IN OFFICE/AT WORK |

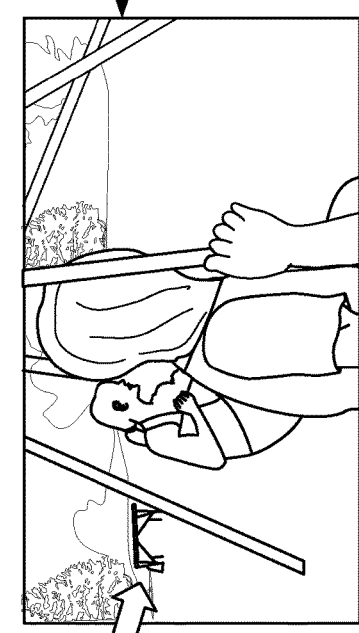

ADDICT DATA AND ANALYTICS
ADDICT-RELATED LOCATION/CONTEXT IMAGES, ADDRESSES, SYMBOLS, ICONS, AND OTHER MEMORY PROMPTERS

OTHER FORM EXAMPLES

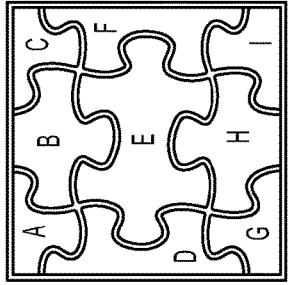
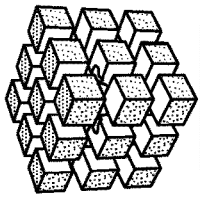
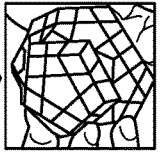
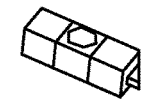

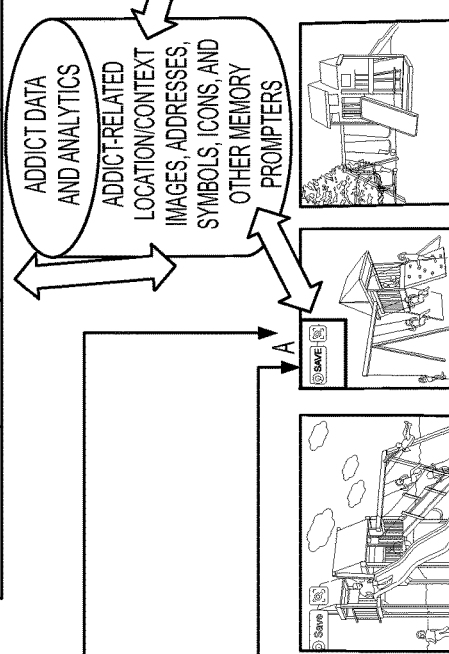

VIRTUAL "WHACK-A-MOLE" VERIFICATION
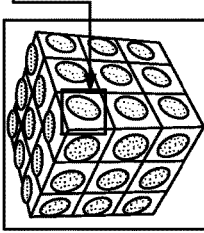

FIG. 14

SYSTEMS AND METHODS FOR MONITORING FOR AND LOWERING THE RISK OF ADDICTION-RELATED OR RESTRICTION VIOLATION-RELATED BEHAVIOR(S)

CROSS-REFERENCE TO RELATED APPLICATIONS

The present application is a continuation-in-part of allowed U.S. patent application Ser. No. 16/700,601 filed Dec. 2, 2019 (published as US2020/0107155 on Apr. 2, 2020 and issuing as U.S. Pat. No. 11,388,546 on Jul. 12, 2022).

U.S. patent application Ser. No. 16/700,601 is continuation of U.S. patent application Ser. No. 15/840,775 filed Dec. 13, 2017 (published as US2018/0173866 on Jun. 21, 2018 and issued as U.S. Pat. No. 10,555,112 on Feb. 4, 2020).

U.S. patent application Ser. No. 15/840,775 claims the benefit and priority of U.S. Provisional Patent Application Ser. No. 62/435,042 filed Dec. 15, 2016 and U.S. Provisional Patent Application Ser. No. 62/480,206 filed Mar. 31, 2017.

The present application is also related to the following:
- U.S. Pat. No. 10,477,342; U.S. Published Patent Application US2018/0176727; U.S. patent application Ser. No. 15/840,762
- U.S. Pat. No. 10,497,242; U.S. Published Patent Application US2019/0340906; U.S. patent application Ser. No. 16/516,822
- U.S. Pat. No. 10,853,897; U.S. Published Patent Application US2020/0051189; U.S. patent application Ser. No. 16/654,708
- U.S. Pat. No. 10,861,307; U.S. Published Patent Application US2020/0105113; U.S. patent application Ser. No. 16/700,561
- U.S. Published Patent Application US2021/0084451; U.S. patent application Ser. No. 17/104,136
- U.S. Published Patent Application US2021/0202067; U.S. patent application Ser. No. 17/192,381
- U.S. Published Patent Application US2022/0116736; U.S. Non-Provisional patent application Ser. No. 17/541,707
- U.S. Provisional Patent Application 62/701,252
- U.S. Provisional Patent Application No. 62/746,330
- U.S. Provisional Patent Application 62/986,382
- U.S. Provisional Patent Application No. 63/011,949
- U.S. Provisional Patent Application No. 63/120,834
- U.S. Provisional Patent Application No. 63/275,300
- U.S. Provisional Patent Application No. 63/294,815
- U.S. Provisional Patent Application No. 63/316,227
- U.S. Provisional Patent Application No. 63/344,976

The entire disclosures of the above patent applications and patents are incorporated herein by reference.

FIELD

The present disclosure generally relates to systems and methods for monitoring for and lowering the risk of addiction-related or restriction violation-related behavior(s).

BACKGROUND

This section provides background information related to the present disclosure which is not necessarily prior art.

Addiction to substances, such as alcohol and drugs, and activities, such as gambling, are a major scourge of society. Addictions can come in many forms, but generally can be put into two categories: 1) addiction to a substance, such as drugs, alcohol, or food, or 2) addiction to an activity, such as gambling, sex, or shopping. The human impact of an addiction can vary greatly in terms of physical toll on the mind and body as well as everyday life-damage such as destruction of families and job loss. Common life-mining addictions include those involving alcohol, prescription and non-prescription drugs, cigarettes/nicotine, and gambling. Less common but very serious addictions involve overindulging in sex, eating, and avoidance/lack of food (e.g., anorexia or bulimia). Other addictions typically (but not always) can be considered relatively minor or annoying such as shopping, exercise, work, sports viewing, beauty enhancement/plastic surgery, videogames, or even surfing the Internet or constant use of smartphones, to name a partial list.

The term addiction has many definitions, but in general it refers to a person or persons who cannot, or will not, stop using or doing something that is potentially harmful to them and/or others around them. While addiction often conjures images of drunks or drug addicts roaming the streets, in reality addiction impacts all walks of life, from professionals to blue-collar workers to athletes to celebrities to stay-at-home parents, even to children. Many addicts live otherwise useful, functional lives, which can be greatly improved if their addiction is effectively treated.

Various types of addiction treatments, programs, and other methods for addressing addiction have been around for many decades. Examples include: 12-Step Programs such as Alcoholics Anonymous (AA), Acupuncture, Aversion Therapy (multiple forms), Behavioral Self-Control Training, Cognitive Therapy, Going Cold Turkey, Community Reinforcement, Diet-based Programs, Drug-based Treatments (multiple forms), Exercise-based programs, Hypnosis, Interventions, Meditation, Motivational programs, Nutrition-based programs, Rehabilitation (Inpatient and Outpatient)/Hospitalization stays, Religious-based programs, Self-Change Manuals/Guides, (Traditional) Psychotherapy (multiple forms), Spiritual Immersion, and Work/Treatment programs to name some of the more commonly-known approaches.

DRAWINGS

The drawings described herein are for illustrative purposes only of selected embodiments and not all possible implementations and are not intended to limit the scope of the present disclosure.

FIG. 1 is a diagram of an example system for determining location and context of an addict, a support network, and other information and aspects of an addict's personal and professional life for addiction treatment purposes, including relapse prevention and containment. This diagram includes various example networks and technologies that may be used for collecting and analyzing the addict's location and context. Also shown are example data sources and analytical engines that may be needed to process such data and to identify and implement actions to preempt, prevent, and/or contain any relapse.

FIG. 2 describes an example Addict Monitor/Controller (AMC) device that may be used to collect, process, and disseminate context and addiction trigger-related data from and about an addict via various sensors and other data collection mechanisms, and to interface with/to the addict and 3rd party mechanisms. The device may also provide mechanisms to provide feedback to the addict and assist in the implementation of relapse-related preventative and containment actions.

FIG. 2a provides examples of distributed sensor deployment, data collection options, localized sensors, and localized networks that may be used in exemplary embodiments.

FIG. 2b provides examples of internet of things (IoT) addict-related sensors, devices, and networks that may be used in exemplary embodiments.

FIG. 3 depicts example steps for monitoring an addict's triggers, and in the course of doing so assessing/predicting the addict's risk of relapse. FIG. 3 also describes identifying possible resources that could help the addict, and the actions that could be taken to prevent, preempt or contain a relapse. FIG. 3 also describes an example process for selecting such resources and actions.

FIG. 4 depicts an example system and example process for determining the location/context of an addict as well as the location/context of support resources using a variety of sensors and other information sources.

FIG. 5 describes an example system and example process for assessing an addict's trigger/relapse risk. FIG. 5 also describes how such algorithms could be made self-learning to better assess an addict's relapse risk.

FIG. 5A depicts an example embodiment of a method for managing damage control and recovering from a relapse situation.

FIG. 5B provides examples of risk, support areas maps, and map mashups.

Figure 7:
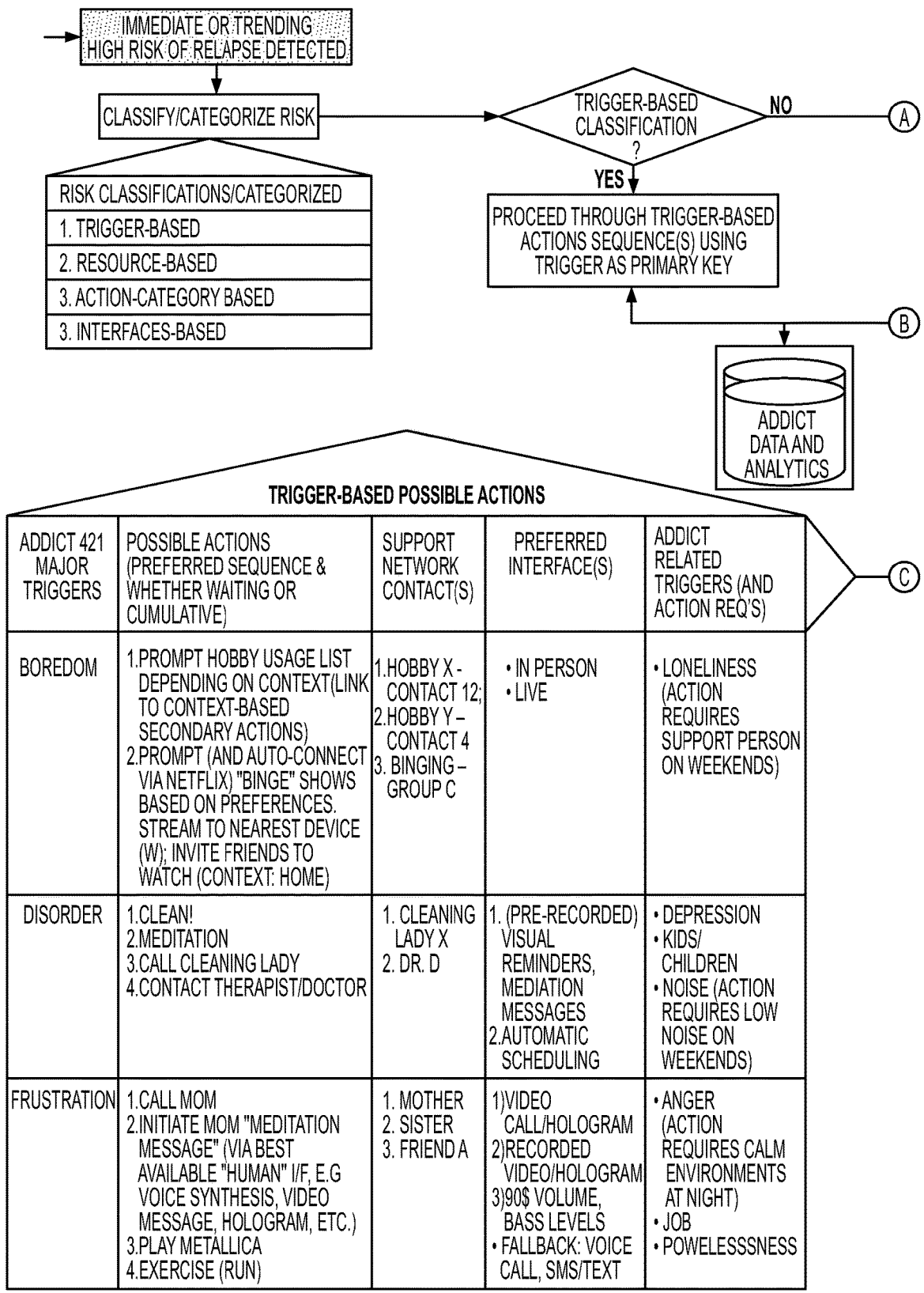
Figure 7:
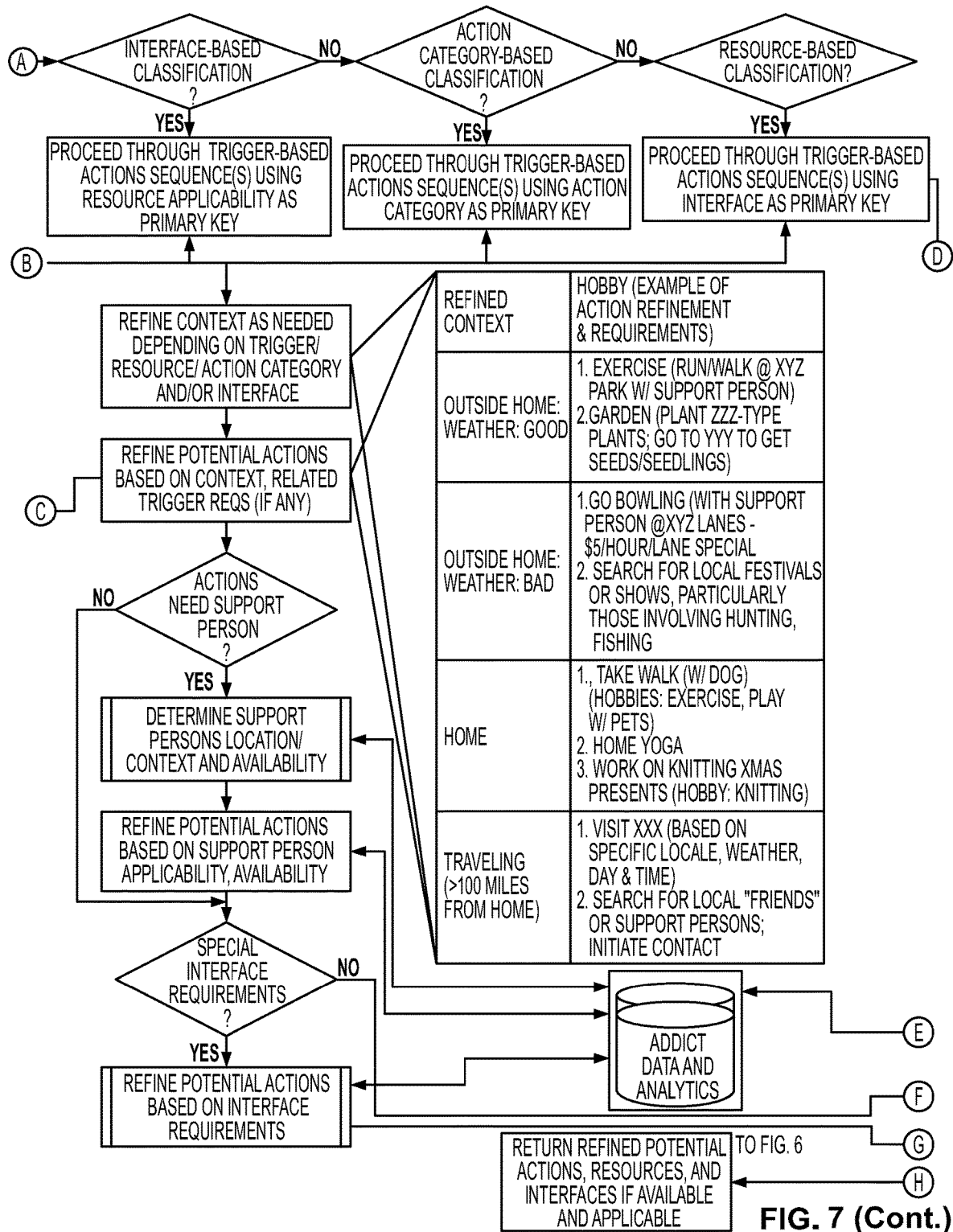

FIG. 7 describes example ways to identify/determine and select the best actions and resources when relapse risk is high.

Figure 7A:
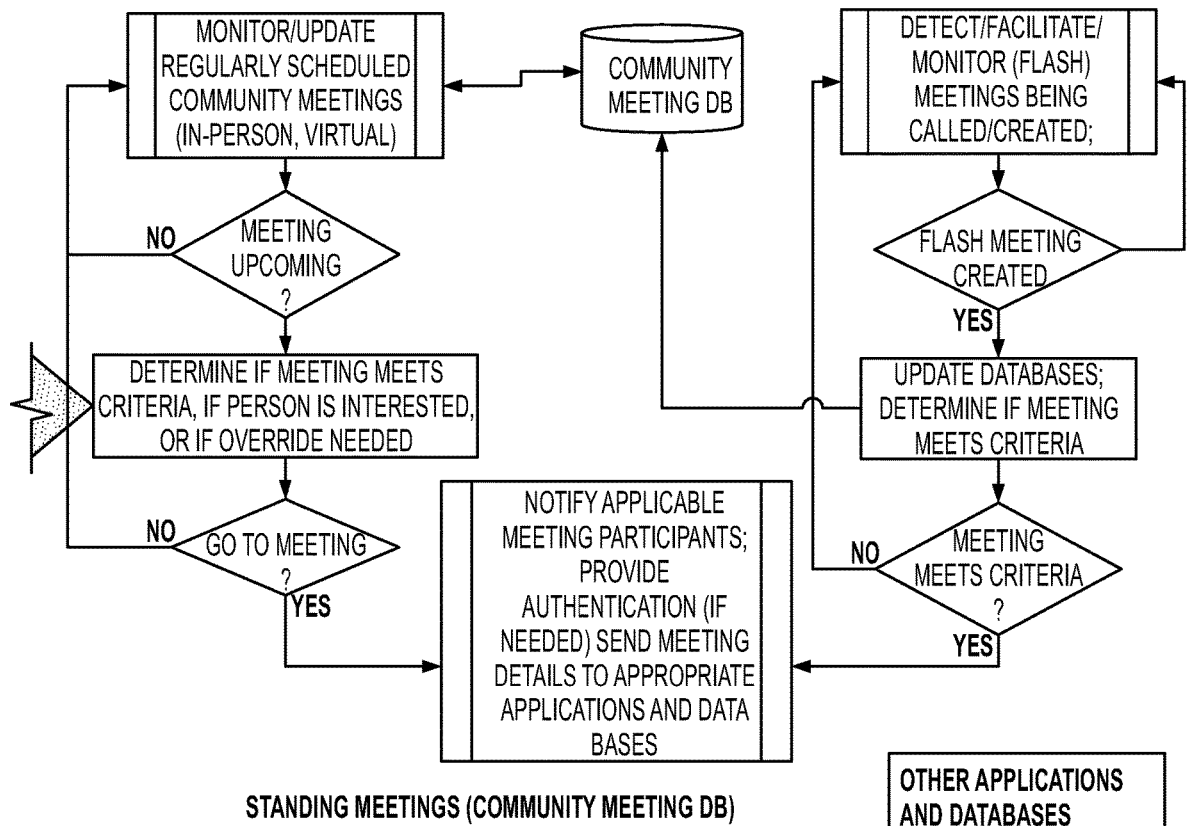

FIG. 7A describes an example of an action-determining sub process—specifically, ways to utilize regularly scheduled addict community meetings or spontaneous, unscheduled, flash addict community meetings.

Figure 8:
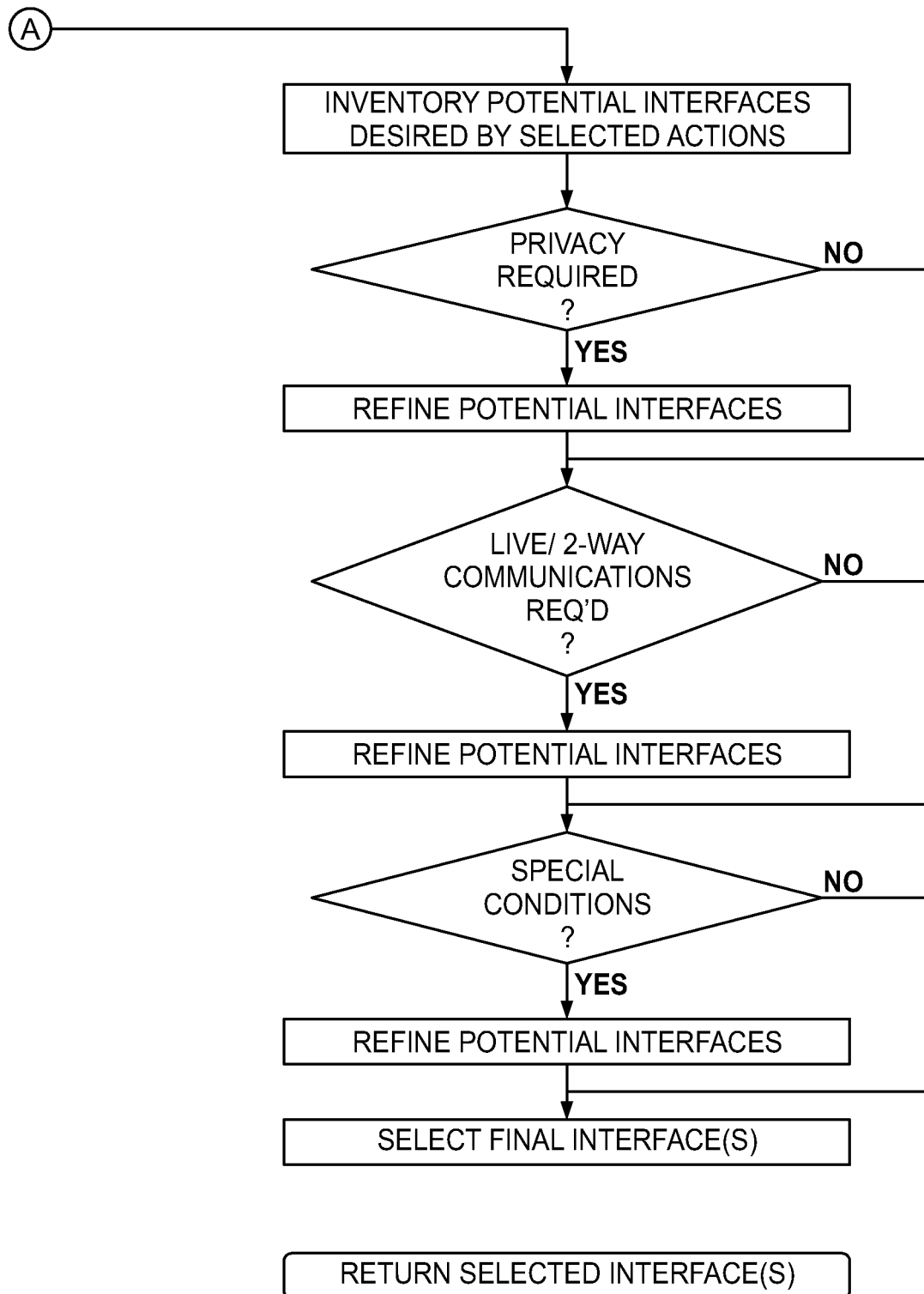

FIG. 8 describes example ways to select the best interface(s) for interacting with an addict, including implementing relapse prevention actions.

Figure 9:
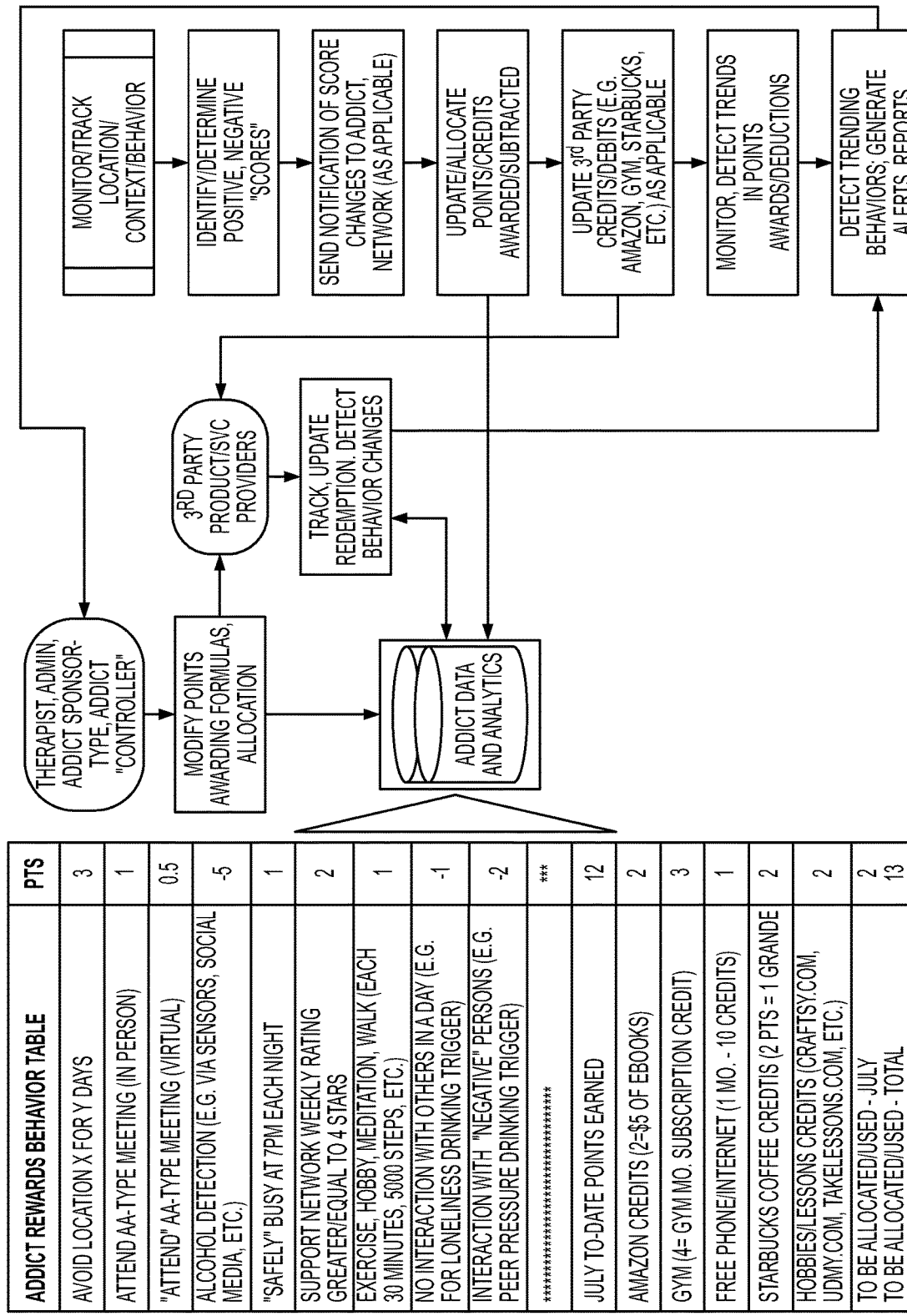

FIG. 9 describes an example addict rewards/demerits system based on an addict's behaviors and actions, which may include rewarding (or punishing) an addict based on behavior via tracking and data analytics and various reward mechanisms.

Figure 10:
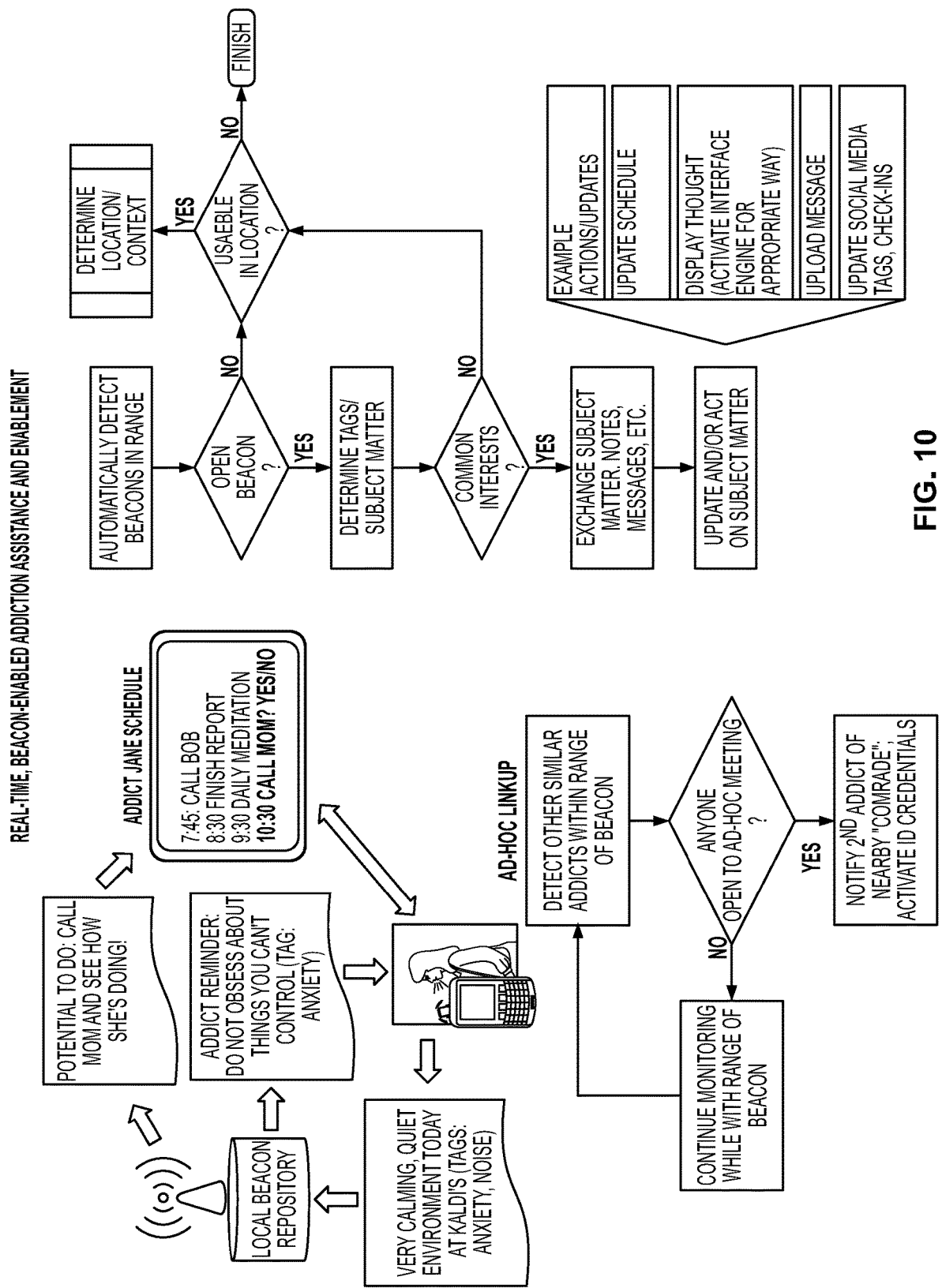

FIG. 10 describes example ways in which addicts can receive and transmit sobriety ideas in public and private places via beacons. FIG. 10 also illustrates example ways in which Real-Time Location System (RTLS) technologies can be used to enable ad hoc, spontaneous, unscheduled, or flash addict meetings between people with similar addiction issues.

FIG. 11 thru 14 describe examples of using location and/or context information to provide privacy and security for data collected in various implementations of the present disclosure.

Figure 15:
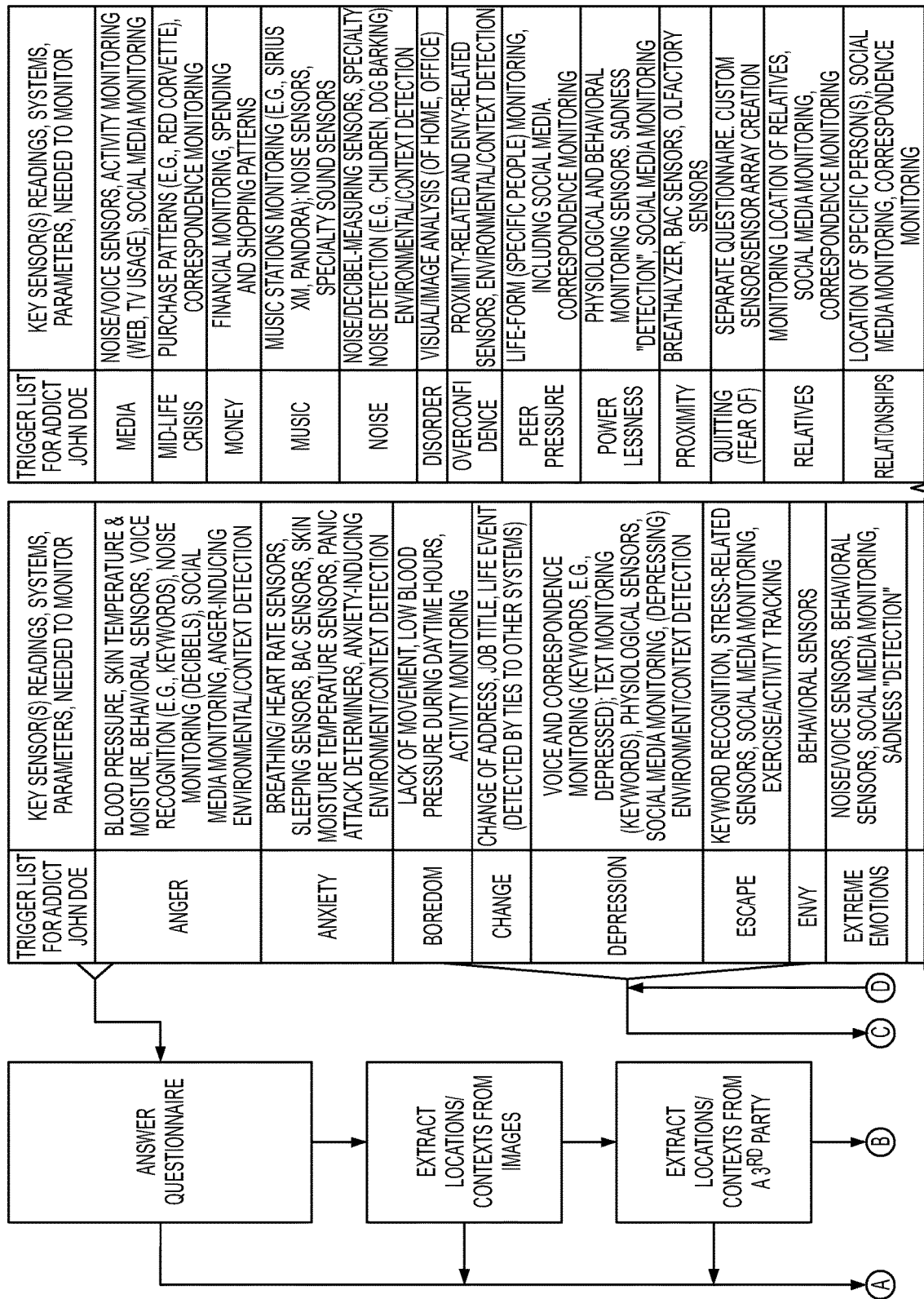
Figure 15:
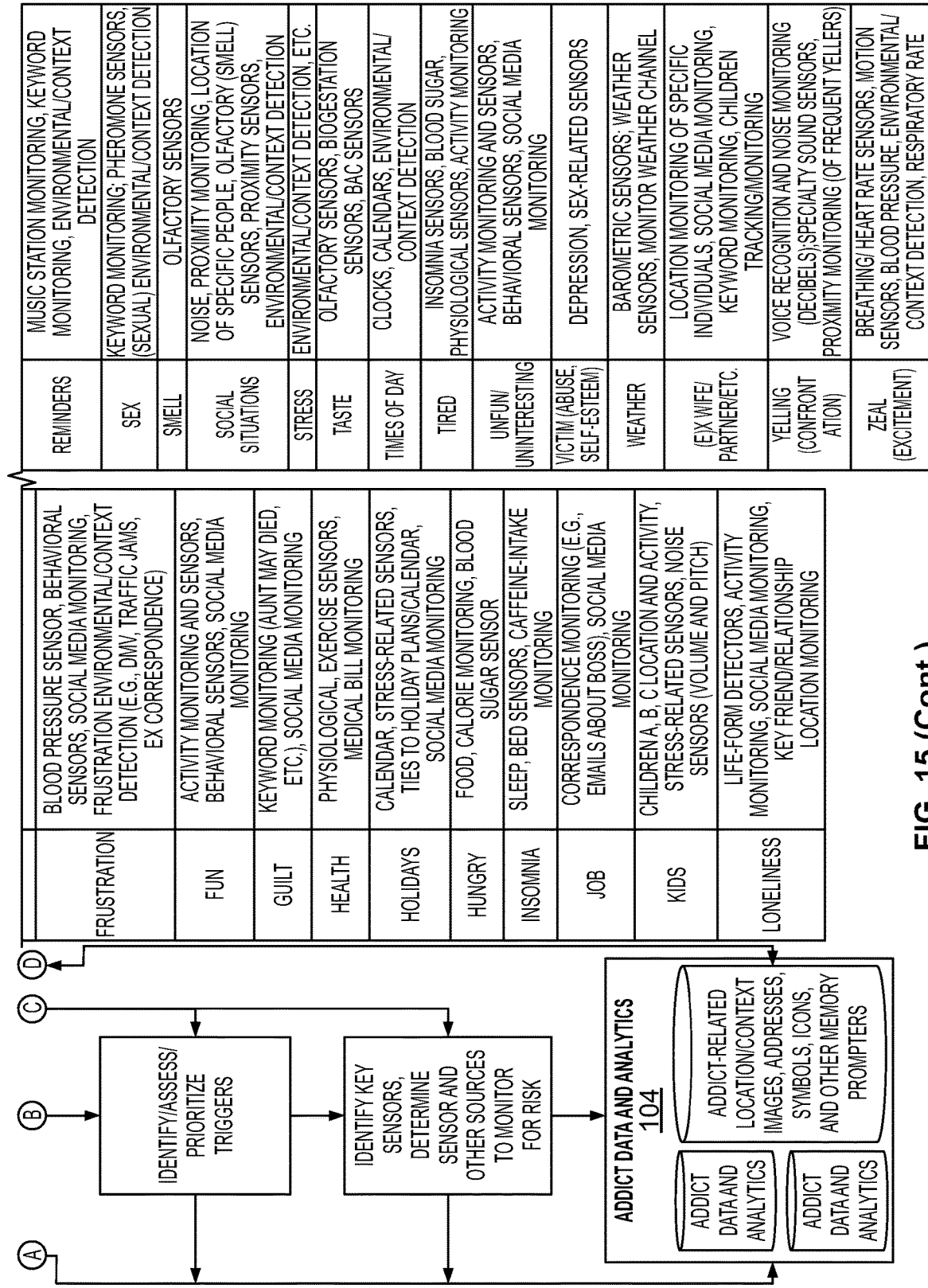

FIG. 15 depicts an example embodiment of a method for monitoring for a risk of a pre-identified behavior (e.g., pre-identified addict-related undesirable behavior, etc.). FIG. 15 also includes example triggers, priorities, and initial risk assessment/detection sensors.

Figure 16:
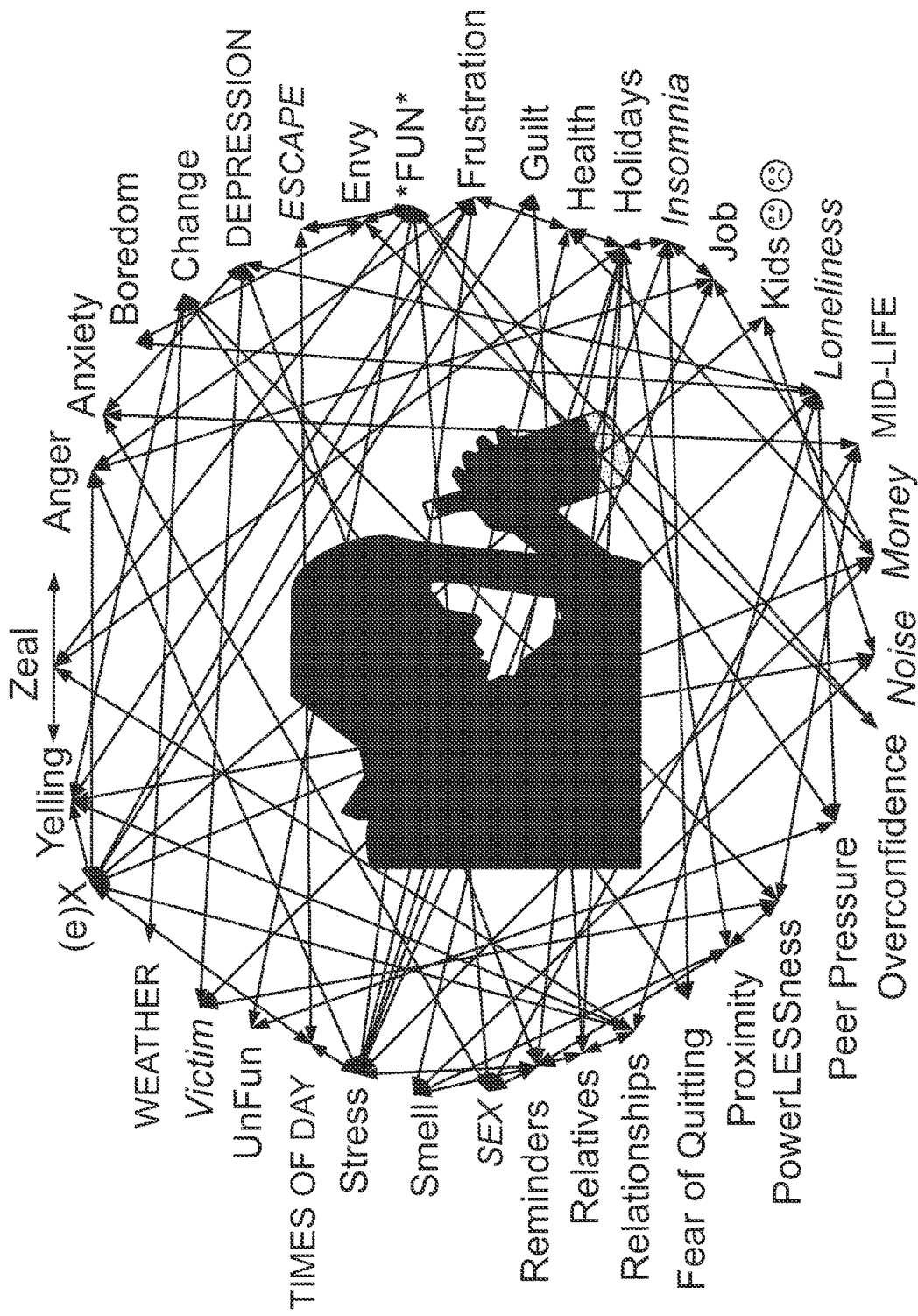

FIG. 16 is a diagram depicting various examples of triggers (e.g., drinking triggers, etc.) and how the triggers may be related or interconnected such that one or more trigger(s) may activated one or more related trigger(s).

DETAILED DESCRIPTION

Example embodiments will now be described more fully with reference to the accompanying drawings.

Sometimes addiction treatments such as those mentioned above work. But very often addiction treatments do not work, at least not for long. While there are many reasons why an addiction treatment might not work, one common reason is that most treatments are most effective when they are actively being implemented, such as when a person is actively in residence in a treatment facility, attending an AA meeting, or in a therapy session. Put another way, one of the vulnerabilities of these and many of the above approaches is that their effectiveness is closely tied to their immediacy, both in terms of physicality to the addict (for treatments that have a personal counseling and/or physical location element) and in time—how fresh the teachings of the program are in the mind of the addict, not to mention how long the addict is willing to actively participate in treatment or treatment-related activities. This is particularly true for many of the most common treatments, such as rehab facility stays (inpatient or outpatient), therapy sessions, or alcoholism-related community meetings. Once the addict leaves those (usually physical, but increasingly virtual or augmented) places where the treatment takes place, the lessons or motivations from those treatments become weaker or start to fade, while at the same time opportunities and temptations to partake in the addiction increase.

Another issue with the above treatments is that many surprisingly place little emphasis on the triggers that may cause or set off one's addiction-particularly in understanding what situations, circumstances, or mindsets (broadly, triggers) make or drive the addict to want to use the substance and/or activity in question. Triggers are what very often drives the desire to use. By way of background, triggers may be situations, circumstances, activities, events, and mental thought processes and frames-of-mind that tempt or cause an addict to want to use a substance or engage in an activity. Without such detailed knowledge of the triggers of addiction, such treatments often focus on symptoms, or controlling such triggers after they occur. In any event, even in treatment programs where understanding of addiction triggers are emphasized, such emphasis is usually focused on general understanding of the triggers, not in dealing with them on a practical, day-to-day, hour-by-hour basis of everyday life.

As the addict gets farther away from the treatment program—physically and/or in time—the lessons from those programs naturally start to fade, becoming less effective, and, in turn, making the addict more susceptible to relapse. Thus, it is desired to find ways of keeping treatment lessons fresh in the mind of the addict, or alternatively refreshing them in a way to actively deter an addict from relapsing. It is also unfortunately true that even the best-intentioned addict cannot see all the possible situations that might tempt or trigger the addict to relapse in time to avoid such triggers, or at least mitigate them—the addict may find himself in a high-risk environment before realizing it. After recognizing the above, the inventor hereof has further recognized a need for a way to use technology to provide treatment reinforcement when the addict is away from the place of primary treatment(s), while simultaneously protecting the addict from the temptations/addiction triggers of their addiction.

As mentioned earlier, some, but not all of the treatment programs above include education about addiction triggers. Such triggers include situations, circumstances, activities, events, and mental thought processes and frame-of-minds that tempt or cause an addict to want to use a substance or engage in an activity known or identified to be detrimental to the addict and/or others. Examples of triggers include but are not limited to: Anger, Anxiety, Boredom, Change, Children, Conflict, Depression, Disorder, Embarrassment, Escape, Envy, Excitement, Fun, Frustration, Guilt, Health issues, Holidays Hunger, Insomnia, Job stress, Loneliness, Mid-life Crises, Money worries, Noise, Overconfidence, Pain, Peer Pressure, feeling Powerful or Powerless, Proximity (to the substance), Fear of Quitting (the substance or activity), Relationship issues, Relatives, Reminders, Sex, Shopping Situations, Social Situations, Special Occasions, Stress, Taste and Smell, Times of Day, being Tired, being Unfun, being a Victim (or crime, abuse), ex-spouses/partners, Yelling, even Season or Weather changes or Music. There are potentially hundreds of possible addiction triggers, and many thousands of trigger combinations.

It is when an addict's most vulnerable triggers become active or are present that the addict is most vulnerable to relapse. Thus, if boredom is a major trigger for an addict, it is imperative to keep the addict from becoming bored, or failing that, to respond to, and correct a bored addict before the temptation to use a substance or engage in an addictive activity becomes too strong and relapse occurs. Determining an addict's triggers and proscribing actions and activities to deal with those triggers without relapsing is anticipated to become a more common and important part of many addiction treatments, and is at the core of various exemplary embodiments of the present disclosure. In particular, various exemplary embodiments disclosed herein focus significant attention on understanding an addict's triggers and, in particular, using an array of sensors and other information to anticipate and/or detect triggers that are active, present, or in danger of becoming active or present, particularly by using location and context to a) anticipate, predict, and/or preempt an addict's triggers from becoming active or present, b) prevent a relapse when triggers do become active by initiating one or more actions, activities, and/or contacts with an addict's support network, and/or c) contain or manage a relapse if and when its occurs.

Surprisingly, there is relatively little application of technology in addiction treatment in the prior art, less that incorporates location, and practically nothing that utilizes context. For example, location technology has been used to aid patient recovery, but this was focused on physical rehabilitation of ambulatory (hospital) patients, not addiction recovery nor patient monitoring outside a hospital environment. Location technology has also been used as a small part of an Internet addiction treatment, which focuses primarily on understanding the amount and type of internet activity that is taking place (e.g., games, certain types of websites, etc.). This latter example also utilized the concept of support groups, but not in a manner that emphases location or context of the addict or the support group.

Exemplary embodiments of addiction treatment systems and methods are disclosed herein. One example embodiment of a system includes a plurality of user devices, sensors, and other technology to: determine, through one or more communications networks, the location of an addict and the context of the addict at the location; evaluate a risk of relapse by the addict in relation to the location and/or the context; facilitate one or more actions and/or activities to mitigate the risk, if any, and/or react to a relapse, if any, by the addict. By way of example, the context may include a situation, environment, and/or state of mind of the addict at the location. The context may include why the addict is at the location, who the addict is with at the location, what the addict is doing at the location, when (day/time) the addict is at the location, and/or how the addict got to the location, etc.

One example embodiment of a method of treating an addict for an addiction includes determining, through one or more communications networks, the location of an addict and the context of the addict at the location, where the context includes a situation, environment, and/or state of mind of the addict; evaluating a risk of relapse by the addict in relation to the location and/or the context; and facilitating one or more actions and/or activities to mitigate the risk, if any, and/or react to a relapse, if any, by the addict. This may be done primarily by determining the location and context of the addict and assessing that data relative to the addict's addiction triggers.

In various exemplary embodiments, a plurality of user devices, sensors, and/or other technologies are provided to protect privacy and security of information collected as disclosed herein. In some exemplary embodiments, experience-based data, including but not limited to location and/or context data, may be used to condition access to protected information. Access to the protected information may be permitted to a permittee based on recognition by the permittee of the experience-based data.

The distinction between location and context and its importance should be noted. The location of a person is often (not always) part of determining a person's broader context. With respect to exemplary embodiments of the present disclosure, depending on the circumstances of an individual, the location of the person may be most important; in other circumstances, the broader context may be more important. For example, if the methods and/or apparatus described in the present disclosure determine that the best course of action may be to attend a nearby AA (Alcoholics Anonymous) meeting, the specific circumstances of that person at that time may dictate that the addict should attend the nearby AA meeting. In another exemplary embodiment, the methods/apparatus of the present disclosure may determine that for the addict's current situation and addiction inducing trigger level (e.g., anxiety trigger, etc.), the addict should meet a certain person in the addict's support network who also has the same or similar issues (e.g., anxiety and alcoholism etc.) issues at an (e.g., anxiety-related, etc.) meeting that is quite a bit farther away than the addict's current location. Here, the context of the addict is more important than just the addict's location.

In various embodiments of the present disclosure, addicts can be helped to detect and deal with the triggers that initiate or enhance the craving to indulge in their addiction. There generally are many such triggers, including but not limited to: Anger, Anxiety, Boredom, Change, Conflict, Depression, Disorder, Envy (desire to) Escape, Excitement, Extreme Emotions, Fear, Frustration, Guilt, Health problems, Holidays, Hunger, Insomnia, Job issues, Kids/Children, Loneliness, Media (TV, Radio, the Internet) marketing, Mid-Life Crisis, Money problems, Music, Noise, Overconfidence, Peer Pressure, Power, Powerlessness, Proximity (to an addictive substance), (fear of) Quitting, Relationships, Relatives, Reminders, Sex, (change of) Seasons, Smell, Social Situations, Stress, Taste, Times of Day, (being) Tired, (feeling) Not Fun or Unhappy, (feeling) Victimized, Weather, Yelling, and Zeal (high energy). Many addicts are especially vulnerable to relapsing when faced with one or more of these triggers. Some of these triggers have a location dimension to them, most notably proximity to an addiction substance or activity, and many more have a location element in the actions or solutions for dealing with those triggers (and/or high-risk for relapse situations) without relapse. For example, a response to the detection of the Boredom trigger may require the addict to go to a certain place to do a certain activity. Loneliness would involve visiting with or visit by a member of the addict's support network. Noise could require going to a quiet place to meditate, such as a church or library, or to retreat to a serene program on a virtual reality device. This kind of information could be captured in a data profile (e.g., an addict profile including actions to take in relation to the addict, etc.) stored in a database or similar data store.

The present disclosure includes various exemplary embodiments of systems and methods that utilize the location and context of an addict and other resources to a) preempt trigger and/or high risk relapse situations, b) prevent relapse in high risk situations, and/or c) respond to, manage, and recovery from a relapse when they do occur. Various embodiments include collecting, aggregating, and analyzing addict- and addiction-related data specific to that addict's condition, vulnerabilities, motivations, and usage triggers. Such data/information can be collected from a wide variety of sensors and other data sources, including but not limited to: personal devices such as smartphones, tablets, computers, PDAs, wearables (data collection devices worn on the person, such as Fitbit, etc.), implants, Google Glass, etc.; nearby sensors or devices such as security/video cameras, smart devices (such as smart home-related sensors, etc.), crowdsourcing data collection applications of nearby users, building/store/office Wi-Fi networks, location-sensitive beacons, etc.; and/or extended data collection mechanisms such as road traffic sensors, public video cameras or billboard displays, weather data collection sensors, law enforcement/security-related devices, etc.

Various system and method embodiments according to the present disclosure make use of trigger-based sensor networks and trigger-based support networks that may be tuned or modified so as to collect data potentially related to one or more particular addiction triggers, such as Anger, Frustration, Noise, Social Situations, Stress, Yelling, etc. Such data solely or in combination can identify various high risk (of addiction usage) contexts or relapse situations, circumstances, events, and/or possible mental frame-of-mind/ thought processes that often have to be managed to allow the addict the ability to successfully deal with such situations without succumbing to the addiction(s). This managing of such situations may include providing, recommending, and/ or injecting actions, activities, resources, recommendations, directions, and/or elements of control into the addict's life on either an ad-hoc, occasional, periodic, and/or (near) continuous manner to help the addict to refrain from their addiction. Management of such situations can be done via a variety of analysis, assessment, and prediction engines and algorithms that anticipate or predict the impact of certain situations, contexts, circumstances, or events on an addict's behavior and overall sobriety and devise and quickly put in place a course of action to minimize the addict's risk of relapse, or failing that, minimizing any resultant harm and damage. Such a course of action may be predominately location-based, meaning using location information as a key part of the course of action, but the present disclosure is not limited to location-based information; key information may well include non-location based elements, particularly the use of sensors that can provide valuable input into understanding the current context of the addict, and actions that may have little or nothing to do with an addict's location (such as the addict calling a family member to discuss his Frustration, for example).

While various aspects of exemplary embodiments of the present disclosure are targeted at the treatment of addiction, actual addiction is not always involved. As noted before, exemplary embodiments of the present disclosure can be used for the prevention of addiction, dealing with possible or actual use or misuse of substances and/or activities that can potential be harmful to individuals or groups, or indeed unrelated to any addiction or substance/activity use/misuse at all. In order to utilize and receive the benefits of exemplary embodiments of the present disclosure, a person does not necessarily have to be an addict with an addiction to a substance and/or activity. For example, a person may want to cut back on drinking, for example, even if not physically addicted thereto or even if the person does not drink often. Treatment may refer to any assistance provided in various exemplary embodiments to help an addict and/or others in dealing with the addiction (as described broadly herein) in some form or fashion, and/or for informational purposes. Sober may refer to non-usage of the addiction substance/ activity. Relapse may refer to usage of the addiction substance/activity.

Exemplary embodiments of the present disclosure may also be applicable to persons and/or situations in a pre-addiction situation or scenario where the substances/activities are merely abused, that is, done more or more often than might be considered acceptable, healthy, or desirable. Thus, various embodiments of the present disclosure may be applicable in relation to persons who may be considered high-risk, such as the children of alcoholics, though no symptoms of addiction exist. Various embodiments of the present disclosure further may be applicable in relation to situations and/or scenarios where person(s) are neither addicted nor considered abuser(s) nor high-risk; rather, they and/or others would like to reduce the usage of a substance or activity to achieve some real or perceived benefit. The above situations/scenarios and other applicable contexts may be generally included under the term addiction, and a person suffering from addiction, abuse, or the general desire to reduce/stop doing some substance and/or activity may also be referred to as an addict. Also, an addiction or addict is not limited to just one substance or activity; many addicts concurrently or serially suffer from more than one addiction (sometimes referred to as dual diagnosis, though it can actually be 2 or more addictions). Various embodiments of the present disclosure can be equally applicable to such persons with multiple addictions, either concurrent or consecutive.

In addition, a distinct set of exemplary embodiments related to prisoner and particularly parolee tracking and monitoring is enabled by the present disclosure. Such tracking and monitoring is currently done by a GPS bracelet attached to the person's ankle or other body part, with their movements then monitored via GPS readings. In situations where GPS does not work or work well, particularly in a building or other structure or environment where GPS does not work, cell tower triangulation is employed to provide a rough calculation. Both have limitations: GPS with its primary use cases of being tracked outdoors, and the inaccuracies associated with cell tower triangulation for indoor situations.

Because of these limitations, GPS bracelets in effect determine the type of prisoner/parolee tracking that can be done, limiting the person to a particular area or building. It cannot get more "micro" than that and/or cannot granularly track the person's location and activities in an indoor environment, which is, however, possible with exemplary embodiments of the present disclosure. For example, a parolee could be confined to house arrest in a multi-unit apartment or motel due to the enhanced ability to track a person's movements indoors. In addition, activities can be monitored or controlled, such as a person on parole for a DUI (Driving Under the Influence) being prohibited from drinking. The sensors associated with the present disclosure as well as risk calculation algorithms could be used to detect high risk situations where the parolee is about to violate parole, generating various alarms. If the parolee followed through and drank, then exemplary embodiments of the present disclosure would provide the evidence needed to revoke parole.

Context may generally refer to an addict's situation, environment, and/or state-of-mind (e.g., as determined by biometric data, etc.) particularly as it relates to a potential substance abuse relapse. Traditionally in mobile systems, a person's physical location can form a key cornerstone of that person's context—and indeed may be all that is needed to determine the person's overall context in many instances. For example, if an alcoholic has stopped at a bar on his way home from work, it typically takes no additional data to infer a high-risk relapse situation and state-of-mind. However, other or additional sensors may be used to confirm and/or refine a person's context. For instance, a light sensor on an addict's device may indicate that the person is still outdoors (perhaps debating himself in the parking lot). A breathalyzer sensor could indicate a relapse—that the situation has moved from needing a prevention set of actions to a set of damage control and safety actions. Thus, an addict's location may be considered the entirety of the context (stopped at a bar), part of the context (not yet in the bar), or perhaps even not a key part of the context (e.g., the person is drinking or is drunk, having left the bar, etc.). However, for many if not most embodiments, physical location plays at least a partial role in determining a person's overall context; in addition, the location of support resources very often plays a key role in if and/or how such resources may be employed.

In various exemplary embodiments of the present disclosure, systems and methods are provided for preempting, anticipating, and/or detecting high risk addiction relapse situations and determining and implementing actions and activities to prevent a relapse from occurring, or in the case of actual relapse minimizing the associated damage and returning the addict to sobriety as soon as possible. Various mechanisms are provided for determining and utilizing an addict's context—particularly location—in assessing their risk of relapse, and utilize that context as well as the relative locations and contexts of other resources to determine and implement relapse preventative actions. In various exemplary embodiments of the present disclosure, location/context-based mechanisms are provided to minimize or contain the consequences in the event that a relapse occurs, as well as mechanisms to preempt and prevent high risk situations from occurring At a more granular level, an example communications network includes a plurality of heterogeneous, differing, or different types of sensing devices configured to monitor the location and/or context of an addict; and a plurality of heterogeneous, differing, or different types of interface devices each configured to engage in interaction with the addict, with a support person for the addict, and/or with a third party in the event that the network detects a relationship between the monitored location and/or context and a trigger predetermined in the network for the addict as being related to relapse; wherein the interaction is selected based on the trigger and the monitored location and/or context.

The example communications network may include one or more server, client, cloud, peer-to-peer, and/or other devices configured to develop and/or update a profile of the addict based on monitoring data from the sensing devices and/or the interaction engaged in by one or more of the interface devices.

In the above example communications network, one or more of the sensing devices may be configured to detect and/or determine the relationship between the trigger and the monitored location and/or context.

In the above example communications network, the sensing devices may be located in, on, and/or near the addict, and/or elsewhere relevant to a current and/or future location/context of the addict.

In various aspects of the present disclosure, a network-implemented method of providing support for an addict includes monitoring the location and/or context of the addict, the monitoring performed by one or more sensing devices; detecting a relationship between the monitored location and/or context and a trigger predetermined in the network for the addict as being related to relapse; and based on the detected relationship, one or more of a plurality of interface devices of the network interacting with the addict, with a support person for the addict, and/or with a third party.

The foregoing example method may include, based on the monitoring, the detecting, the determining, and/or the interacting, developing and/or updating a profile of the addict, the profile including actions to take in relation to the addict.

In the foregoing example method, one of the sensing devices may be configured to send the monitored location and/or context and/or the detected relationship to one or more other devices of the network.

In the foregoing example method, the sensing devices may be one or more of the following: located in, on, and/or in the vicinity of the addict, mobile, and stationary.

Figure 1:
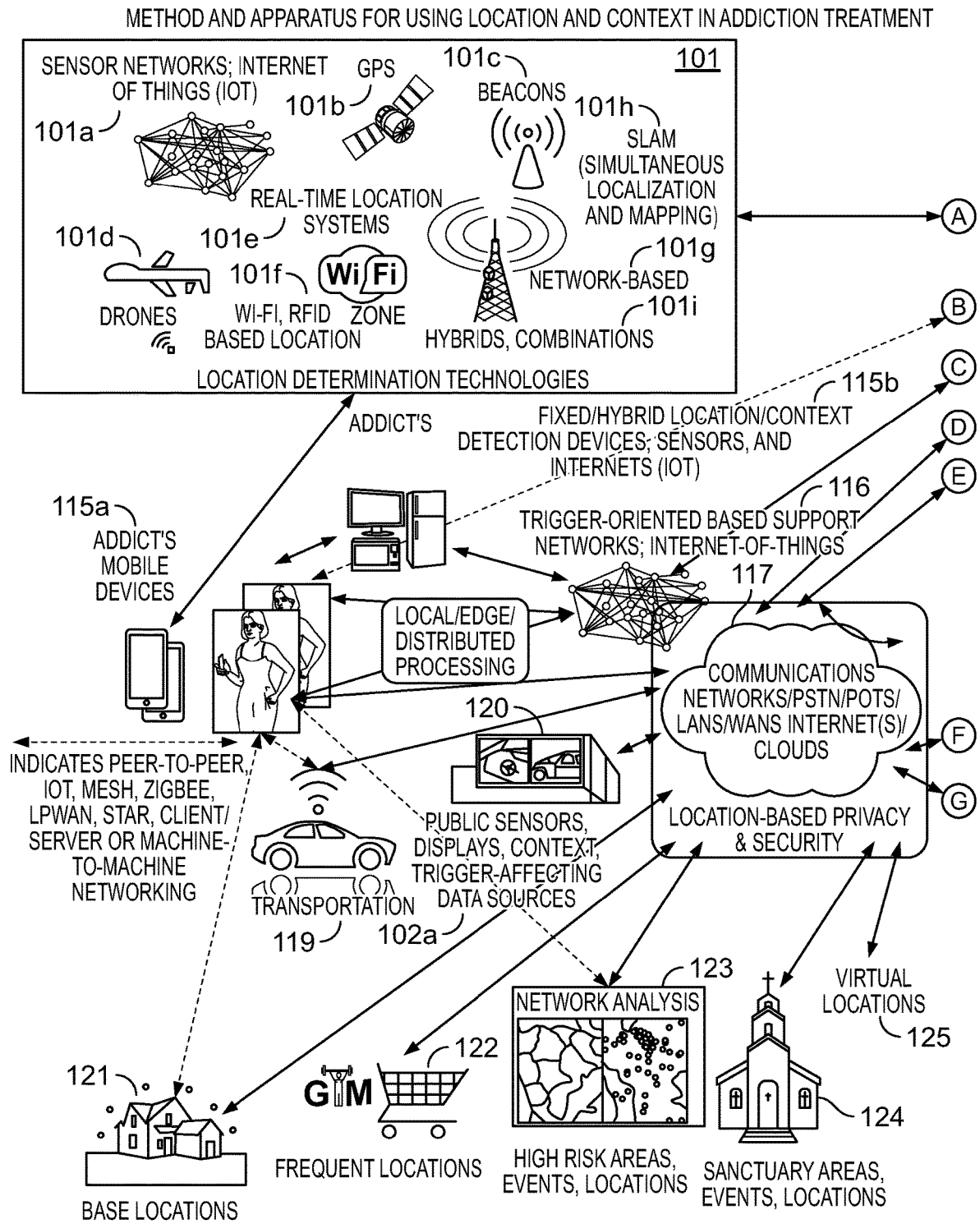
Figure 1:
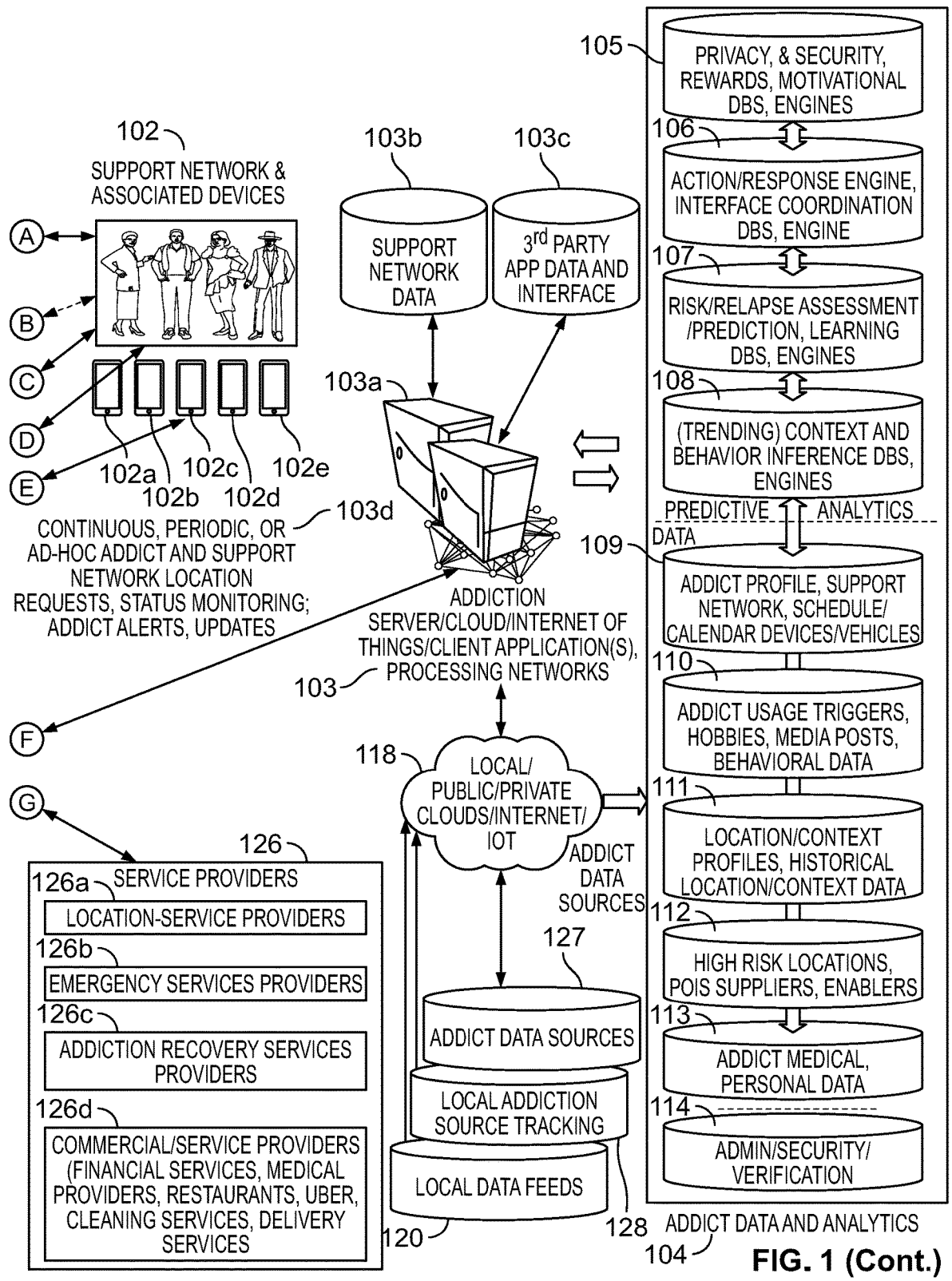

FIG. 1 is a high-level summary diagram that shows an addict with associated devices, sensors, wearable/embedded tags, and other locatable technology. FIG. 1 also shows an exemplary scope of potential people, resources, assets, locations, applications, and data that may be helpful and/or important in helping the addict become and stay sober. Associated devices generally refers to any technology that may be directly or indirectly associated with the addict for collecting data on or about the addict and/or for disseminating data or actions to or about the addict. Thus, an addict does not have to be in physical contact with a device for a given exemplary embodiment to work. For example, an associated device could be the use of a drone to shadow an addict's movements, location, and behavior and reporting that information back to analytical engine(s) of the given embodiment. The scope of potential resources is not limited to those listed in FIG. 1 as other resources may be used in other exemplary embodiments.

FIG. 1 illustrates various example embodiments 100 of the present disclosure including the use of an addict's support network 102. A support network is generally considered people who have some knowledge of and/or influence about the addict's problems and are prepared to help. The support network 102 of people may include medical professionals, friends, family members, therapists, co-workers, spouses/partners, social workers, advocates, pastors, priests, rehab/treatment centers, emergency responders, lawyers, courts, parole officers, social/business networks, family support networks, specialized social media (Addiction, Trigger-Focused) support, other websites, internet/cloud help, addiction community members, other addicts (using, recovering) or anyone who might be aware of the addict's situation and in a position (including physical location) to assist the addict in some form if the need arises (e.g., a support person, etc.).

Various example embodiments of the present disclosure provide for continuous, periodic, ad-hoc, and/or as-needed monitoring 103*d* of the support person's location and/or status for potentially helping one or more addict's, such as but not limited to Busy, Work, Available, In Emergency, Please Find Someone For Me To Help (e.g., assist anyone, not just the persons listed as approved assisters), and/or schedule/calendar for one or more of those support persons and associated respective statuses. This monitoring could be initiated by the Addiction Server, by the support person's device(s) 102*a*, 102*b*, 102*c*, 102*d*, 102*e*, cloud-based services, and/or 3rd party applications that already make use of location and/or status monitoring.

While FIG. 1 shows a variety of networking and communications technologies, systems, and architectures, such as wireless communications, client-server, peer-to-peer, and cloud computing, the present disclosure is not limited to these. For example, an architecture may be deployed that deploys disclosed functionality for a very limited area for a select type of receiver/person for a limited period of time, such as spontaneous, unscheduled, or flash (short-notice) drinking trigger meeting (a kind of specialized Alcoholics Anonymous meeting). Some or all of these attendees might have a specially issued RFID-type (printable, downloadable, or temporarily/specialty activated) tag, and/or beacon-based network that allows them access to the meeting and interfaces with other personal technology that enables them to enjoy benefits from the meeting, such as personalized holographic presentations to their personal visor, specialized drug doses, or just validation of their identity. Addiction FOB or dongle-type devices might also be used that serve as the interface means between such meeting technology and other personal technology such as a wearables or implantable, or the Addiction Monitor/Controller device 200 shown in FIG. 2.

FIG. 1 also discloses an example Addiction Server/Cloud/Internet of Things/Client Application(s) and Processing Networks 103 (server 103*a*) that can be a key hub for communications with a variety of people 102, resources, assets, applications, and data sources that may have relevance to the addict. As shown, the data sources may include a database 103*b* of support network data (e.g., location, availability/schedule, specialties, privacy requirements or regulations, etc.) and a database 103*c* of third party app data and interfaces (e.g., social medial, local search, navigation, etc.) and affinity programs. The data sources may also include data sources accessible over a network 118 (e.g., local network, public network, private network, internet, IOT, etc.) such as a database 127 of addict data (e.g., medical, professional, public records, media, etc.), a database 128 of local addiction data (e.g., police reports, trends, etc.) and a database 129 of local data feeds (e.g., events, traffic, news, weather, camera feeds, etc.). Additional data sources may include addict data sources including addict data and analytics 104, including predictive analytics data, etc. The addict data and analytics 104 may include privacy, security, rewards, motivational database(s) and engine(s) 105, action/response engine, interface coordination database(s) and engine(s) 106, risk/relapse assessment/prediction, learning database(s) and engine(s) 107, (trending) context and behavior inference database(s) and engine(s) 108, addict profile, support network, schedule/calendar, devices/vehicles 109, addict usage triggers, hobbies, media posts, behavioral data 110, location/context profiles, historical location/context data 111, high risk locations, places of interests (POIs) suppliers, enablers 112, addict medical, personal data 113, and administration, security, and verification 114.

The server 103*a* also serves as the primary analytical engine for developing and processing algorithms for profiling an addict's behavior, tendencies, risks, and probabilities of relapse for a wide range of possible situations, and for determining a variety of actions to, for, or on behalf of the addict to avoid relapse and/or improve the addict's overall treatment. Included in potential actions are monitoring the location of the addict and the addict's support network for scenarios where one or more support persons may be dispatched to the addict's location, or vice versa.

Such server functionality can be physically and/or logically configured in many forms. It can be centralized in one or more servers. It can be partitioned in a centralized manner such that functionality is split among different servers, such as one server being a communications network front-end for communicating with various addicts, devices, sensors, and other networks, while another server or set of servers does the analysis of the data. It can also be architected in distributed manner such that some or all of the functionality is performed on addict and/or support network devices. It can be architected such that some or all of the functionality is done in the Cloud via various forms of cloud computing. Regardless of physical and/or logical distribution of functionality, it may be described as or referred to as a server unless otherwise indicated.

The server serves as a monitoring, assessing, and controlling function of, for, and/or on behalf of the addict. This could include providing a variety of alerts to various resources that the addict is in a high-risk situation or area. This control could further extend to actions such as disabling the addict's car, informing the addict's addiction sponsor or community members, or alerting family or law enforcement about dangerous situations. Indeed, one example embodiment of the present disclosure provides a form of involuntary monitoring and action coordination, not unlike GPS ankle bracelet monitoring, where an addict on parole for addiction-related offenses (e.g., DUIs, etc.) may have their devices (and even attached sensors such as Blood Alcohol Content sensors) monitored to detect the presence of offending substances, and implementing actions to mitigate the risk to the community and the addict themselves.

Another aspect of exemplary embodiments of the present disclosure is the use of multiple location determination technologies or sources 101 to determine locations of addicts and other persons/places/things. These technologies or sources 101 include, but are not limited to, sensor networks (e.g., Internet of Things (IOT) 101*a*, etc.), GPS/Assisted GPS 101*b*, cell tower identification 101*g*, cell tower triangulation (TDOA, AFLT), beacons 101*c*, Radio Frequency fingerprinting, Real-Time Location Services (RTLS) 101*e*, Wi-Fi based location systems 101*f*, Radio Frequency Identification (RFID) based location systems and similar systems, drones 101*d*, crowdsourcing, hybrids 101*i*, simultaneous localization and mapping (SLAM) 101*h*, and/or combinations of these or other location determination systems. These location determination systems may be on, worn or carried by, used by, embedded in, or nearby the addict or addiction-related resource sufficiently to determine approximate location.

Not all aspects of the present disclosure need to be centralized in the addiction server. The addict's local device(s) 115*a* may also have functionality as disclosed herein, both for Peer-to-Peer, IoT, Mesh, ZigBee, LPWAN, Star, Client/Server, and/or machine-to-machine (M2M) networking, situations and in circumstances where the addiction server or other parts of the present disclosure are not operating or accessible. An example of this functionality is in the device on/in/around the addict detecting a high-risk situation and the addict attempting to enter and drive a car in an underground garage (thereby preventing a GPS locate). The addict's device would automatically connect with the vehicle's transportation system 119 (e.g., personal vehicle, friend or colleague's vehicle, transportation service like Uber, airlines, public transportions, etc.) to inform or provide an alert of a high-risk situation and proceeding to disable the car. Indeed, many, even all of the server's functions could conceivably be done in one or more of the addict's device(s) or in other computing/data processing architectures such as cloud computing; a centralized server is a convenient/logical way to represent many of the present disclosure's functions, but not inherently necessary to its overall functionality. For example, the risk/prediction engine part of the server could easily be resident on the addict's device(s)(client). Indeed, in one exemplary embodiment, many or even all functions could be resident and/or controlled on the client.

Similarly, not all devices that can be used are depicted in FIG. 1. Devices 115*a* that can be associated with the addict include but are not limited to portable devices such as mobile phones/smartphones, tablets, laptops, other portable or mobile devices, etc.; wearable devices and tags on or in clothing, jewelry, shoes, watches, etc.; mobile payment devices/wallets, etc.; embedded sensors, tags, chips or other electronics that can be implanted or ingested (e.g., ingestibles or implantables, etc.) in an addict, augmented reality and heads-up-displays (e.g., Google Glass, etc.) and virtual reality-enabling systems. Fixed or mobile/fixed hybrid devices 115*b* such as desktop computers and smart home connected devices that can also be associated with the identity and/or location addict are also part of aspects of some exemplary embodiments of the present disclosure. For example, FIG. 1 shows additional examples of smart home connected devices 115*b* including a TV, refrigerator, and microwave. As more and more devices become smart, the smart device will have the ability to capture data that will help determine a person's location/context through onboard or connected data capture devices such as video, audio, and/or other sensors. Combined with the device's known location (or ability to determine the device's location), and the connectivity associated with communicating to and from these devices (also known as the Internet of Things or IoT), these devices/networks may provide new key sources of personal context information.

FIG. 1 also discloses a variety of location and categories useful in a wide variety of embodiments, not limited to the addict, support resources, or even enforcement resources. One key concept can be to utilize these varieties of location types and categories in a variety of ways in supporting the above resources. These include, but are not limited to:

Base Locations 121 including common locations for the addict, such as home, work, school, or church, etc.;

Frequent Locations 122 including locations frequented often by the addict, such as homes of friends or family, stores, restaurants, malls, gym, hobbies, etc.;

High Risk Areas, Events, Locations 123, such as liquor stores, casinos, concerts, drug-dealing areas that could pose a temptation for the addict, bad peers, trigger activating situations, etc.

Sanctuary Areas, Events, Locations 124 where an addict might feel safe and have a very low temptation to use, such as AA meetings, churches, key/safe friends and family members, dry public areas or events;

Virtual Locations 125 including online forums, such as Facebook, Twitter, Women for Sobriety, therapy sites/sessions, Virtual Reality Locations, addiction communities where an addict can involve him or herself safely (without using) in an online activity. This includes the use of virtual and/or augmented reality to put oneself in a different (safer) location, context, and/or frame-of-mind.

While location is most often a key distinguishing characteristic, context can also be important, particularly for support network members. Just having a support person nearby in time of trouble is not enough, the person needs to be available, interested, and in a position (e.g., situation/context) that he/she can break away from whatever they are doing to help the addict. Thus context-determining sensors and other mechanisms can be important not only to the addict but the support network as well.

Put another way, Base Locations are where the addict is frequently, such as Home, Work, or School. Frequent Locations are where the addict frequently visits such as family and friends, the addict's gym, frequently visited stores or restaurants, and various hobby locations such as a bowling alley. High-Risk Locations are another element used in various embodiments, to track possible high-risk areas for the addict with both fixed locations (such as liquor stores, casinos) and varying locations (such as recent drug-activity areas). Opposite these high-risk locations would be Sanctuary Locations, where the addict will presumably be especially safe from high-risk situations, such as an AA meeting or church service. The use of Virtual Locations is also disclosed, used when an addict is logged into and/or viewing a service like Facebook or Twitter or is using Virtual Reality devices such that the addict is on those applications and can be contacted or otherwise influenced by those applications.

These location categories have a wide range of uses. They can be an integral part of action determination when relapse risk is high, by finding the closest Sanctuary Location, for example, and arranging for a nearby support person to meet the addict there, including providing each of them directions via their navigation application based on their current location. High-risk locations of course are to be avoided, but this can be done in many ways. They can be omitted from navigation applications (de-augmented) to prevent temptations. Geo-fences can be setup around them such that when the addict enters one automatic alerts are sent to nearby support persons to give them a heads up to possibly prepare for an interception. Indeed, geo-fences can play an important role in various embodiments, e.g., in risk prediction (e.g., if a high-risk location geo-fence is violated then risk score goes up by 20%, etc.), support resource identification (alert people within 10 miles of the addict when X occurs), and context setting (e.g., locations with walking distance of home-half a mile—are considered safe/home location), etc. If an addict is within 1000 feet/5 minutes of a park, then a walking/running excursion can be added to a list of potential actions. And so on. Virtual locations can also have a wide range of uses, e.g., special Reddit groups, as could quasi virtual/physical locations such as safe zones for Anxiety sufferers within the broadcasting distance of a coffee-shop beacon, that provides for virtual or physical meetings of sufferers only within range of the beacon.

Figure 2:
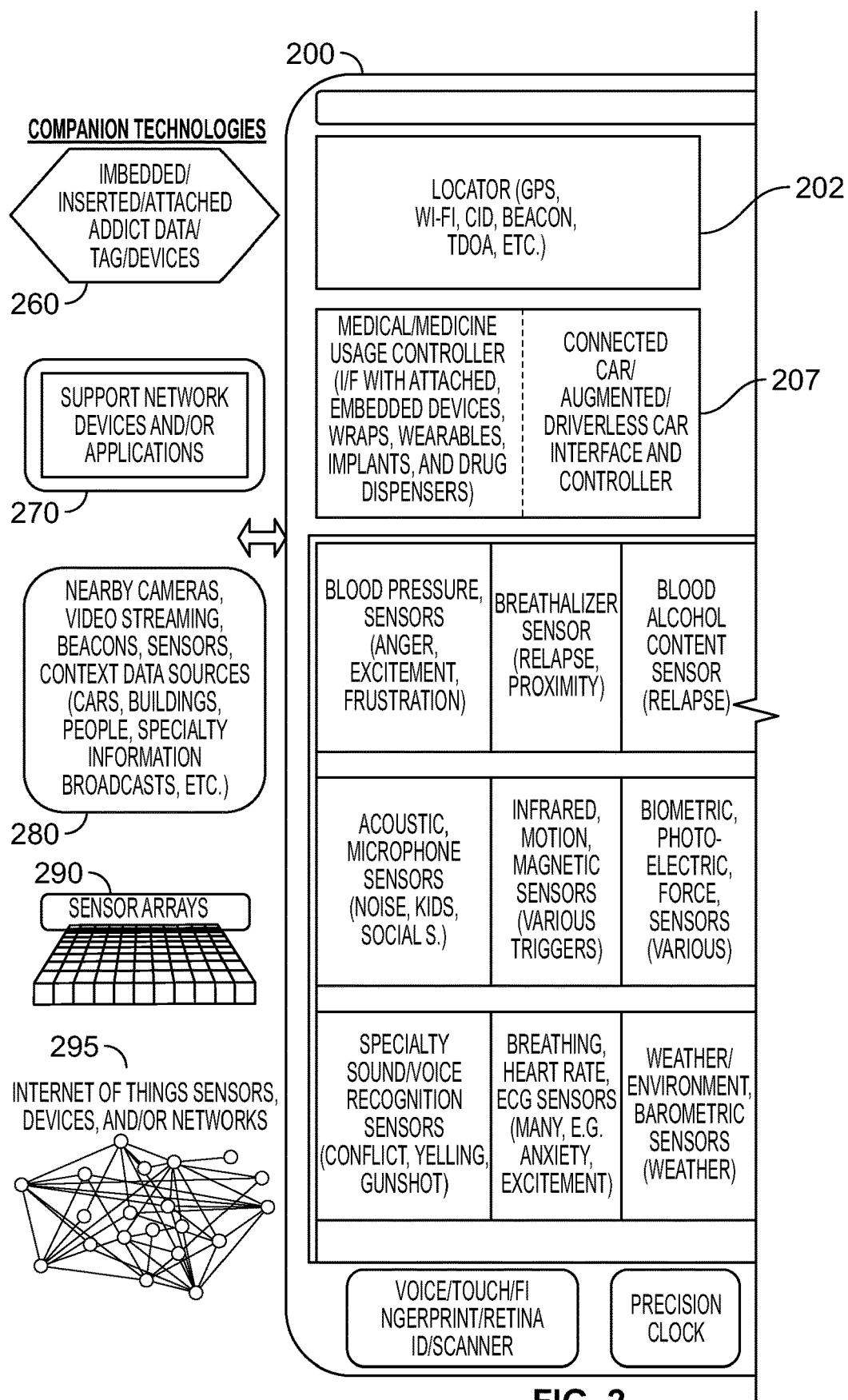
Figure 2:
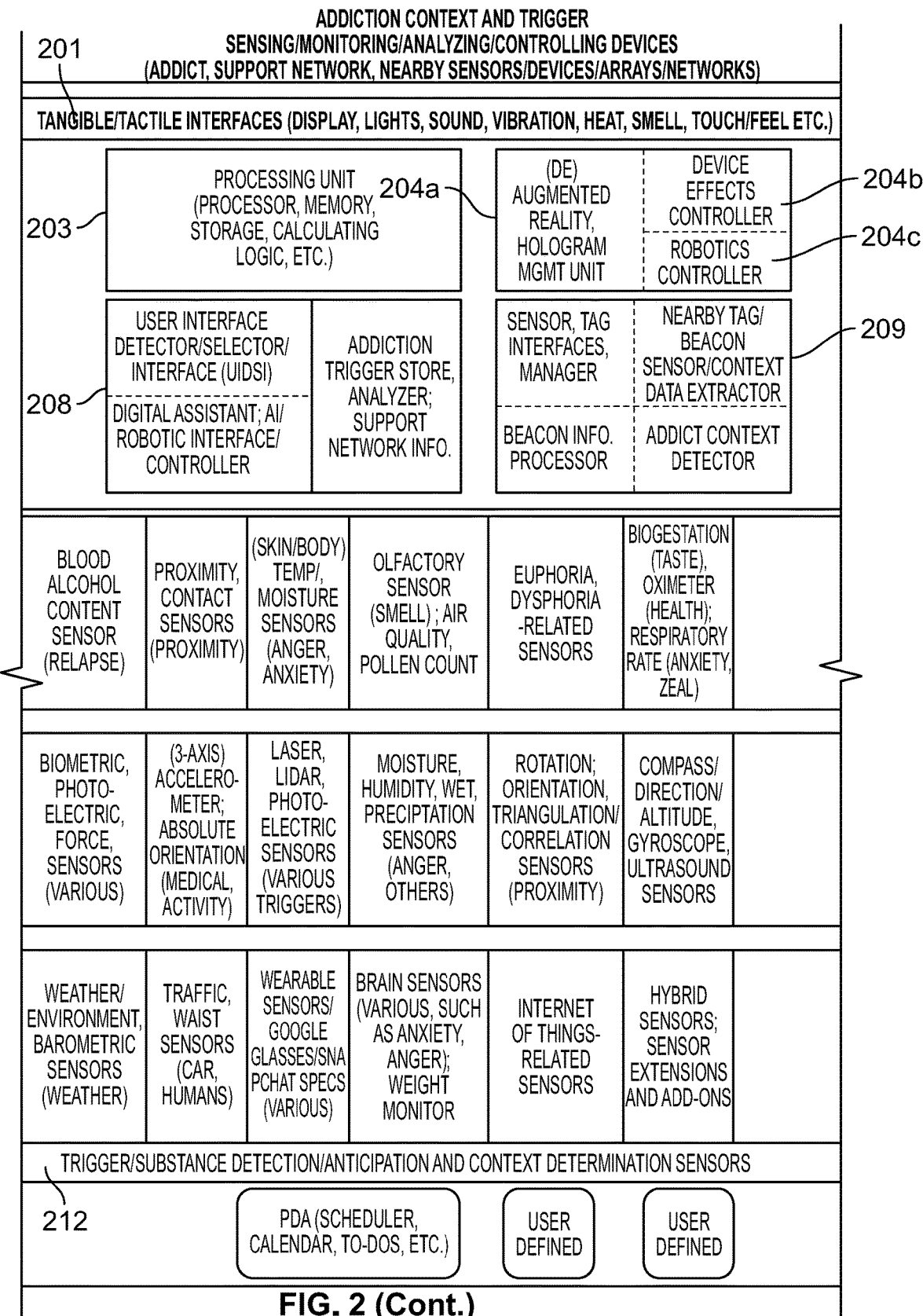
Figure 2:
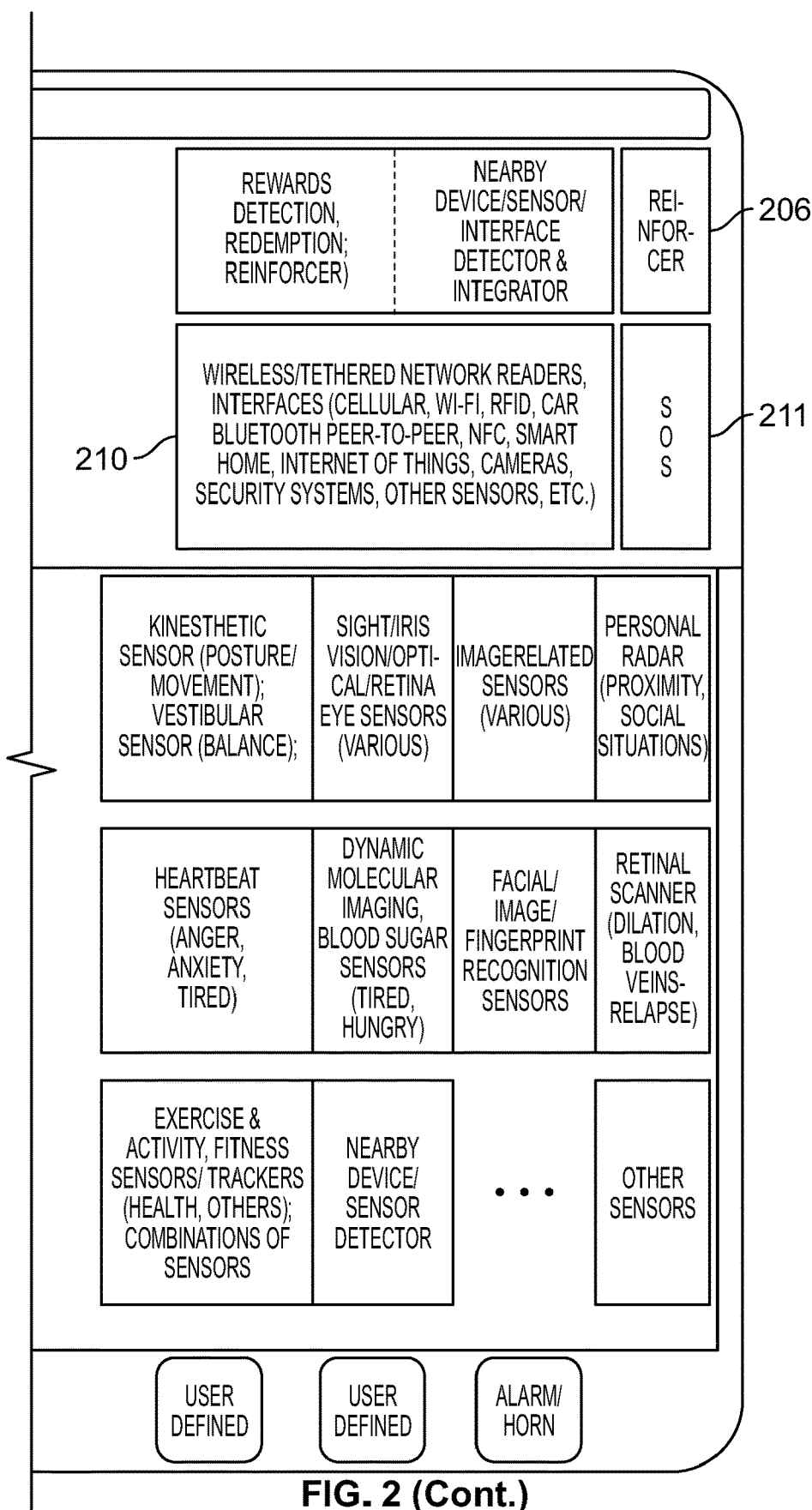

In various embodiments, a variety of sensors, devices, and mechanism, may be used to determine the location and particularly the context of the addict. FIG. 2, for example, describes a device 200 an addict might have on their person (e.g., a smartphone, etc.), wear (e.g., in the form of a watch), have implanted, or otherwise be on or near an addict. This device 200 could contain a variety of sensors 212, such as sensors that detect and capture sounds, images, video, or body conditions, for example. FIG. 2 provides a detailed (but not exhaustive) list of such sensors 212, including Blood Pressure sensors, Breathalyzers, Blood Alcohol Content sensors, Environmental/Weather sensors, Skin Temperature sensors, Olfactory (smell) sensors, Bio/gestation sensors, Vestibular sensors, Kinesthetic sensors, and Sight/Vision/Optical sensors to name a few. Other sensors may also be used including sensors for Water Quality/Pressure, Chemical/Gas/Fire/Smoke/CO2/Flood, Level, Gyroscope, (Passive) Infrared, Eddy current, contact, Ultrasonic, Images, Alarm, Doppler; Fiber Optic, Occupancy, Reed, Touch Switch, Magnetic, Inductive, Microwave, Radiation, Parking, etc.

The use of these various sensors can be to aid in the detection and/or determination of the addict's context, e.g., what the addict is experiencing, feeling, even thinking, etc. Even further, to the extent possible individually or in combination with other sensors and/or data, the goal of such sensor use can be to detect/determine what trigger(s) the addict may be experiencing, and to what degree, in order to gauge the risk of relapse and factors involved in the potential relapse, and to identify and set in movement a course of actions that will preempt or prevent an addict's environment from deteriorating to the point of relapse.

FIG. 2 discloses one such device(s) 200 that can sense, monitor, and/or control aspects of an addict's context. The device 200 includes an array of capabilities, including sensors for detecting or anticipating addiction trigger conditions (e.g., contexts, situations, circumstances, environments, and/or state of mind(s) that may cause the addict to relapse or use substances or activities related to his/her addiction, etc.); mechanisms for interfacing with the addict including tangible/tactile Interfaces 201 (Display, Lights, Sound, Vibration, Heat, Smell, etc.). For example, a Smell Interface could generate the smell of fresh pine trees or pine tar in response to high risk associated with the Escape trigger being detected (helping remind the addict of good times he has had when hiking in the Rocky Mountains). The wide variety of interfaces is premised that dissemination of information to/from an addict needs to be in the most effective means possible at any given time or context, which can vary from day-to-day or hour-to-hour. In addition to traditional interfaces such as sound or vibration interfaces, some exemplary embodiments of the present disclosure include the ability to project (or interface to a projector) 2 or 3 dimensional images, video, GIFs, or real-time holographic projections that the addict can converse with. It also includes the ability to augment reality (insertion of images not actually present), and even (de) augmenting reality, such as the elimination of addiction triggers/temptations such as liquor stores from the addict's vision.

FIG. 2 depicts a partial list of a variety of sensors that can be used to determine the addict's context. These sensors can be used individually, in combination, and/or with other information about the addict, environment, situation, circumstance to determine the addict's context, as well as determine if there are any triggers being activated or in the process of doing so. Simple examples include using acoustic sensors to detect the volumes and type of sounds in an addict's vicinity, to potentially identify triggers such as Noise (e.g., too high or low volume, etc.), Children (e.g., detecting high-pitched voices and/or multiple children, etc.), or Social Situations (e.g., multiple voices in the background, etc.).

The addict's device 200 shown in FIG. 2 may be configured to serve as a local controller of information of, in, and around the addict. Towards that end it is, to the extent possible, self-reliant and contained in how it collects, processes, and disseminates data-based and physically-based actions. To begin with, it provides a set of tangible/tactile interfaces for interacting with the addict, under the assumption that having good preventative actions is only part of the battle-such actions must be presented in a manner acceptable/receptive by the addict. Very often this is dependent on the context of the addict; for example, at night an addict may be most receptive to audio-based messages, while in the day he or she may be most receptive to visual-based actions. In public places the addict may not want either, but instead be physically pulsed/shocked/vibrated/or heated to remind them they are increasing their risk of relapse for example (one addiction reality is that many relapses are not deliberate, meaning they are a culmination of smaller, even innocent-seeming behaviors that rapidly culminate in a relapse situation before the addict was even aware they were in danger. Small shocks or other physical cues can help wake up the addict early in the process and stop the danger before it starts to build out-of-control).

The device 200 in FIG. 2 has a variety of capabilities to be self-sufficient and help monitor/manage/control the addict. The device 200 has a Locator Unit 202 that has or interfaces to a variety of location determination technologies (e.g., GPS, Wi-Fi, CID, Beacon, TDOA, etc.). The device 200 has at least one CPU 203 and associated memory, storage, and calculating circuitry, hardware and software, to do data collection, analysis, and decision making. The device 200 has specialty processing and display/interfacing capabilities for managing such capabilities as virtual reality, (de)augmentation, holograms 204a, device effects controller 204b, and robotics 204c. The device 200 has a mechanism 210 for detecting and interfacing with other nearby devices to extend its sensor/data collection capabilities (for example, tapping into a nearby security camera to see the addict's surrounding environment). The device 200 has an onboard medical controller 207 that can interface/integrate with attached and/or embedded devices or physical wraps, wearables, implants, and/or drug dispensers, in order to—if needed—suddenly inject or offer for immediate consumption an addiction treatment drug. The device 200 has a User Interface detector 208 that can tie into nearby systems if such systems are deemed advantageous for delivering a message (for example, broadcasting the message over a car's stereo system while it is playing a song (e.g., interrupting the song), instead of ineffectually playing on the addict's phone). The device 200 has a digital assistant and/or interface to a digital assistant for managing the addict's day-to-day, hour-to-hour schedule. The device has a self-contained module for storing and managing the addict's triggers (particularly useful if the addict is cut off from the broader system). The device has an onboard manager for all the myriad of sensors and tags on or nearby the addict so such data can be analyzed locally. Similarly, the device has a beacon interface/manager 209c to transmit/receive information from local beacons. More broadly, the device 200 has the capability of determining context locally, particularly in its ability 210 to tie into local networking connections such as Wi-Fi, RFID, RTLS, Bluetooth, peer-to-peer, Internet of Things, mesh/ZigBee, security systems, and other local-oriented networks. As shown in FIG. 2, the device 200 may be configured for connection and communication with companion technologies, such as imbedded/inserted/attached addict data/tag/devices 260, support network devices and/or applications 270, nearby cameras, video streaming, beacons, sensors, context data sources 280 (e.g., cars, buildings, people, specialty information broadcasts, etc.), sensor arrays 290, Internet of Things (IoT) sensors, devices, and/or networks 295 (also shown in FIG. 2*b*), etc.

Other capabilities include an SOS button 211 or similar mechanism that the addict can push/activate when he or she is feeling particularly vulnerable to relapse, which will in turn activate other portions, aspects or features disclosed herein. The device 200 also includes mechanisms for causing various levels of physical pain or discomfort (called a reinforcer 206) and/or pleasure, such as a sharp stinging sensation or warm/caressing sensation, which can be used to reinforce or dissuade certain behaviors, with the intention of preventing such behaviors and/or associating addiction-related behaviors or contexts with the pain or discomfort. The device also has a variety of identity verification/privacy protection mechanisms for protecting and if necessary disabling the device and preventing anyone from accessing the data on the device. There are also user-controllable/definable capabilities on the device, either programmable or insertable such as SIM-like add-on sensors.

The above does assume an all-in-one device for such capabilities. Such capabilities could be spread across multiple devices on and/or near the addict. Example of these device extensions are specialized addiction-related wearable and implantable devices that focus extensively or exclusively on detecting and reporting certain addiction-related conditions, not unlike today's Fitbit, such as bracelets that do double duty as a fashion accessory and blood pressure and skin temperature monitor. These readings could be prompted by and/or received by the Addict Monitor/Controller (AMC) shown in FIG. 2, or the extended device could do self-contained monitoring of those conditions and alert the AMC when they reach a concerning level. Smartphones with embedded alcohol detection sensors is another example. These addiction-specialty devices could continually monitor addiction-related conditions which could then send alerts and data (including location data) to the addiction server when conditions warrant. Such device extensions could include permanent devices not unlike today's parolee GPS monitoring ankle bracelets. A similar form could allow such actions as court-ordered alcohol use monitoring for DUI (Driving Under the Influence) offenders, or even voluntary usage by persons committed to beating their addiction but needing extra external discipline to achieve it.

In fact, the use in Parolee Tracking and Monitoring Systems is an exemplary embodiment of the present disclosure in at least two respects. The first addresses the limitation that current GPS-based ankle bracelets have in tracking and monitoring parolees and other prisoners, and that is its limited effectiveness inside a building. GPS does not work well inside buildings or in other contexts where there are obstructions between the bracelet and the GPS satellites, such as trees or metal containers, etc. Exemplary embodiments may utilize a variety of location-determination technologies and methods to monitor the location of the parolee. It then goes further to monitor the behavior of the parolee.

Of course, the devices and associated sensors and capabilities are only effective if they are actually powered on. It is an unfortunate fact of addiction life that many do not want to become sober, or at least feel they can be so without any outside help. In any event, it is assumed there will be the temptation to tamper with/otherwise disable such monitoring devices, and includes the ability to determine which addict-related devices are active (powered on and in the proximity of the addict) and which are the primary one(s) in use at an given place and time, via monitoring of usage as well as determining which device(s) are in the best position/proximity to monitor the addict's behavior, risks, and actions. This is important as well in general context determination, as people are trending towards having multiple devices, only some of which are actively on or near the person at any given time. In particular, it may be important to determine the primary device when determining what the best interface is for communicating with an addict at any given time.

The above capabilities can be packaged in a variety of form factors, ranging from being worn on the wrist or neck to glasses form to even implants. Form factors include but are not limited to: wrist/ankle devices, wearables, implantables (devices implanted/embedded in the skin/body), clothes, accessories, wallet, Google glasses, Snap spectacles, heads up display, augmented reality displays, inserts (e.g., ear), FOBs, key chains, are some of the form factors, Siri personal assistants (Built-In, Included, Add-on), smartphones, tablets, laptops, personal digital assistants, etc. The capabilities shown in FIG. 2 do not have to all be in one device, but can be spread across many different devices-even ones with no physical contact with the addict (such as security cameras, local RTLS beacons, etc.).

Figure 2A:
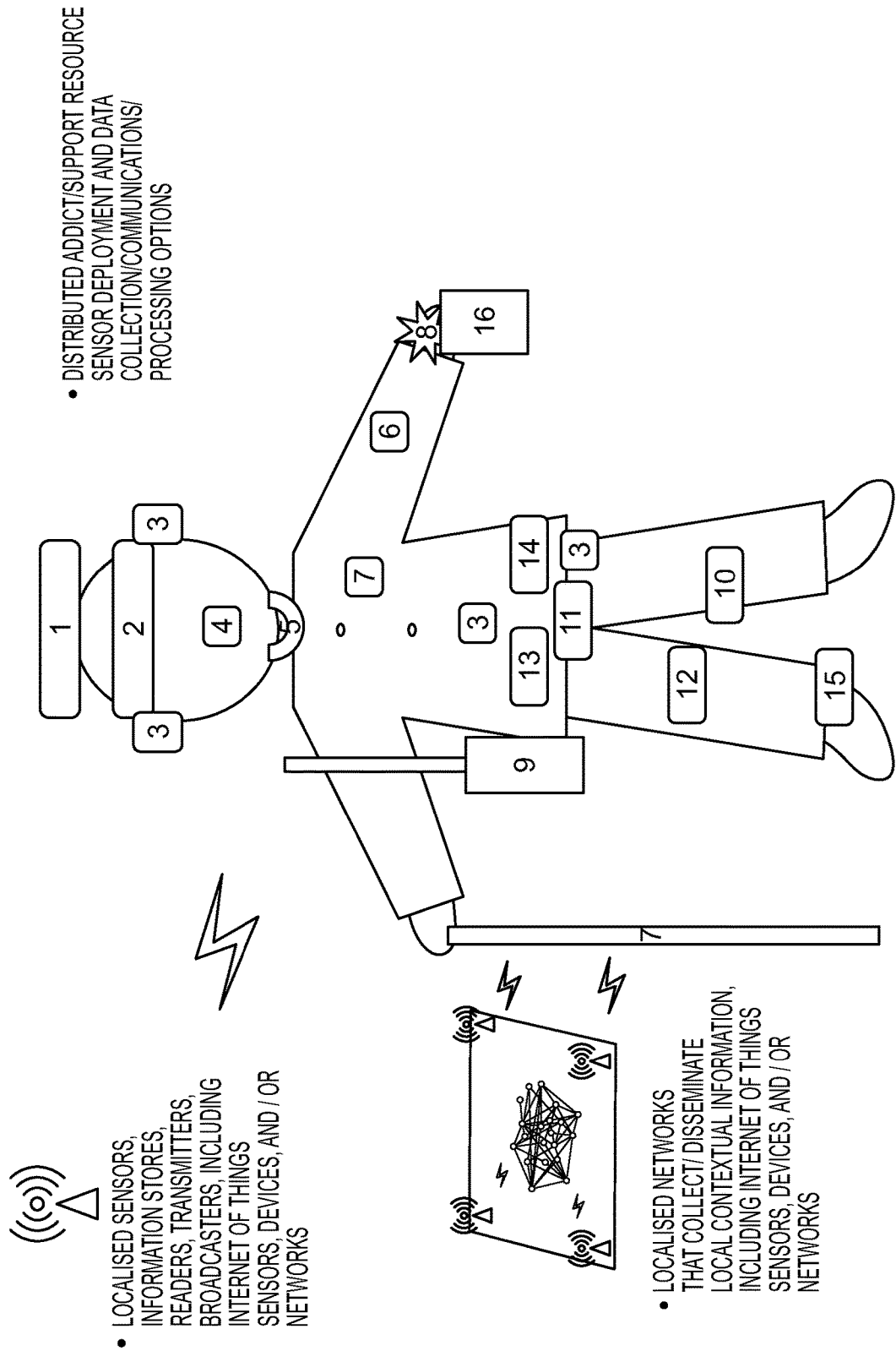

FIG. 2*a* provides examples of distributed sensor deployment, data collection options, localized sensors, and localized networks that may be used in exemplary embodiments. Form factor/sensor placement 1 may include a hat or headband. Form factor/sensor placement 2 may include glasses or a visor. Form factor/sensor placement 3 may include earplugs, earpieces, earrings, etc. Form factor/sensor placement 4 may include implants/inserts (e.g., teeth crown, pacemaker, ID chip, medicine deployment, etc.). Form factor/sensor placement 5 may include a necklace, piercings, nose rings, tattoos, etc. Form factor/sensor placement 6 may include a shirt, blouse, jacket, coat, etc. Form factor/sensor placement 7 may include accessories (e.g., pens, pocket protector, umbrella, cane, tools, touchpoints such as buttons and light switches, etc.). Form factor/sensor placement 8 may include a ring, bracelet, jewelry, etc. Form factor/sensor placement 9 may include a purse, briefcase, etc. Form factor/sensor placement 10 may include one or more sewn-in sensors, etc. Form factor/sensor placement 11 may include a zipper, belt, buttons, etc. Form factor/sensor placement 12 may include pants, a skirt, etc. Form factor/sensor placement 13 may include underwear (e.g., a bra, etc.). Form factor/sensor placement 4 may include a wallet including payment methods, etc. Form factor/sensor placement 15 may include shoes (e.g., a heel of a shoe, etc.). Form factor/sensor placement 16 may include a smartphone, tablet, laptop, PDA, FOB, key chains, etc. Included in the form factor/sensor placement may be the deployment/use of Artificial Intelligence (AI) assistants/Digital Personal Assistants such as Apple Siri, Amazon Alexa, etc. Sensors may be included/attached in such assistants. Conversely, AI assistance functionality may be embedded/attached to a variety of sensors and/or sensor form factors.

Also shown in FIG. 2*a* are localized Sensors, information stores, readers, transmitters, broadcasters (e.g., individual rooms, nearby persons, environmental sensors, etc.), Internet of Things (IoT) sensors, devices, and/or networks. FIG. 2*a* further shows localized networks that may collect/disseminate local contextual information (e.g., multiple rooms, malls, campuses, stores, schools, office buildings, etc.), Internet of Things (IoT) sensors, devices, and/or networks.

Figure 2B:
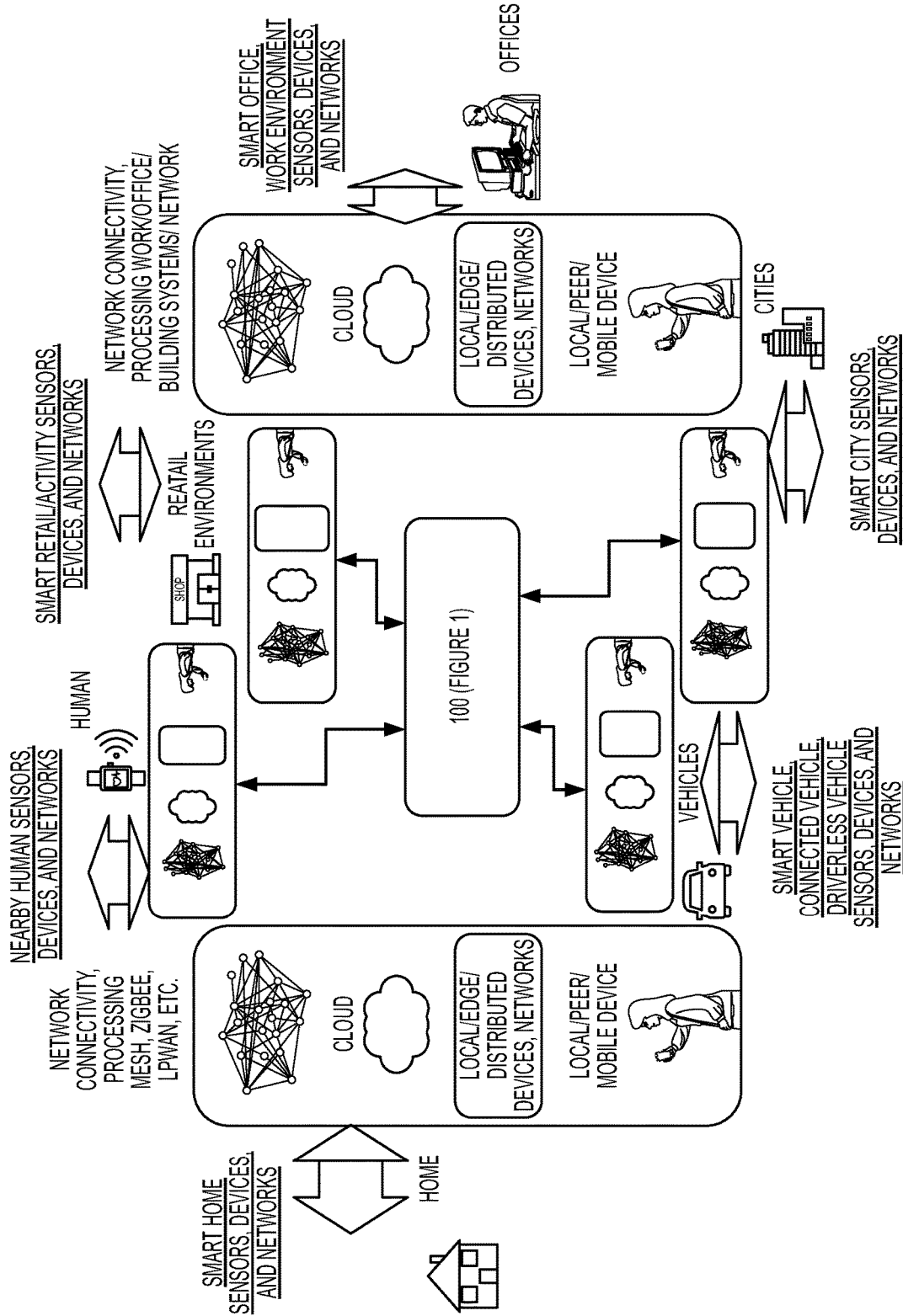

FIG. 2b provides examples of internet of things (IoT) addict-related sensors, devices, and networks 295 that may be used in exemplary embodiments. As shown, the IoT addict-related sensors, devices, and networks 295 may include smart home sensors, devices, and networks, such as home controllers, window/door, garage doors, HVAC, lighting, kitchen, security systems, appliances, computers and media, furniture, furnishings, media, landscaping, TV, decorations, rooms, pets, traps, fireplaces, etc.

The IoT addict-related sensors, devices, and networks 295 may include smart vehicle, connected vehicle, driverless vehicle sensors, devices, and networks, such as cars, trucks, aircraft, trains, boats, RVs/rec vehicles, etc. addict/support resources are using, in, within, or near—sensors, devices, and networks that provide location/context usage of such vehicles and directly or by inference usage and mindset of addict and/or support resources and activities to help detect, anticipate, prevent or mitigate high relapse risk situations, such as deactivating manual driving capabilities and activating driverless capabilities (e.g., for drunk drivers, etc.).

The IoT addict-related sensors, devices, and networks 295 may include nearby human sensors, devices, and networks, such as nearby (to the addict and/or support resource) person(s), devices, networks and sensors—including proximity and/or access to person(s) et al. and contextual data on, in or near that person as well as groups of persons and activities to help detect, anticipate, prevent or mitigate high relapse risk situations.

The IoT addict-related sensors, devices, and networks 295 may include smart retail/activity sensors, devices, and networks, such as restaurants, stores, banks/ATMs, arenas, gas stations, gym, parking, amusement, hospital, gym, etc.— places persons (addict and/or support resources) might shop or otherwise spend time in, including indicators of items being considered, purchased, and/or used (e.g., liquor, etc.) and activities to help detect, anticipate, prevent or mitigate high relapse risk situations.

The IoT addict-related sensors, devices, and networks 295 may include smart office, work environment sensors, devices, and networks, such as temperature, entry/exit, security, work-activity related, stress (mental or physical)-related, productivity-related, co-worker, office/work area-related (e.g., conference room lighting, temperature, A/C & Heating, Vending, Smoking machines, energy savings, bathroom, security cameras, lights, etc.).

The IoT addict-related sensors, devices, and networks 295 may include smart city sensors, devices, and networks, such as public spaces and infrastructure with associated sensors, devices, and/or networks (e.g., that addict/support resources, etc.) including parking, meters, advertising, police, first responders, etc.) that are in proximity of, connected to, and/or associated with that provide location/contextual information about addict, support resources, and activities to help detect, anticipate, prevent or mitigate high relapse risk situations.

Some exemplary embodiments of the present disclosure may include or involve the collection of large volumes of addict-related data, which is to be handled in terms of volume of data as well as the protection and security of that data and in particular the identity of the addict. The security and privacy of this data is protected in various embodiments, as the potential for abuse is huge given that in some instances an addict's location and context may be tracked nearly 24/7 at times. In addition, the social and professional stigma of addiction remains huge in our society, and many—even most—addicts greatly prefer their affliction remain private. Accordingly, a variety of systems and methods are provided for addressing such considerations, including but not limited to limiting the length of time data is stored, physically distributing the data among different databases including having location/super localized, context-specific, and/or trigger-specific data stores, invitation-only data access methods, time-limited networking, and encrypting and/or anonymizing such data so it is very difficult if not impossible to link addiction-related data to a specific addict identity. Such protections may include unusual protection mechanisms such as location selective availability coding (deliberately introducing errors into location calculations) or "nuclear football" keys where the codes for unlocking/decrypting data change daily and/or under physical protection (e.g., not stored where it can be hacked online).

Figure 3:
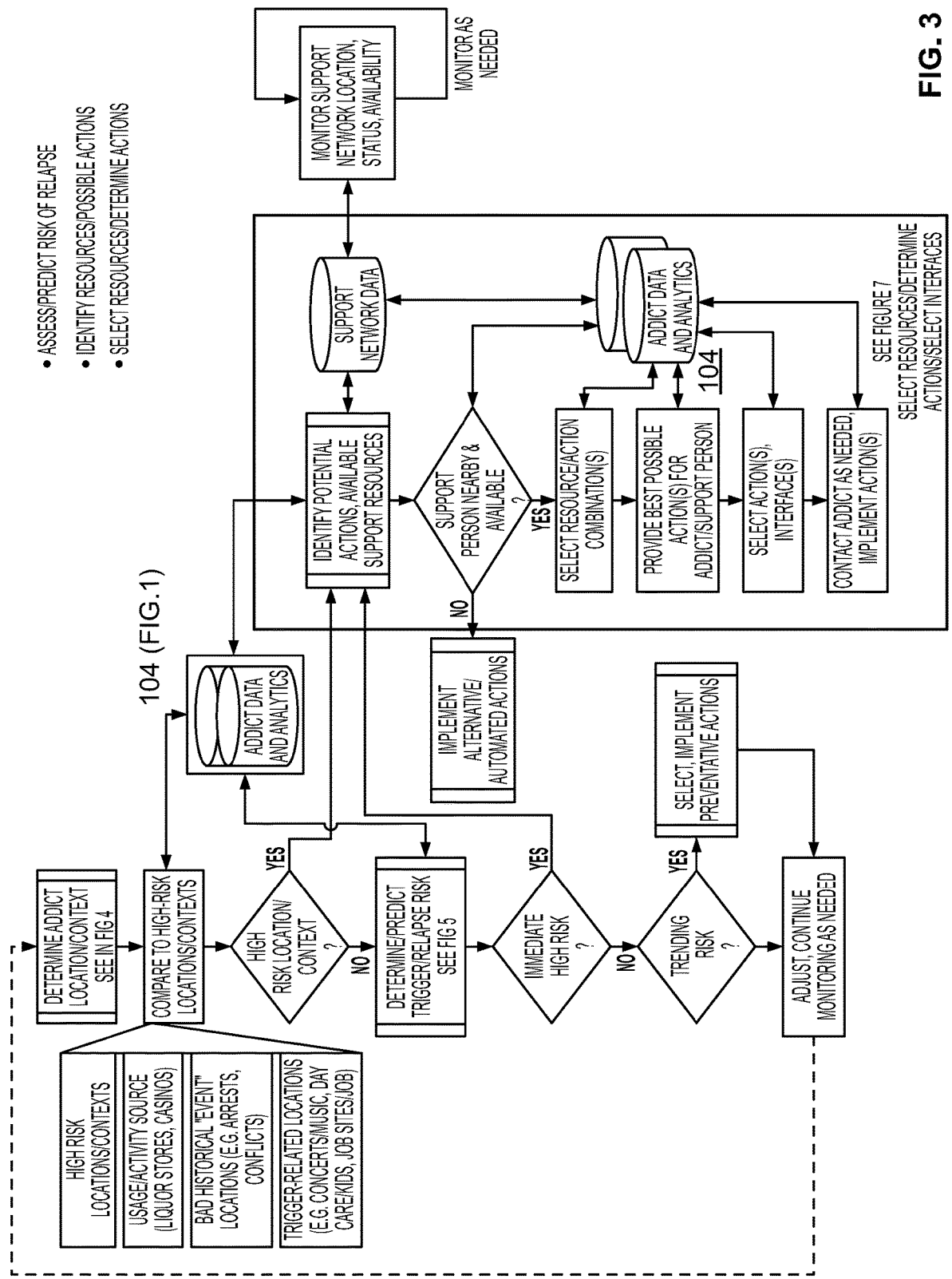
Figure 4:
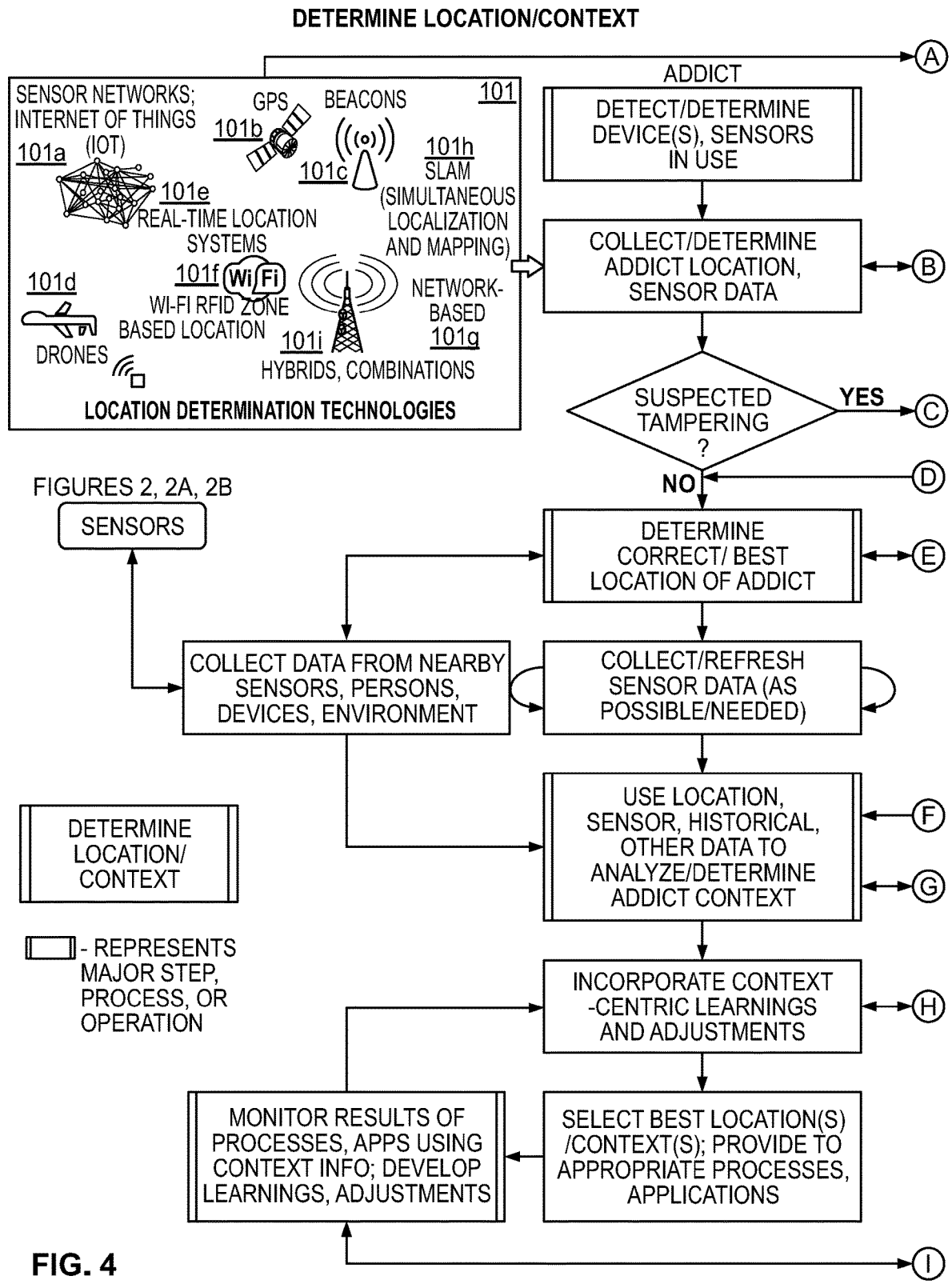
Figure 4:
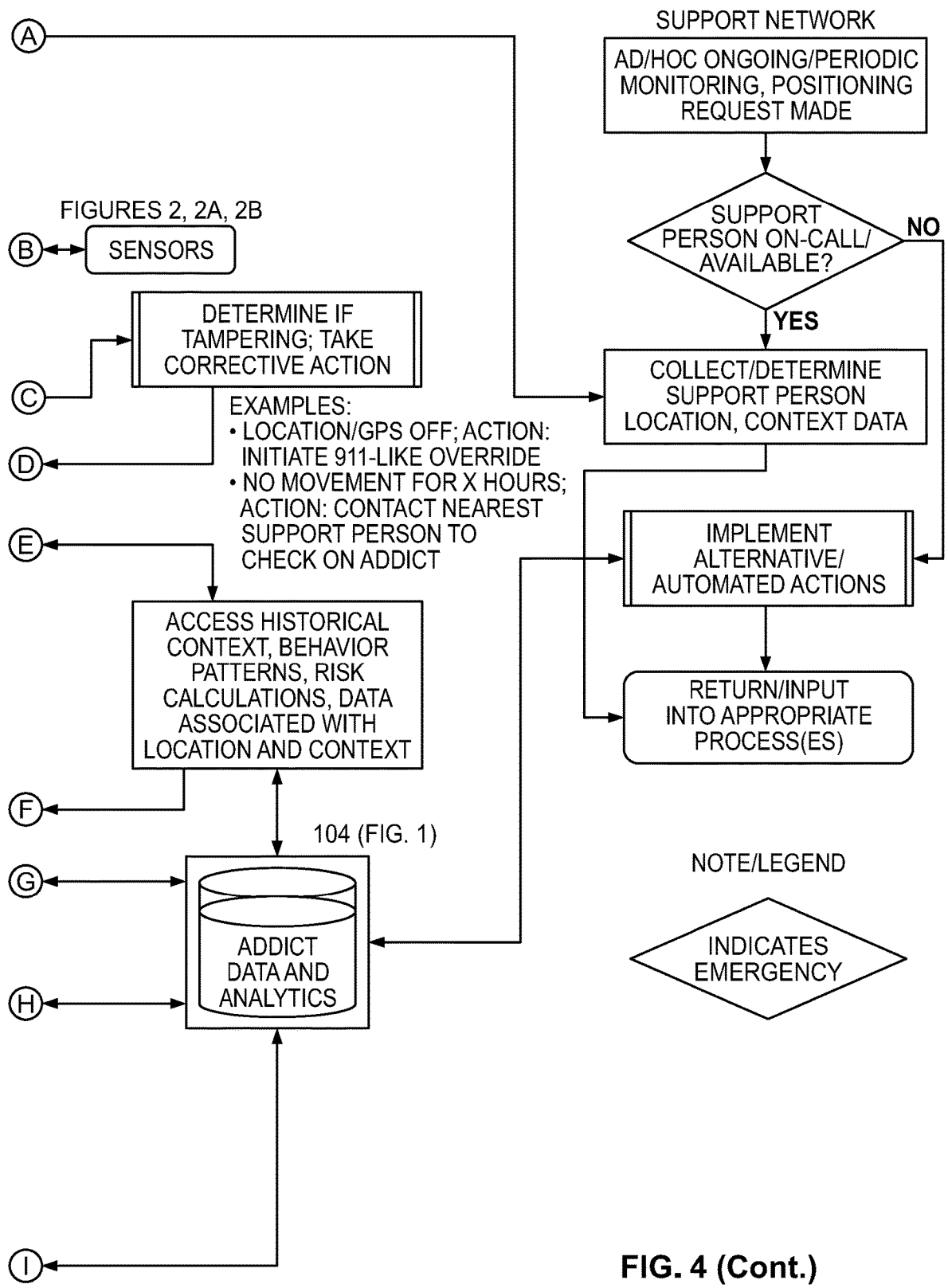

In various embodiments, a learning engine is provided that utilizes artificial intelligence and other learning algorithms and methods to learn from an addict's behavior and to refine various systems, algorithms, and processes, such as an addict's likelihood of relapse, effectiveness of actions taken, and types and frequency of data collected. FIG. 3 depicts an example process for assessing an addict's risk of relapse and determining potential actions and support resources, with FIG. 5 providing more detail on how such an assessment could occur, and how the assessment algorithm may be modified as more data points about the addict's behavior become available.

By way of an example relating to an addict's Anger trigger, an initial approach to detecting an Anger condition may initially be based solely on blood pressure (e.g., a spike in blood pressure is indicative of anger). However, learning mechanisms disclosed herein may find that for a particular addict the correlation between a spike in blood pressure and an anger condition is low. Instead, the mechanism may determine that the addict's anger is immediately preceded in a rapid rise in skin temperature, and is exacerbated when loud noises (e.g., yelling, etc.) is in the immediate vicinity. Thus, the addict's anger-related sensor readings will change from monitoring blood pressure to monitoring skin temperature and noise levels.

Indeed, various embodiments provide leveraging of numerous data sets about, related-to, or of potential value to the addict, and the use of data analytics, algorithms, and analysis engines to aggregate, compile, assess, analyze, synthesize, and otherwise bring together disparate pieces of information (many location-related) that can be used in the addict's treatment. Data/data sets can include but are not limited to information regarding the addict's medical history, personal profile (e.g., friends, hobbies, etc.), schedule/calendar information, historical data (often location-based) that describes past actions and behaviors, key enablers (people/places/things that can aggravate the addiction), key usage triggers, and sources of addiction (e.g., liquor stores, drug dealers)/Points of Interest (e.g., bars, casinos) that the addict has been known to frequent and/or has demonstrated vulnerability to in the past. Such information could be obtained in many ways, including but not limited to directly from: the addict (e.g., questionnaires, etc.), the addict's support network, friends and family, medical data, historical behavioral data, public records, news media, social media, school records, etc. The communications links used to obtain this information can include, but are not limited to, the Internet, wireless and wireline networks, cloud sources, crowdsources, peer-to-peer networking, sensor networks, machine-to-machine networking, smart homes/neighborhoods, and electrical-grid based networks.

Such data sets and other information may be analyzed on multiple levels using analytics that include but are not limited to a Usage Trigger, Potential Response Analyzer, Risk Prediction Algorithms, and an Action/Coordination Engine (many of these concepts are illustrated in FIG. 1 in the Addict Data and Analytics, and used implicitly or explicitly in many of the Figures). The Usage Trigger and Potential Response Analyzer takes as inputs the addict's usage triggers (defined by techniques such as questionnaires or psycho-therapy), and the addict's personal profile and schedule/calendar, as well as historical information about the addict's movements, actions, behaviors, and hobbies, to develop a risk assessment and prediction algorithms about the addict's vulnerabilities to future potential addiction-related situations and develop a series of potential responses. Risk Prediction Algorithms utilize information about the addict's current situation/location/context, addiction triggers, and historical behavioral data to develop a risk score, rating, or level (score) for the addict. If the risk assessment score reaches or exceeds a threshold, and/or falls within a certain range, the Action Coordination Engine will develop an action or course of action that will then be launched, such as contacting members of the addict's support network, rearranging the addict's navigation (away from high risk locations), or disabling the addict's vehicle and arranging for alternative transportation, as a few examples.

In various embodiments, an action/coordinating engine (based on the Addiction Server, one or more of the Addict's devices, via a cloud, or some combination) is provided to coordinate various actions on behalf of or in the interest of the addict. This action/coordination engine (action engine), the use of which is illustrated in several drawings in particular FIGS. 6, 6A, 7, and 7A), is responsible for identifying, determining, and/or managing a variety of actions that the addict, the addict's support network, or others can take on behalf of the addict, usually in response the detection of a relapse risk or actual relapse situation. Such actions could be automatic in nature, such as the engine directing the addict to move to a sanctuary location for example, such as a nearby AA meeting getting ready to start, in response to a high risk alert generated in various embodiments. An action could be more of a coordination function, such as coordinating a meeting between the addict and a nearby addict sport person at a nearby meeting in an hour, action could include interfacing with the meeting place (e.g., restaurant) reservation system, as well as identifying nearby available parking, and providing instructions to the addict's and the support person's cars to activate the self-parking application once in range. This is an example of communicating/coordinating with a variety of third-party applications and services that will make the action(s) go as smoothly and hassle/aggravation-free as possible, as a key to resolving high-relapse risk situation without relapse is often to the addict in as a tranquil, trouble-free mindset as possible.

Other actions include obtaining alternative transportation for the addict, modifying navigation applications to avoid areas where addictions can be enabled (such as liquor stores for an alcoholic), and/or posting on social media that the addict is in a high risk situation. Note not all actions may be reactive, or reactive only to only high-risk or in-progress relapse situations. The action engine may manage the selection and communications of daily morning motivation messages to the addict, or perform an alert reminder function to one of the addict's support persons reminding him do to his weekly Friday call to the addict.

An often underappreciated and overlooked aspect of successful addiction treatment is the use of rewards mechanisms associated with good or desirable behavior. While addiction outsiders often take the attitude that avoiding the destructive aspects of addiction should be motivation enough for an addict to get and stay sober, the reality is that for many addicts that is not enough. Indeed, the destructive aspects of addiction get progressively less of concern to many addicts the longer they are addicted. However, the prospect of a reward for good behavior (not relapsing) can have a very stimulating/powerful effect on some addicts-thus, various embodiments provide a method and apparatus for detecting/determining good behavior and rewarding such behavior. For example, as shown in FIG. 9, a rewards mechanism is provided under the presumption that many addicts' need a positive-enforcement mechanism as a deterrent to relapse. For example, engaging in good behavior such as avoiding trigger aggravating locations and contexts earns points, as does attending (in person or virtually) addiction community meetings. The points accumulate, and can periodically be redeemed for (usually) addiction-related goods and services, such as passes to (non-alcohol serving) movie theaters or deep discount coupons for safe hobbies such as gym memberships or sewing supplies. In contrast, risky behaviors such as visiting with bad friends (friends that very actively drink for example) could results in points being deducted.

More broadly, various embodiments include rewards for behavior that inhibits or prevents addiction usage/relapse (e.g., good behavior), and/or behavior that specifically avoids relapse or the possibility of relapse (e.g., bad behavior). While ideally the addict will be self-motivating in his/her desire to get sober, the reality is that many if not most addicts need some sort of external motivation and reinforcement—both positive and negative—to get and particularly stay sober. Thus, a sobriety rewards program can be an integral part of various embodiments. For example, the addict may accrue reward points when he or she spends time in a new (good) hobby, or exercises for at least 30 minutes a day. Similarly, points may be earned if the addict does not go near vulnerable locations such as high drug areas, bad friends, or liquor stores for at least 30 days. An example embodiment would detect and track these good behaviors through functionality disclosed herein and/or data obtained from interfacing with other applications and devices used by the addict or his/her support network. Rewards could be in many forms, such as points redeemable for goods and services, discounts on using an embodiment of the present disclosure or related applications, free tickets to an event (presumably but not necessarily safe events), or even direct cash credits to their bank account or mobile pay account. Note a further feature of the present disclosure may be to detect/prevent the use of any financial transaction for the purchase of substances negatively related to the addict's addiction. Thus, purchases from liquor stores would be detected and rejected via interfaces with the addict's financial accounts and transaction enablers, e.g., credit/debit cards, mobile pay and bank accounts, etc. Similarly, credits could be posted to these accounts. Credits could be selectively posted for good behaviors, such as paying for new hobbies, free Uber rides, etc. Similarly, bad (or not good) behavior could result in points/financial deductions from the addict. In one example embodiment, a reward engine would determine the applicability and value of such behaviors, track such additions/deductions, and coordinate with addict-related third party accounts.

Not all motivation-enhancers will be rewards-oriented; some need to be encouragement-oriented. This would include words-of-encouragement, testimonials, thoughtsfor-the-day, and other types of motivation or self-esteem building messages. Thus, various embodiments provide ways of detecting when such messages would be particularly timely, selecting appropriate messages, and delivering them to the addict at the appropriate time, context, and using the best method for encouraging the addict to get on/stay on the path to sobriety. For example, an embodiment of the present disclosure may determine that the addict is susceptible to the Time of Day trigger, when he/she particularly desires drinking at 5 pm every day. Starting at 4:30, motivational messages and testimonials may be sent every 15 minutes, such as "life is short—make the most of it!" This could be sent using any number of methods, including text, MMS, email, (pre-recorded) phone call, internet/(private) social media, and other methods. The embodiment could also automatically create rotating schedule reminders to (random or previously selected) various members of the addict's support network so that those members could connect real-time with the addict to offer words of encouragement during these vulnerable times-of-day.

Sometimes actions require more than a positive reinforcement-orientation, meaning a more urgent, aggressive approach may be needed. One such scenario could involve the detecting of the addict relapsing while at a bar, and having driven himself there. The addiction server will have monitored the addict's smartphone for example, showing that both it and the addict's car have been following the same path and has stopped at a local bar. Sensors on the addict's clothing will have detected the presence of alcohol, and other sensors noting a risk in blood pressure and blood alcohol content. Such data may cause the Risk/Prediction engine to generate a very high alert—addict has been drinking. If no addict support person is in the immediate vicinity to get the addict, the action engine may elevate the urgency and send signals to the addict's vehicle that disables it (an alternative would be putting it into self-driving mode if such option were available). Concurrent with disabling the call would be requesting an Uber/taxi ride dispatched to the bar, with an alert to the addict that such a ride has been arranged for, with the details showing on the addict's smartphone screen. To make it clear that the addict needs to get into the taxi, the action engine may also inform the addict that one of his support network will be meeting the taxi at his home in 30 minutes, and he is expected to show at that time. Since this meeting would be considered a penalty meeting, the addict will lose points from his sobriety program if he is not punctual.

Numerous communications methods to/from the addict and other resources are used in various embodiments of the present disclosure. These can include (but are not limited to) text/SMS/MMS, voice calls, email, social media, video, peer-to-peer and machine-to-machine communications, instant messaging, voice messaging/mail, 3rd party applications, heads-up-displays (such as Google Glass), hologram projections, and other applicable voice and data methods and mediums. For example, the server may alert via text someone in the addict's support network that the addict is nearby and should be contacted because of a detection of a high-risk situation. The support person may send the addict an MMS with an uplifting message, and also send an invite to the addict via a 3rd party application to meet him at a local restaurant at a certain time. The addict could respond with an instant message thanking the support person, and accept the invitation via the 3rd party app along with a note that the addict will be approximately 15 minutes late. The support acknowledges this via a return text, but hits an option on his device to instruct the addiction server to increase the location monitoring of the addict to detect if he/she takes a relapse-type action (such as stopping at a liquor store). These real-time updates may be transmitted to the support person in the support person's car system display/voice system or augmented reality sunglasses on the way to the restaurant so he/she knows exactly what the addict has been doing since the original alert was issued.

As introduced above, a key element present in many embodiments of the present disclosure is the use of location technology such as mobile devices and associated GPS or other location determination technology to track or monitor the location of the addict. The addict's location can be continually, periodically, occasionally, or on an ad-hoc basis compared to numerous other individuals and/or data sources to provide location-related assistance to the addict in continuing his treatment or in avoiding succumbing to the temptation of his or her addiction.

Another feature or aspect of the present disclosure is the use of unaugmented reality technology. Instead of inserting objects into an addict's environment (such as a Pokemon character), instead an exemplary embodiment includes performing a continuous, real-time or otherwise timely monitoring of the addict's environment, detecting threatening objects such as advertisements for alcohol, and blanking out or otherwise hiding or obstructing the addict's ability to perceive such threatening objects. This could range from removing such objects from a navigation screen (such as liquor stores) to actual blanking or replacing said object within a Google Glass or Snapchat Spectacles or other Virtual Reality interface.

Another feature or aspect of the present disclosure is the development and use of risk scores of relapse or other adverse treatment situation. Such scores could be in the form of a number (like credit scores), a high/medium/low designation, color schemes (e.g., Red, Yellow, Green, etc.), and other scoring and/or range classifications (scores). Such risk scores could be for a variety of risk types: general risks, situation-specific, location-related, and/or date/time or date/time-range specific risks, among others. An embodiment would develop these risk assessments/scores using data/data sets but not limited to the addict's medical history, personal profile (friends, hobbies, etc.), schedule/calendar information, historical behavior data (often location-based) that describes past actions and behaviors, key enablers (people/places/things that can aggravate the addiction), key usage triggers as described above, and sources of addiction (e.g., liquor stores, drug dealers)/Points of Interest (e.g., bars, casinos) that the addict has been known to frequent and/or has demonstrated vulnerability to in the past.

Such scores would be developed/calculated continuously, periodically, ad-hoc, or on-demand, as well as when certain individual conditions are detected by various devices and/or combination of conditions, as well as device-independent conditions. An example of a device-independent condition would if it were detected by external data sources that the addict was facing a heavy traffic jam on his usual route home at the usual time. Knowing from his trigger profile that this situation could activate the Anger trigger (e.g., road rage), the Risk Assessment Engine would calculate a high risk score. This score, in turn, may be used in various other aspects of the present disclosure.

Taken together, various implementations of the present disclosure could monitor the location of people in an addict's support network—such as social workers or their sponsor in an addiction treatment program—to have them alerted and ready to stand by to assist the addict if the addict appears to be heading into a difficult situation, such as physically meeting an alcoholic if they appear to be in danger of entering a bar. To detect this kind of scenario, the addict's location may be compared to other data sources of potentially dangerous locations such as bars or liquor stores (for alcohol addiction), known drug-trafficking areas (for drug addiction), casinos (gambling addiction), shopping malls (shopping addiction), and so on. If it appears that the addict is possibly going to enter a dangerous situation or area, the nearest person (to either the addict or the place in question) in their support network can be alerted to intervene.

In various exemplary embodiments, integration and coordination are provided with the addict's medical and psychological status and prognosis. Medical and psychologist/psychiatrists can embrace various embodiments as providing ways to monitor real-time the progress of their addiction patents, as well as provide near real-time/real-time adjustments to medications. For example, an embodiment, in monitoring addict with an embedded naltrexone dispenser, may start detecting high-risk behavior. The example embodiment could inform the addict's psychiatrist of this behavior, who then may decide that the medicine will need to be increased in dosage. The embodiment would interface to the service/application controlling the embedded naltrexone, e.g., either remote or attached/embedded with the dispenser, increasing the dosage, all potentially in real or near-real time, or as otherwise directed by the addict's medical professionals.

More broadly, this may entail obtaining or otherwise receiving access to an addict's treatment records, providing updates to those records, and interacting with rehabilitation, therapy, and/or medical providers. It may also entail acquiring access to pharmaceutical/drug treatment prescription information, and being able to administer through the addict's controller device real-time modifications to drugs administered through the controller.

Such an embodiment could also be used by rehab professionals, in monitoring compliance of addicts under active treatment, during those periods where the addict is in a halfway house or similar situation, where the addict is no longer being closely monitored by rehab personnel but it is desired to see if the addict can manage by oneself in a somewhat controlled situation. The example embodiment may monitor the addicts attached/embedded devices as well as other behavior to detect out-of-desired norm conditions or positive ("good") behavior which will then provide additional data towards release of the addict from treatment.

Some exemplary embodiments of the present disclosure include the use of crowd sourcing in generating and disseminating addiction-coping ideas and actions. For example, in FIG. 10 an addict enters a room where an "open" beacon is placed as part of a real-time location services (RTLS) network. In addition to providing location help, the beacon also serves as a repository for addiction-related ideas only for those people who are "tuned" to that beacon, such as a special ID and/or application that enables a one or two-way communication between the addict and the beacon. This could be, for example, only for alcoholics, only for addicts with the Anxiety trigger, and only accessible if the addict is in physical communications range with the beacon. The addict could download ideas for dealing with Anxiety for example, including specific ideas relevant for that specific location. Alternatively, the addict could upload uplifting messages such as praising the locale for its calming environment. It could even be used to identify and connect addicts with similar triggers that are in range of the beacon at that time, thus allowing ad hoc, spontaneous, unscheduled, or flash interactions not otherwise possible or likely. In effect, this would enable very specialized, private ad-hoc meetings or linkups between two or more addicts suffering from similar issues, in a safe, public yet private, anonymized environment As noted before, helping the addict avoid relapse into their addiction is not necessarily voluntary. Several of the embodiments of the present disclosure are predicated on providing help to the addict without their advanced knowledge and/or permission. In various embodiments, no assumptions are made regarding the legality of such assistance, but it is presumed that the embodiment includes acquiring permissions from/for the addict, either directly or via parental/court-ordered ones on behalf of the addict.

One example embodiment of an involuntary use is tracking of the mobile device(s) of an alcohol-related court offender. An extension of GPS device tracking for parolees, the embodiment could continually track the movements of a court-ordered person who is required to attend AA meetings and/or stay away from any alcohol establishments. The embodiment would correlate the person's movements and report back to the court or parole officer to confirm adherence to the court order, or alternatively provide proof of violation of the order. In extreme cases, an embodiment could be configured to report directly to the local police any situation where addict impairment is detected, along with necessary information to apprehend the addict, e.g., location of the addict/vehicle.

Various embodiments provide insertion, to the extent possible and appropriate, of inspirations, testimonials, motivational messages, and other positive (or deterring) information into an addict's daily life. What messages/information this would include would depend on the addict's location and/or context, in order to maximize their appropriateness and effect. A common theme throughout many of the embodiments is the use of these kinds of messages. The "delivery" of such can come in many forms—again geared to maximizing the ability for the addict to pay attention to and assimilate such messages—through the appropriate interfaces as well as third party applications such as social media, twitter, Facebook, snapchat, etc.

Various embodiments of the present disclosure provide monitoring of an addict's physical and mental condition through the use of sensors, such as wearable ones of even medical sensors embedded in the addict's body. These sensors can be monitored to detect conditions of particular danger or vulnerability to the addict, such as a spike in blood pressure that could be indicative of the addict becoming angry. If this trigger is detected, a message could be sent to the nearest person in the support network to alert them and have them contact the addict to arrange a calming meeting. Alternatively, if there is no one nearby, an embodiment could then interface with other medical delivery systems attached or embedded in the addict to deliver a tranquilizer or dose of a craving-inhibiting drug or other medical treatment. Similar actions could be taken with implants, prosthetics, or other artificial body/brain parts.

Various embodiments of the present disclosure provide minimizing of the extent of and damage from a relapse of the addiction. This could include the detection (such as via sensors, mobile device, or support network) that the addict has relapsed. This relapse once detected may set off a chain of events such as locking or disabling the addict's personal or work transportation if he/she gets within 100 feet of it; to automatically call a taxi or Uber-type service if the addict is in need of transportation (facilitated by accessing the addict's schedule and relapse contingency management instructions); to alert as appropriate portions of the addict's support network; alert family that the addict has "used" and is under-the-influence (for substance addiction); if appropriate automatically lock-out the addict from certain houses/buildings if the addict comes within a certain range; to alert school officials if the relapsed addict is detected with a certain distance of their children's schools; even to alert law enforcement (and his lawyers) if a breach of a restraining order is imminent.

Indeed, there are many transportation-related embodiments related to the present disclosure. As numerous studies show that a high percentage of violent crimes (and of course other crimes such as drunk-driving) occur under the influence of alcohol or other substances, there would be many scenarios under which transportation would play a key role if impairment of the addict is detected or suspected. These could include involvement of the addict's friends or family (e.g., automatic programing of a driverless car to take the addict to their house), ex-girlfriends/spouses (preventing driving to their location(s), addict's support networks (routing those persons to the addict), even law enforcement (routing law enforcement to the addict's location).

As the above scenarios illustrate, the civil liberties, privacy, and/or security of an addict are considerations to be taken into account in various embodiments. Accordingly, in various embodiments, a privacy engine is provided that determines the conditions under which the addict's location/context can or cannot be disclosed or used. In most situations, the privacy engine may be under the control of and/or entail the acquisition of the approval of the addict. For example, the addict may "pre-approve" an embodiment in which a car is disabled or re-programmed in the event that usage is suspected. Many addicts who admit they have an addiction and are trying to become sober will agree to such conditions. They may recognize that that kind of monitoring and control mechanisms would serve as effective deterrents. In various embodiments, a privacy engine may prevent override of previous deterrence approvals in contexts where the privacy engine detects usage/abuse. But similar to parolee GPS ankle bracelets, the addict may not have control over the privacy engine in some exemplary embodiments. Instead, it may be under the control of a parole officer, medical professional, or other responsible party (for the latter, for example, the addict may sign power of control over to a trusted family member).

In various embodiments, various differing privacy levels and other control mechanisms may be provided through multiple administration/authorization levels. For example, an addict may have one level of access, and an administrator can have a second, higher-level of access to control/override the addict's choices. There may also be additional levels of admin/control such that someone such as parole officer or medical professional may manage multiple addict's profiles with the same user login information. Although the typical control over any one user's privacy may be controlled by only one individual at a time, it is conceivable that multiple persons may have concurrent control, such as a parole officer and a medical professional.

There may also be the opportunity to anonymize people involved in various embodiments. Not only may there be times when an addict desires to be anonymous, even to people within his or her support network, but a support network person may want to be anonymous to the addict. An example of the latter for example may be when there is no one available in the addict's known network to talk to at a vulnerable time-particularly if a relapse is in progress and no one in the addict's known network is available. In one example embodiment, an addict may connect, as a backup, to a general or on-call addiction support person that may provide someone to talk to, or even arrange to meet if they are close together.

In various embodiments, obstacles may be introduced to obtaining the addiction substance or pursuing the addiction activity. One example is in using the information from one or more of the scenarios in combination with the proximity of the addict to transportation sources, such as the addict's car. In situations where the addict has relapsed, various embodiment components may automatically interface with transportation systems within the addict's reach and/or control to disable them or modify them, for example switching on a driverless car feature (and preventing manual driving).

In various embodiments, interfaces are provided that are ways of interacting with the addict. One common and unfortunately generally applicable characterization of addicts is the tendency to be lazy. It is more accurate to say that because of the effects (or after-effects) of their abuse (particularly substance abuse) they have low levels of energy, motivation, and attention span. In various embodiments, interfacing—i.e., receiving input from but particularly providing output to—the addict can be very effective when appropriately provided. Thus, a wide variety of interfaces may be provided, the deployment of which is often context-dependent, and appropriately simple and intuitive for the addict to use, with minimal actions required on part of the addict.

The use of Siri and other types of personal assistants are anticipated and included as possible interfaces. For example, if it the addict is determined to be at high risk of a relapse while home alone, a program could be initiated that talks to the addict to ask the addict what is bothering the addict (if the trigger is Loneliness for example and no human support person is available), or to suggest a call to mom if a trigger response to do so is high on the response list. The use of such interfaces could even be adjusted to use the type of voice (e.g., male, female, English, Australian accent, etc.) that has been determined to be appropriate in the past. The use of the addict's children's voices could also be used, as a reinforcer or defense to not to drink otherwise the children will be harmed in some way.

The types of interfaces anticipated to be used are wide, varied and utilizing a diversity of technologies. They may range from, e.g., variations of smartphone interfaces (e.g., touchscreen, high quality video/sound, etc.) to others such as augmented reality, personal robotics, etc. The goal of using such interfaces in all cases is the same: to have a significant effect on the addict, which in turn may be provided by an interface appropriate for that addict in a particular context.

The use of augmented reality and robotics can be beneficial in addiction treatment. With Augmented Reality, particular contexts/situations may be modified to both see things that are not there, but not see things that are there, or see different things (also referred to as de-augmented reality). For example, for alcoholics who see a spike in their desire to drink when they see a liquor store, their Google Glasses or equivalent may be programmed to block out all words and images of alcohol as they drive by. An alternative may be to replace the words and images with something benign, such as words and images about a charity, or even replace them with disgusting words and images along site symbols of alcohol in order to associate such disgusting words and images (such as someone vomiting) with the concept of alcohol.

As discussed before, interfaces with third party applications may be provided in various embodiments. For example, interfaces with social media applications can identify friends who are nearby as candidates for transactional support needs (e.g., serve as support network substitutes if no other resources are nearby). Navigation applications can be modified to exclude the location of liquor stores or casinos. Communicating with support resources via Snapchat, WhatsApp, Twitter, or Facebook can be used depending on the best/most convenient way of interfacing with an addict and/or their support networks. A filter and program can be applied to online grocery applications that may prevent alcohol purchases from being made. This type of prevention may be extended such that if an alcoholic nears a local bar, an interface may be established with the bar's systems that download a Do-No-Serve notice to the bar owner along with facial recognition information.

In various embodiments, a wide variety of interfaces may be provided to interact with the addict, support network, and third parties. Such interfaces include but are not limited to: Direct manipulation interface (e.g., augmented/virtual reality), Graphical user interfaces, Web-based user interfaces Touchscreens, Command line interfaces (e.g., command string input), Touch user interfaces Hardware interfaces (e.g., knobs, buttons) Attentive user interfaces (e.g., that determine when to interrupt a person), Batch interfaces, Conversational interfaces, Conversational interface agents (e.g., animated person, robot, dancing paper clip), Crossing-based interfaces (e.g., crossing boundaries versus pointing), Gesture interfaces (e.g., hand gestures, etc.) Holographic user interfaces, Intelligent user interfaces (e.g., human to machine and vice versa), Motion tracking interfaces, Multi-screen interfaces, Non-command user interfaces (e.g., infer user attention), Object-oriented user interfaces (e.g., to manipulate simulated objects), Reflexive user interfaces (e.g., achieves system changes), Search interface, Tangible user interfaces (e.g., touch), Task-focused interfaces (e.g., focused on tasks, not files), Text-based user interfaces, Voice user interfaces, Natural-language interfaces. Zero-input (e.g., sensor-based) interfaces Zooming (e.g., varying-levels of scale) user interfaces. Various mechanisms may be provided for selecting/modifying the interfaces based on the user's context. Such mechanisms are part of the User Interface Detector/Selector/Interface (UIDSI) unit in the Addict Monitor/Controller (AMC) 200 shown in FIG. 2.

In various embodiments, robots and robotics may be used. A robot could be used, for example, to serve as an addiction monitor, controller, and/or enforcer. A robot, sensing or being instructed that a high-relapse risk situation is developing, might literally grab the addict by the hand and lead them to a different (safe) destination.

In various embodiments, scheduling and to-do lists of the addict are utilized, as well as the addict's support network. For the support network, integrating with any scheduling program that they use (such as Outlook) can assist in determining their availability (and in some instances location) when an addict risk situation occurs. For the addict, an embodiment may make a dynamic scheduling adjustment and/or add or delete to-do items if in so doing so reduces the risk of relapse for a particular situation. For example, various sensors and other information may indicate that the addict's anxiety levels are rising in the morning. A schedule may have some high probably high anxiety-inducing appointments in the afternoon, for example a meeting with an ex-spouse and their lawyers that afternoon. Various embodiment algorithms may determine that such a meeting is too high risk, and prompt (say via a speech, Siri-like interface) the addict to determine if the meeting should be rescheduled, and do so if the answer is yes (in some embodiments it may even be done automatically).

Consistent with simple and intuitive philosophy of the interfaces, an Addict Monitor/Controller (AMC) 200 (FIG. 2) may have a variety of form factors. Such form factors may include, e.g., being part of a mobile phone, tablet, PDA, or laptop; part or fully of Tablet/Laptop/PDA, implants, wearables, wrist devices, or any number of form factors. Note also that while the functionality described for the Addict Monitor/Controller is anticipated to be done on the device, it is not necessary, and could be done on a server, in the cloud, via peer-to-peer, or some other processing mechanism.

The variety and diversity of interfaces and the ability to detect/select them—including specialized interfaces within the Monitor/Controller and interfacing to other third party devices via their interfaces—are effective for: 1) determining the context, 2) receiving input from the addict in the ways most convenient to the addict, 3) providing information/output to the addict in the ways most receptive to the addict, and/or 4) providing the most effective deterrent(s) to prevent (or inhibit) a relapse from occurring.

For determining context, an addict user interface detector/selector (UIDSI) on the addict monitor/controller (AMC) may utilize sensors on the AMC to detect context-related data. A simple example is using an optical sensor to detect the addict's light environment, helping to indicate if the addict is inside or out, in a lighted environment or dark. Readings (like loud music) from the audio sensor may be used, e.g., to confirm/modify a conclusion (supported by data from the Locator) that the addict has entered a Rave (an impromptu party with large amounts of substances to abuse) and is in a high-risk context.

Various embodiments may include the linking and coordinating of ad-hoc, spontaneous, unscheduled, or flash meetings between two or more addicts—who may or may not know each other—who either are a) generally open to idea of meeting; b) would like to meet a certain time and/or place; and/or c) are concurrent/coincidently sharing similar trigger risk profiles and where a potential solution for a high risk situation is their meeting, preferably in a sanctuary location.

Various embodiments utilize physical locations as part of their risk identification and/or resulting actions/solutions or coordination efforts. However, many if not most of such embodiments may also use virtual locations as part of their description. For example, if an addict is posting on or in a chat room online (in a situation where their physical location is not relevant, determinable, or near anyone else), and making comments indicating a relapse/usage mindset, a risk assessment engine through a social media monitoring module could detect these comments and generate an alert to the addict's support network. In turn, those members of the support network who were also on that social media site at the same time (or could quickly log on to it) could then join the addict at that virtual location to interact live with the addict, to talk about their risk situation and/or active triggers. In this sense, the physical location of the addict and the appropriate support network person is not nearly as relevant as is their presence at/on the same virtual location on the Internet that enables them to interact real-time.

Figure 5:
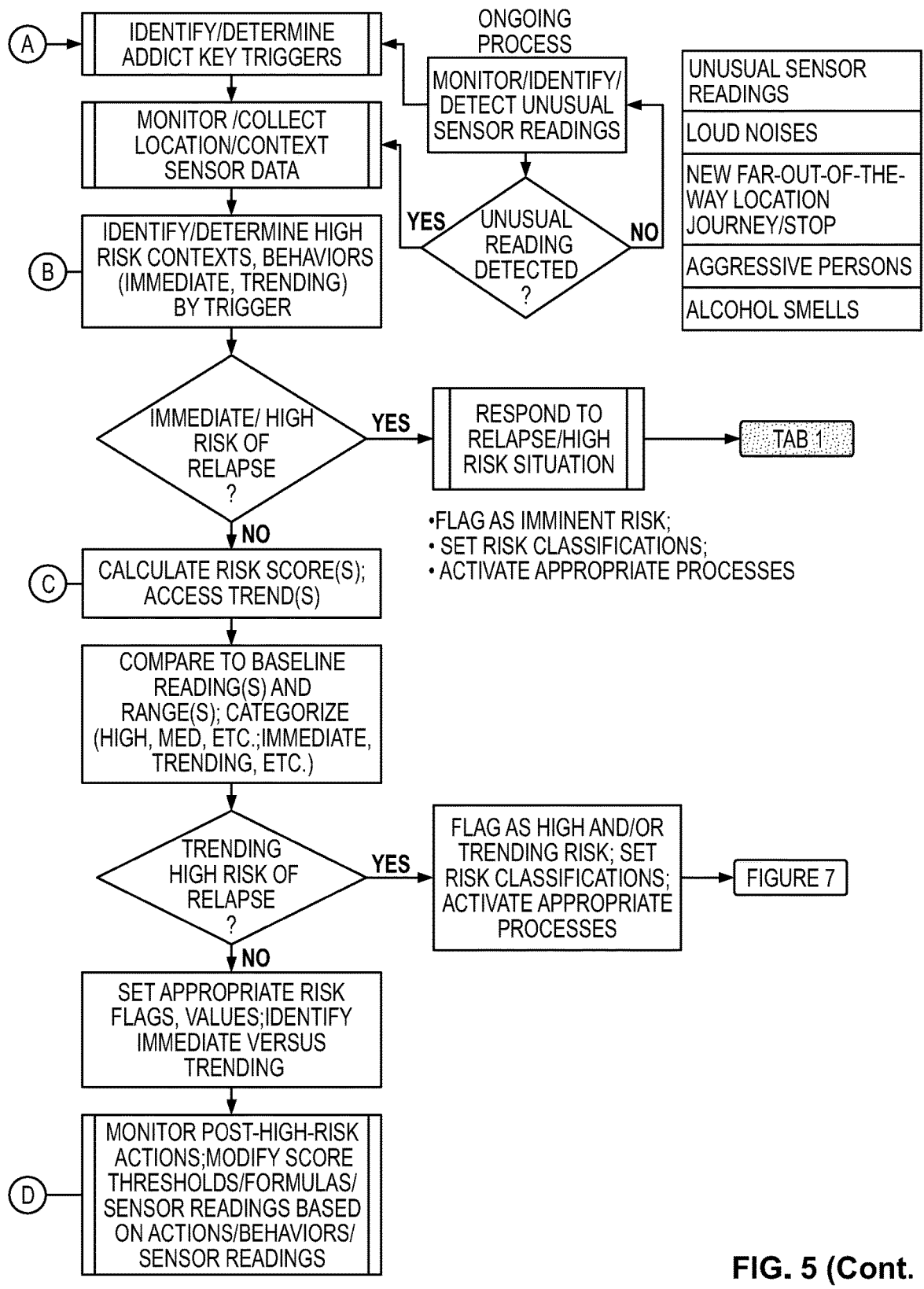
Figure 5A:
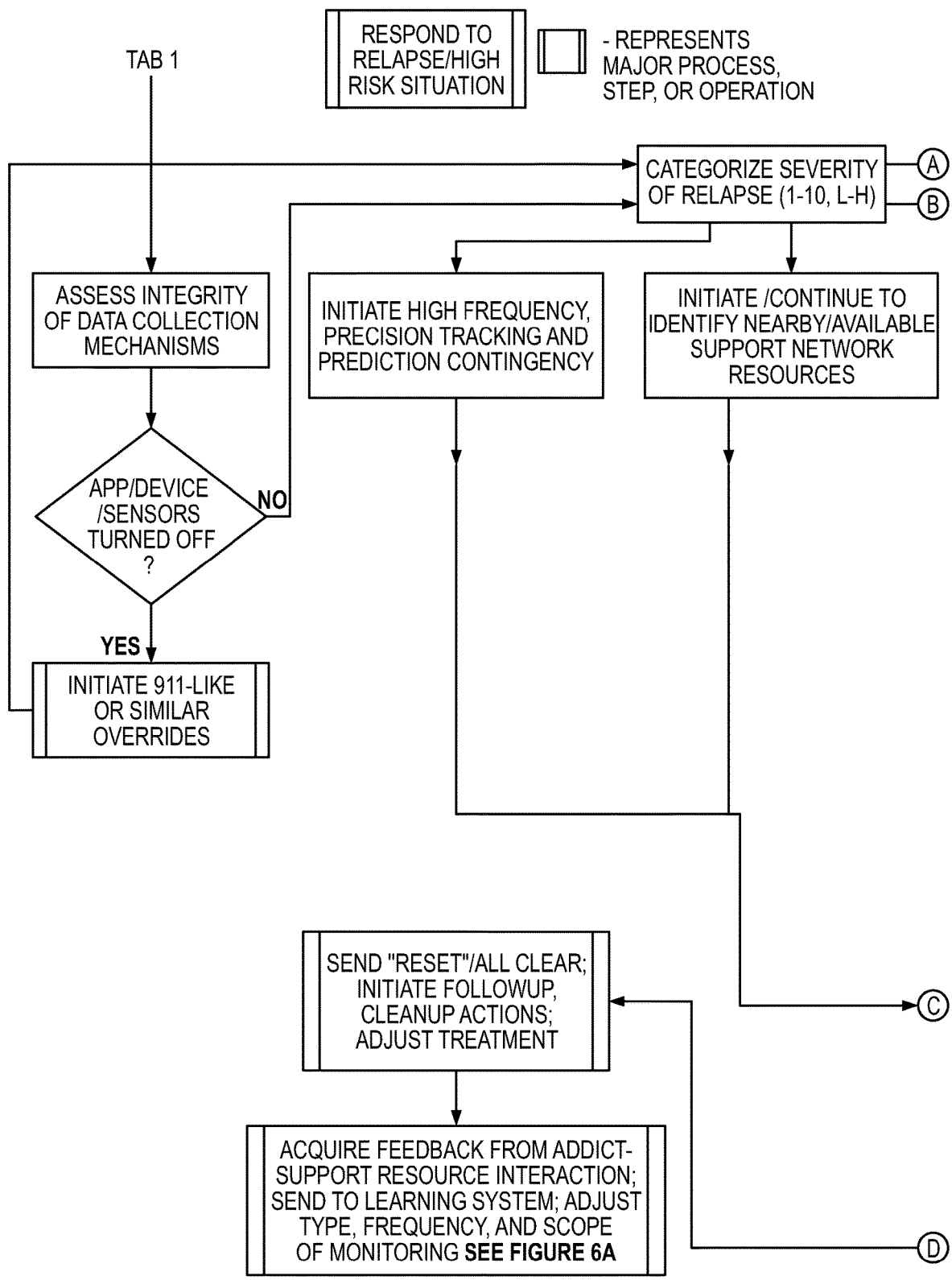
Figure 5A:
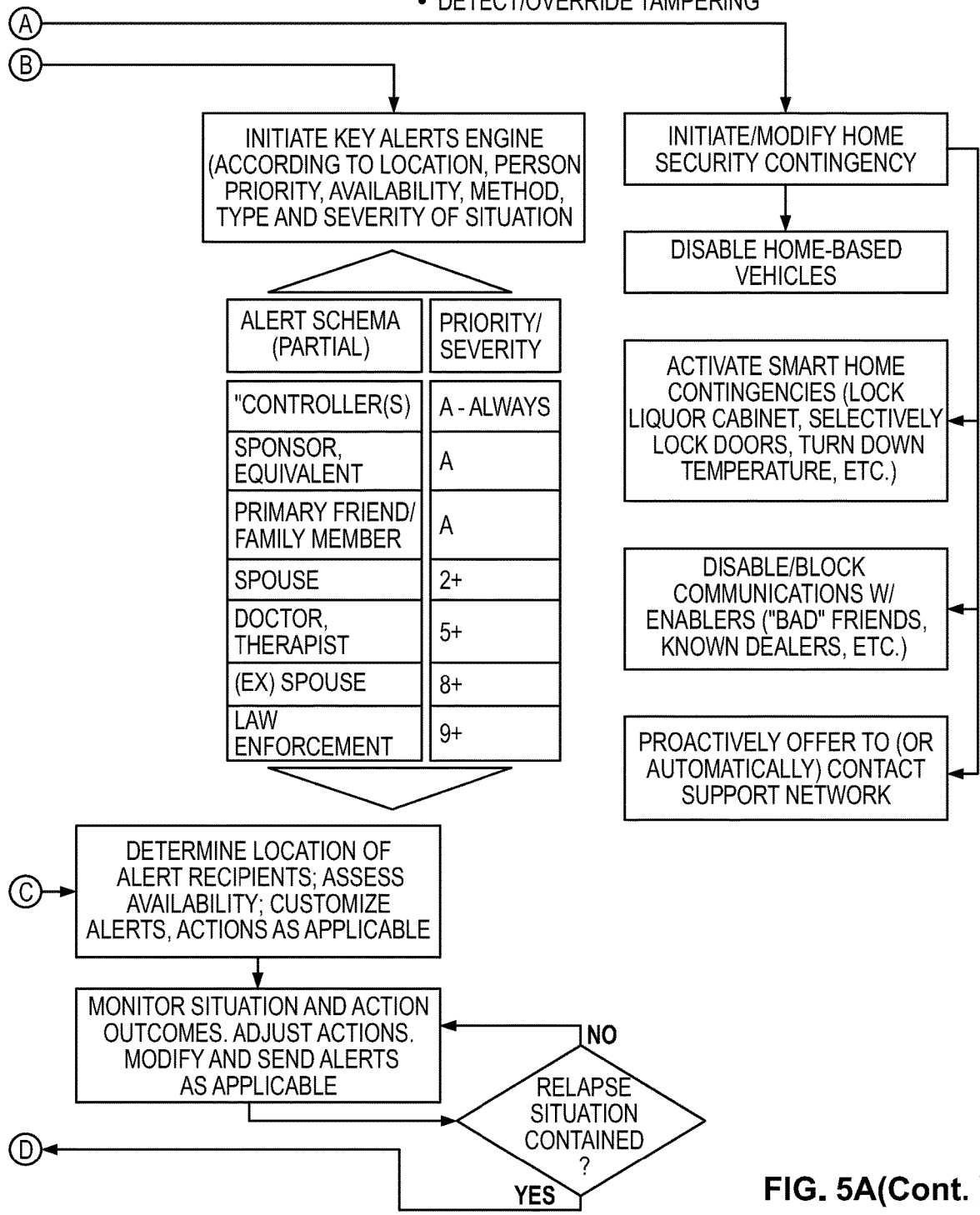
Figure 5B:
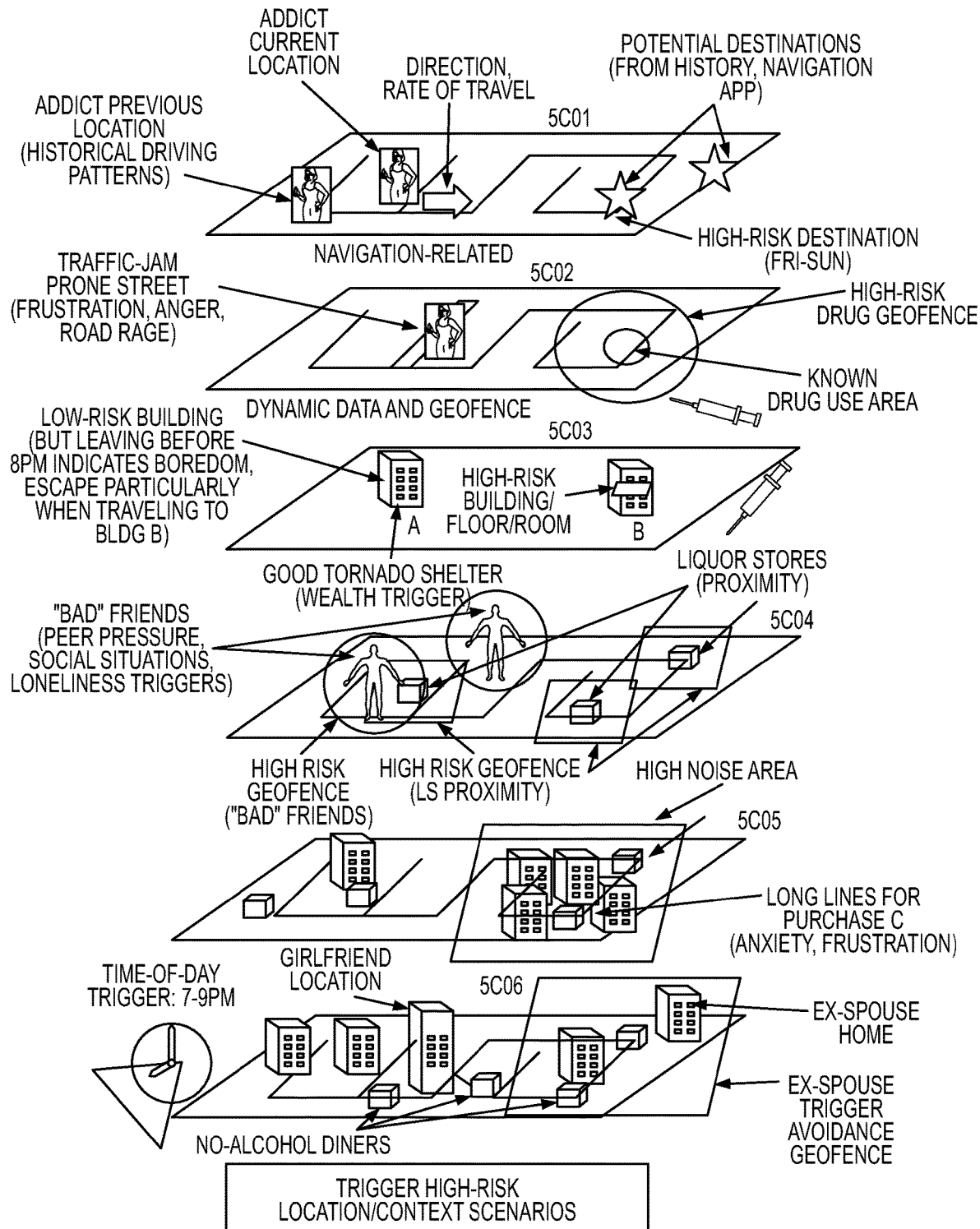
Figure 5B:
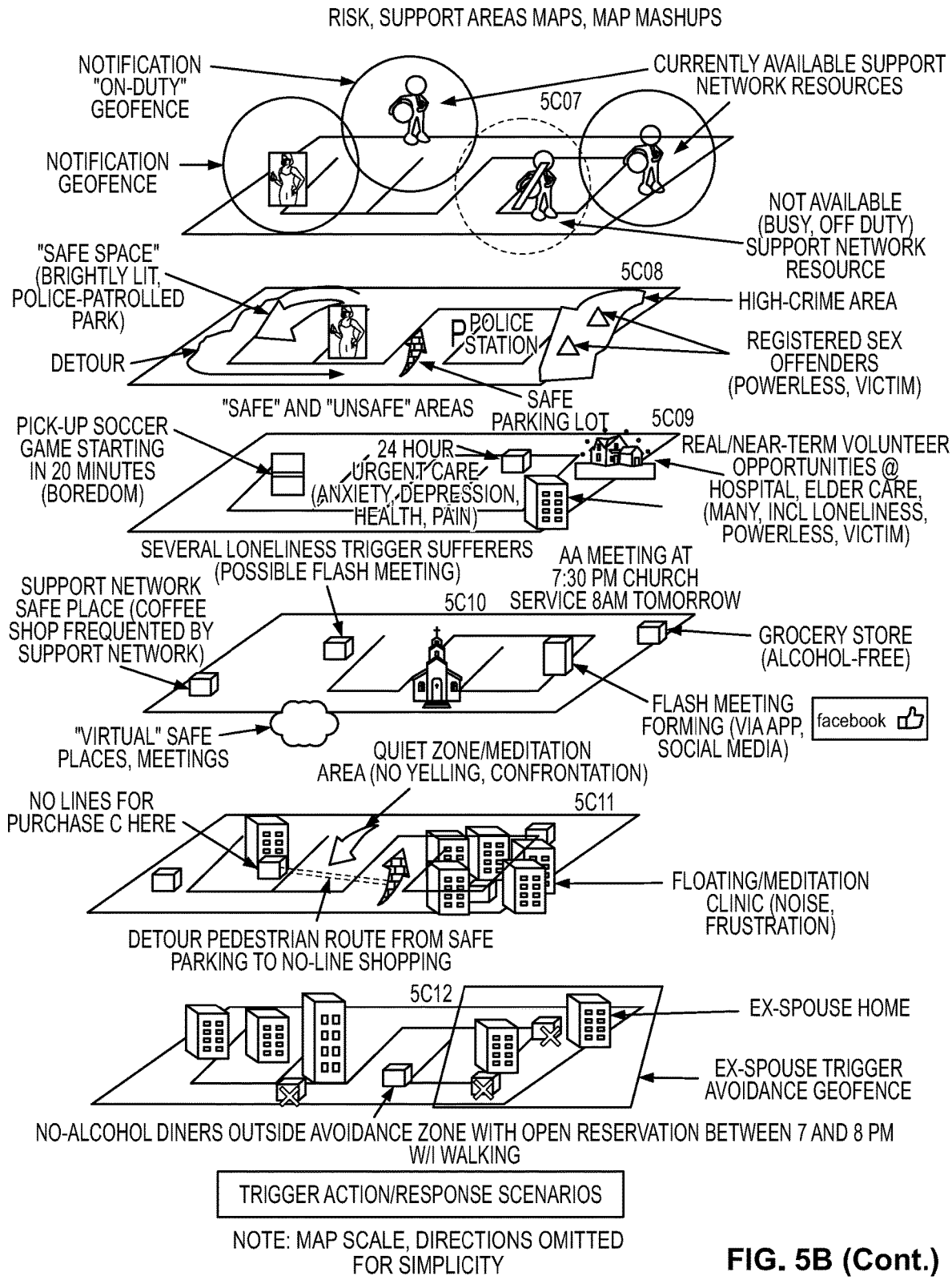
Figure 6:
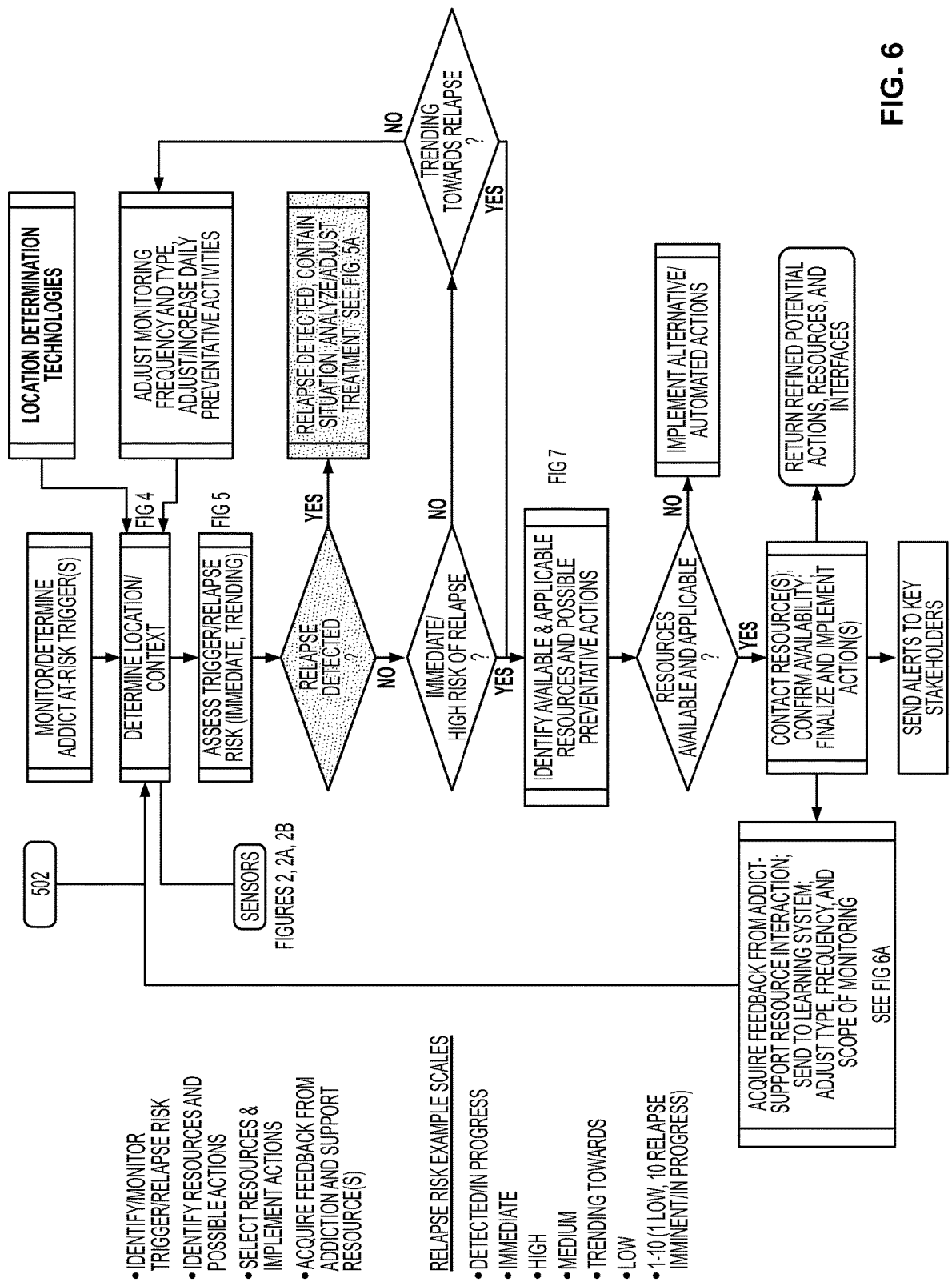
FIG. 6 depicts example ways to identify/monitor trigger/relapse risk and identifying, selecting, and implementing support resources and actions.
Figure 6A:
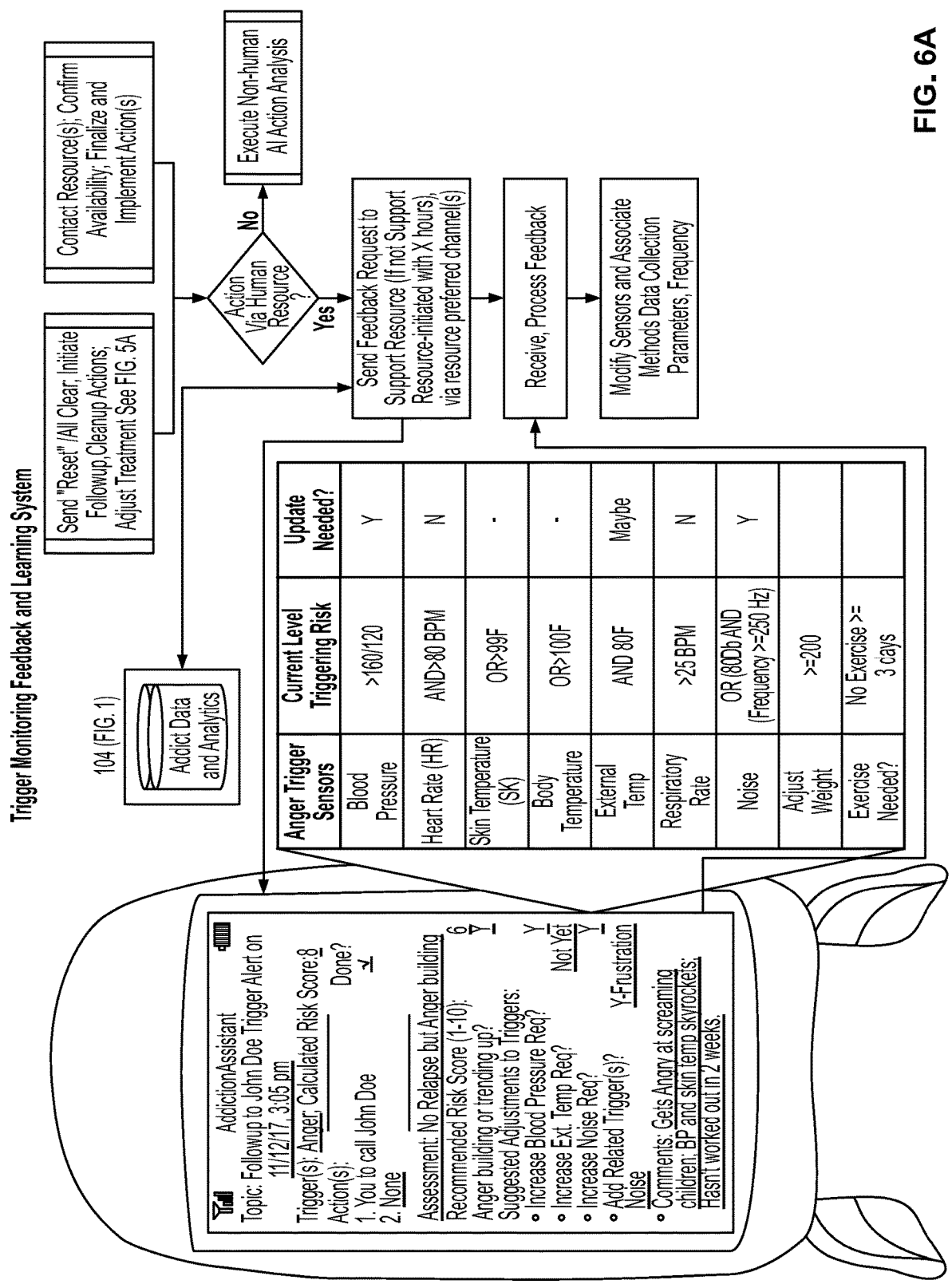
FIG. 6A depicts an exemplary embodiment of a trigger monitoring feedback and learning system.

Various embodiments utilize algorithms that assess and determine the potential of a relapse of the addiction(s) in question. Such algorithms may be based on many factors, including, e.g., addict's profile, behavior/context history, triggers, medical data, the current or trending context of the user, etc. As shown in FIG. 5, such information could be utilized in a set of prediction algorithms and/or scoring formulas geared to determining a current or trending degree of risk.

Various embodiments utilize the concept of trending context of the addict. Various embodiments may attempt to anticipate/predict the addict's context at some point(s) in the future—10 minutes, 1 hour, 3 hours, etc.—in order to identify high-risk situations and proscribe some sort of preventive actions. A simple example is detecting the travel of the addict on a route for which a highly likely/only conceivable destination is a prohibited or forbidden destination, such as a liquor store, gambling establishment, known drug-dealing area, etc., or related forbidden areas such as an ex-wife's house under a court order of protection.

The above trending context example is also an example of various embodiments' integration with other applications. In the above example, the prediction of the addict's destination of a liquor store, gambling den, or drug haven may be made very simple if the addict programs the destination into his/her GPS navigation application. An interface may be provided by one embodiment that would automatically (subject to privacy and/or administration limitations discussed earlier) transmit the destination/route information from the navigation application to the embodiment, allowing confirmation of the addict's destination.

Various embodiments provide integration with third party applications, systems, and processes, e.g., as relating to dealing with high risk or actual relapse situations. For example, in situations where it is deemed too risky for an addict to drive a car, an embodiment may automatically scan through alternatives to get the addict home or to help, without them endangering themselves or others by getting behind the wheel. This could include automatically integrating with an Uber or Lyft application to obtain a ride, or interacting with the addict's car to alternatively disable it, make it switch to self-driving mode (and not allow manual driving at all), or only switch on if the addict was a passenger. Such third party integration could be extended even further, for example, extending to home security applications (e.g., sending an alert to an ex-spouse's house under a restraining order to inform that the ex-spouse has been drinking and take appropriate precautions). It could even extend, e.g., to automatically informing law enforcement if such restraining order geo-fences have been violated.

While the above embodiments emphasize anticipation and prevention of relapse, there are also many embodiments of the present disclosure that address minimizing damage if usage of the addiction occurs. In one example embodiment, alternative transportation mechanisms are leveraged when a risk of the addict traveling while impaired is considered high. Beyond and including communicating with the addict's personal vehicle(s) and interfacing with the appropriate systems to prevent the addict from driving the vehicle, the example embodiment may also interface with systems such as Uber or Lyft to automatically request ride services when it detects that the addict is in need of such transportation. It may also interface with driverless cars or cars with that option. For example, if the addict's personal vehicle has a driverless option, the example embodiment may automatically switch the car into that mode to prevent the addict from taking control. An alternative may be to completely disable the addict's car, or any other car the addict attempts to drive (such as those with embedded breathalyzers or similar driver condition monitoring/car interfacing technologies).

Other transportation-related embodiments include, but are not limited to, communicating with rental car companies if an embodiment detects impairment; airlines to prevent drinks from being served to the addict. It also includes alerting key parties (such as spouses) when the (possibly impaired) addict is on the way to home, and activate if desired various security measures when the addict is with a certain distance of the home or other location (such as children schools) so that measures such as automatically locking the home, calling security/police, family etc. can be taken before the addict arrives at the location.

Another example embodiment of the present disclosure provides interfacing with the increasingly personalized digital media world. Digital signs/signage may be capable of communicating with personal devices to detect information about the owner in order to tailor advertising to the owner's specific needs, preferences, and desires. Other signage looks to market to common denominators with beer commercials and the like-causing distress in some alcoholics. One example embodiment may interface with public digital signage, e.g., to prevent alcoholism-related signs from appearing while the alcoholic is in the viewing vicinity, or alternatively causing uplifting, trigger-soothing related ads or messages to be displayed. The signage for use by interfaces could be coordinated, e.g., by the Addiction Server or by an application on one of the addict's devices with access to the Action Coordination Engine.

Various embodiments may address the privacy of the addict and others via a privacy engine 117 to both protect the addict's privacy—to the extent possible and/or desirable—as well as the privacy of others involved in implementing such embodiments, such as friends and service providers. As the transportation embodiment above illustrates, implementing restraints on an addict in terms of utilizing third party services and/or informing third parties of an addict's risk situation can involve privacy concerns and legal considerations. In various embodiments, a privacy engine 117 may address such matters while still providing functionality as disclosed herein. The privacy engine 117 may interact with various embodiments such as the Action Coordination engine to ensure that privacy concerns are appropriately addressed in the selection and implementation of any course of action.

One example embodiment includes sending alerts to persons in an addict's support network when the addict is near, nearing, and/or stopped at a Point of Interest—POI— (e.g., liquor store, casino, shopping mall, etc.) and/or known geographical area (e.g., drug dealing areas and sites) that may provide a temptation to the addict or indeed is the intended destination of the addict. Selection of recipients of such alerts may be based on any number of parameters such as their location (e.g., proximity to the addict), time of day, day of week, etc. The triggering of such alerts could incorporate the use of geo-fences to initiate the application(s) and/or trigger various types of functionality when the addict enters or leaves the geo-fence. This could help the addict in knowing he/she is being monitored (e.g., is being systematically supported by his/her personal, semi-anonymous, and/or anonymous safety network(s), etc.) and/or causing members of the network to actively intervene to help stop/prevent/advise/console the relapse or repetition of the addiction event. This could include generating alerts when the addict is near/nearing, and/or stopped by a person of interest, e.g., a known bad influence on the addict (e.g., see FIG. 1, etc.), etc.

Another embodiment includes providing alternative routes for navigation applications (and/or data to navigation applications that can provide alternative routes) that modify directions to avoid these kinds of proximity to the points of interests (POIs) or areas described above and other functionality described below (e.g., see FIG. 1, etc.).

Another example embodiment includes providing information/alerts to addiction means entities such as casinos and liquor stores when the location of the addict is in their proximity, so as to enable on-site activities such as refusal of service or counseling to the addict. Various embodiments may provide information to credit/debit card companies to temporarily disable the cards to prevent purchases or cash advances, and/or disable the usage of other electronic or computerized payment mechanisms such as mobile wallet technologies. Various embodiments may provide capabilities to block individual transactions when a part of that transaction includes addiction-enabling products or services. For example, grocery stores in many states allow the sale of beer, wine, and even liquor. It would be very undesirable to block a grocery store transaction by the addict just because the place he was shopping in sold alcoholic beverages in addition to many other non-alcoholic items. Various embodiments may provide a capability to tie the store's check out mechanisms (e.g., bar code scanners and the like) to the mobile payment system as well as to the data profile of the addict (see below) to detect when an addict (in this case an alcoholic) attempts to buy alcohol. An alert may be sent to the mobile payment system or perhaps directly to the grocery store's check-out system to deny the transaction. The addict would perhaps be given the opportunity to remove the alcohol from the checkout process and continue the checkout without the alcohol being included to avoid embarrassment and the like.

Another feature or aspect in some exemplary embodiments of the present disclosure includes providing an addict with a panic button or hot-key or equivalent on the addict's device(s) that could trigger some predefined functionality described herein. Such activated functionality could also be based on the location, medical state, and/or other condition of the addict, or even randomly selected.

Various exemplary embodiments may provide ability for an addict to post blogs on addiction websites describing his/her state of mind and/or other pieces of context, including location, that could help the addict in unburdening themselves and/or cause other addicts to post response blogs and/or contact the addict directly to support the addict. Various embodiments may provide linkages to book/article passages or video footage showing the author(s)/actors in addiction situations and/or describing the impact of their addiction and/or showing them in embarrassing situations and the like. Various embodiments may provide various media reminders of public figures who have seriously damaged themselves in some fashion, such as high profile actors or sports figures who seriously impacted their careers by behavior that seriously damaged their public profile and in turn their careers and finances.

Another feature or aspect in some exemplary embodiments of the present disclosure includes providing predictive analysis of potential relapse based on the addict's historical data, such as travel patterns and health data such as blood pressure, and linking them to real-time data (e.g., current location and directions; blood pressure monitors on or in the person), to anticipate and evaluate the potential for a relapse, and to initiate preventative measures, such as some of the types of alerts above or alternatives below, or even triggering a release of blood pressure medicine or other types of medicine that would be deemed appropriate in the circumstances, such as Campral or Naltrexone (e.g., alcohol containing medications, etc.). These medicines' administration could be, e.g., in the form of alerts to the addict to take it urgently or as a reminder to a periodic schedule, or even triggering the release of the appropriate dosage via implants in the addict, or even more exotic methods such as being shot with the medicine from a drone following the addict, or providing a supercharged vibrate on the mobile device that could serve as a sort of wake up call, or more benign mechanisms to the addict like changing their ring tone to the addicts favorite (or least favorite song), or launching a song on their iPod that reminds them of good/bad childhood experiences. Alerts could be sent, in various embodiments, to appropriate physicians and/or as updates to the addict's medical records. Various embodiments may provide capabilities such as functionality during the addict's sleeping period to subconsciously reinforce the addict's resolve to fight the addiction, such as special programs broadcast next to the addict's bed.

Another feature or aspect in some exemplary embodiments of the present disclosure includes providing linkages to sensors such as in-vehicle breathalyzers that can activate alerts and other functionality disclosed herein. Various embodiments may provide capabilities such as addiction-trained dogs that detect the presence/usage of the means of addiction/relapse and take preventative action such as hiding the means (a kind of reverse application of the dog getting a beer for his master). Various embodiments may provide capabilities such as affixing RFID tags on addiction means (e.g., alcohol) that trigger alerts and other disclosed functionality if the tags are moved.

Another feature or aspect in some exemplary embodiments of the present disclosure includes providing location-based alternatives via the addict's mobile device to the addict to help either passively or actively in dealing with the addiction in general and/or relapses in particular. Such alternatives include:

Alerting the addict when he/she is in the proximity of their support structure, such being near an active or soon-to-start AA meeting or other support groups that meets the needs/preferences of the addict (example: a women-only meeting), or near a member of his support network such as a sponsor, family member, or friend; linking to navigation functionality to provide the addict with directions to the support person or structure; automatically calling the nearest support person or type of support person (e.g., family member, etc.).

Providing location-based suggestions for other alternative activities by linking with a personal preference database, such as a nearby teen/youth center, church, movie theatre with a movie/movie type he likes that will start soon, bingo, a bowling alley, book store, coffee shop, and other types of alternative activities based on a database of preferences, such as self-esteem boosting activities which may include volunteering/community service. Other alternatives may include errand-running based on location, such as going to the grocery store or picking up the dry cleaning. These could be done in general while the addict's device is on and/or based on other parameters such as only during a certain day or time or geographical location, on a periodic basis, or randomly.

Providing location-based advertisements for key products and services based in whole or in part on preferences and/or templates for resisting temptation, such as bakery or coffee coupons of nearby establishments (in this example, sugar and/or coffee being considered an effective alternative to alcohol). Could include special sales for that addict only and/or for a limited time (e.g., 2 hours, etc.) on those products and services.

Another feature or aspect in some exemplary embodiments of the present disclosure includes detecting that the addict, having been located at his/her residence for a certain period of time, leaves that residence in a way or timeframe that triggers an alert to said social network or legal/public authorities. Said alert may preferably have the effect of either: 1) deterring the addict from said action (presupposing that the reason for the leaving of the residence is to indulge in the addiction); and/or 2) providing a public safety service.

Another feature or aspect in some exemplary embodiments of the present disclosure includes providing linkages with databases storing images of photos, videos, text messages, legal transgressions (proven or otherwise), and other testimonial type data that can be used to remind the addict of the consequences of their addiction, and/or be communicated to their social safety network and/or other entities, particularly in the prospect of harm or inconvenience to other individuals and/or property is deemed possible. These linkages could be of a personal nature, or of an external nature, such as DUI car crashes having nothing to do personally with the addict but serving as stark reminders to the addict of the potential consequences of their actions. These images and/or messages could be automatically sent to the addict's device and displayed in the most effect manner to gain the addict's attention.

Another feature or aspect in some exemplary embodiments of the present disclosure includes providing linkages to/reminders of loss of marriage, deteriorated connections with children, family, and friends, loss of job(s), embarrassing behavior, situations or events caused by the addict's addiction, negative financial impacts like lost opportunities or assets, and other personally negative situations experienced by the addict. Reminders could be in any form, such as photos, videos, text, testimonials, etc., and rendered to the addict via display, text, audio, 3D, 4D+, heads-up display, etc.

Another feature or aspect in some exemplary embodiments of the present disclosure includes providing linkages to medical databases that show the effect of addictions of various parts of the body, such as liver, stomach, colon, nose, and other effects such as blood clots, diabetes, etc. This information could/would be transmitted to the addict's device in various methods, e.g., voice, text, photos, video, or other methods such as heads-up-display, direct neural-to-the-brain and/or other body connections (e.g., implants or other methods of directly internally communicating with the addict, and other methods). This may include being able to display, text, and/or provide verbal reminders to the addict and/or others in the addict's network. This may also include the potential for notifications/linkages to other interested parties, such as the addict's doctors, therapists, etc.

Another feature or aspect in some exemplary embodiments of the present disclosure includes providing linkages to legal and other public records indicating personal or of an external nature of the effects of the addiction, such as DUIs, restraining orders, and the like. This may include being able to display, text, and/or provide verbal reminders to the addict and/or others in the addict's network, particularly to those in close proximity to the addict. This may also include potential for notifications/linkages with public and private safety personnel and systems in close proximity to the addict.

Another exemplary embodiment of the present disclosure includes the development and presentation via various types of user interfaces of location-based information about the above in the form of news, alerts, other presentations, etc. This presentation may be motivational and/or dissituational in nature to reinforce the need for the addict to abstain from their addiction. For example, a newsfeed could pop up as a banner ad on the addict Jane Doe's phone or Google Glass as she was nearing a liquor store on 5th and Elm Street saying "News Flash: Jane Doe laughs at the temptation of Joe's Liquor at 5th & Elm!—World Rejoices!" This would have the dual effect of a) reminding Jane she is being watched or monitored, and b) providing real-time reinforcement and praise for resisting that particularly temptation.

Another feature or aspect in some exemplary embodiments of the present disclosure includes the creation of an anonymous and/or semi-anonymous social networks, allowing users (helpers for the addiction that meet certain parameters including location proximity to the addict) to flag themselves as available to help (perhaps after achieving some sort of training) in the event that no one is available in the addict's personal social network, or as a supplement or substitute. These networks can be crowd-sourced from the community at large. The primary goal would be to empowering the addict to know that someone is just an action away if the addict needs help. The helper could choose to appear anonymously or not, as could the addict.

Another feature or aspect in some exemplary embodiments of the present disclosure includes detecting, monitoring, and/or preventing purchases and/or usage of addiction-related materials. This may include providing periodic, continuous, or random reporting of such purchases and/or purchase attempts to other interested parties on a specific, semi-anonymous, or anonymous basis.

Another feature or aspect in some exemplary embodiments of the present disclosure includes providing incentive programs and frameworks that rewards the addict for positive behavior, such as coupons for free dinner for two if the addict's behavior reached a certain positive threshold, such as not stopping at a liquor store for 30 days consecutively (verified by the application). This would entail a historical tracking/counter/points type system within the addict's application profile. This would entail methods and technologies such as periodic intensive tracking of the addict for an amount of time, such as a week or a month (or moderate tracking as a regular ongoing part of the application), and awarding points (redeemable for prizes) based on verifying going to a certain number of meetings or NOT stopping at a liquor store. This framework also has a lot of applicability for others involved. There can be support quests, where say a child has to write a letter to their estranged parent (a real letter) and if so they get X number of points, which are redeemable for products or services appropriate to that person's demographic, such as an ice cream coupon for children 10-15, or iTunes credit for persons 10-25, with appropriate controls to prevent abuse. Another aspect of incentives is a behavior-based pricing model. This could entail raising the monthly cost of the service to the addict when the addict exhibits bad or undesirable behavior (e.g., relapsing, etc.), then lowering the price and/or providing refunds when the addict exhibits good or desirable behavior over a certain period of time.

Another feature or aspect in some exemplary embodiments of the present disclosure includes providing a user interface (UI) platform to the above functionality that minimizes or reduces the actions that the addict has to take for the functionality to activate. Indeed, by using capabilities that the user does not have to provide any action to activate the functionality, particularly the use of the addict's location, various embodiments may provide ways that reduce/eliminate any reluctance on part of the addict to use the functionality. Various embodiments may provide the ability to customize the user interface for the addict to maximize the convenience and usability of the functionality based on the user's profile. For example, the UI for an alcoholic may be much different than that for a prescription drug addict which in turn may be much different than the UI for a shopaholic. They could vary by many parameters, such as gender or location (e.g., text to voice conversion could be done in a western, southern, or northeastern dialect depending on the home location of the addict, etc.). The sensors used for detecting high risk situations may be much different; means of communicating messages may be much different. Various embodiments may provide the ability to modify/customize the user interface based on multiple parameters, particularly location. Other accessory type modifications to a UI based on location also may be provided. For example, if an embodiment detects that an addict (or in this case also includes non-addicts) is in a movie theater, it may automatically switch the device to vibrate, and provide a capability that inverts the display of any messages, e.g., instead of a bright background with messages in dark colors, the background would switch to a dark one with the messages in a lighter color, thereby greatly diminishing the impact on the dark movie theater environment. This capability could be enabled by various technologies tracking the movement and location of the person (addiction not a requirement in this kind of use case), and other technologies such as detecting payment for the product or service and using the nature of that transaction (e.g., buying a movie ticket, etc.) to automatically modify the behavior/user interface of the device. The device could then be instructed to revert to its former configuration when the user/device is detected to be leaving the theater.

Another feature or aspect in some exemplary embodiments of the present disclosure includes providing an initial setup capability that minimizes actions and time by the addict to setup his/her profile to take advantage of the functionality described herein. A pre-populated profile templates may initially be used based, e.g., on a few parameters such as addiction(s), gender, age, key medical conditions such as depression, medication taken, home/work locations, key hobbies/leisure activities, key addiction triggers, and/or (for some addictions) ethnicity, etc. In addition, various embodiments may provide the addict with a number of options for setting up his/her support network. These could include manual input of individuals/groups (generally undesirable), accessing/downloading individual/group information from other applications such as Facebook/social networking apps, phone and/or email address books, local AA meeting participants, etc. The addict would then need to confirm each individual (using voice or computerized confirmation) before they would be active in the addict's profile database, plus other parameters such as type of support (e.g., alert 24 hours/day, only certain circumstances such as only when the addict is out of town, etc.). These individuals may need to be sent confirmation messages, depending on circumstances (e.g., wanting to send alerts to that user) and/or the addict's preferences, asking permission to be included in the addict's support structure. Other parameters such as allowing the use of anonymous support individuals/entities would be requested. This initial information would then be used to provide the initial profile template for the addict. This information would include flagging of location-related/addiction-related POIs, such as liquor stores within a 50-mile radius of the addict's home/work or movie theatres within a 10-mile radius. It would include key directional information such as the various routes between home and work, which could then be used to provide alternative routes to avoid addiction tempting locations/POIs and triggers and/or provide convenient access to alternative activities, plus other data.

Another feature or aspect in some exemplary embodiments of the present disclosure includes providing an ongoing profile modification capability, which could be done by one or more means or ways: manually and incrementally, such as when the addict is calling, texting, or emailing a person asking the addict if he/she would like to add them to their support structure. Various embodiments may also provide or have a learning capability, such as detecting changes in behavior or condition of the addict (e.g., changed driving patterns or elevated blood pressure, etc.), correlating the changes in the addict's behavior or condition to relapse risk factors and then modifying the activation/prioritization/type of functionality described herein. Various embodiments may include suggestions by others in the addict's support network, such as recommending a good restaurant frequented by other addicts, a new bridge game being setup, a club at the addict's high school that might be helpful to the addict, etc.

Another feature or aspect in some exemplary embodiments of the present disclosure includes providing linkages to, usage of, and combination of a wide variety of databases, including but not limited to: street/navigation databases; POI databases; satellite map databases; addiction group databases, such as AA meeting types, times, and locations; event databases (e.g., ballgames, concerts, etc.); rehab facility databases; self-help databases such as WebMD; weather databases; public safety databases (e.g., police stations, sex offender databases, etc.); geographical/terrain databases; highly specialized databases such as databases that show hot fishing or surfing locations; plus a host of individual databases such as local theater databases/listings describing the locations, showings, and times of a movie theatre chain's location in the vicinity of the addict's home or work. This may include linkages to products and services in the addict's area that could help deal with triggers particular to the addict. This may include sign-up databases for addicts in a certain area who want to be part of a local, regional, national, and/or international (even special) support network, on a personal, semi-anonymously, or anonymous basis either offering to be part of a support structure, seeking the support of a support structure, or both. These databases could be public, private, or both. Various embodiments may provide new and unique value both in the application/usage of the databases, and also in combining/integrating them in new and unique ways.

FIG. 15 depicts an example embodiment of a method for monitoring for a risk of a pre-identified behavior (e.g., pre-identified addict-related undesirable behavior, etc.). FIG. 15 also includes example triggers, priorities, and initial risk assessment/detection sensors. As shown in FIG. 15, a first step may include providing a questionnaire (e.g., on paper, online, video, etc.). Questions on the question may be designed to obtain not just facts but to also elicit an emotional response from the person (e.g., addict, etc.) answering the questionnaire. The questionnaire may be used to determine the priority/impact/severity of each drinking trigger listed as well as any other ones that might apply. A high ranking for a trigger may indicate that the person often drinks or wants to drink when this trigger occurs, whereas a low ranking for a trigger may indicate that the trigger never causes the person to drink or want to drink.

Continuing with FIG. 15, location(s)/context(s) for the addict may be extracted, such as from computers, phones, social media (including location and time stamp), etc. Location(s)/context(s) for the addict may be extracted from a third party, such as location, context-rich and/or image/photo-intensive applications, e.g., navigation, etc. After extraction of location(s)/context(s) for the addict, the method may include identifying, assessing, and prioritizing triggers, and identifying key sensors, determining sensor and other sources (e.g., key readings, values, levels, ranges, yes-no parameters, etc.) to monitor for risk. The method may also include accessing and/or using addict data sources including addict data and analytics 104 (FIG. 1), including predictive analytics data, etc. The various possible triggers shown in FIG. 15 are not necessarily independent from each other as there may be relationships between the triggers.

Another feature or aspect in some exemplary embodiments of the present disclosure includes providing the ability to anonymize the addict's identity for some or all of the above functionality, particularly (but not exclusively) for functionality that goes outside of the addict's support network, such as providing moment of value mobile coupons discussed above that would shield the addict's identity from the company providing the coupons.

More broadly, the protection of addict (and their support network) privacy is one aspect of the present disclosure. The personal data collection mechanisms described in the present disclosure can conceivably be used to track a person's movements 24/7. To prevent inappropriate use of data, the present disclosure provides new systems, methods, mechanisms, and techniques particular to how and where the data is collected, and who, how, when, and why it is used.

The present disclosure describes exemplary embodiments of new systems/methods/techniques to use location and/or context information-based security as a way to protect location and/or context information. An important premise is that such personalized location/context-based images and other prompting mechanisms are readily familiar in some way to the user without the need of memorization. At the same time, such images/mechanisms would be very hard to hack or recognizable by (ro)bots since the ability to recognize them is rooted in the user's experience—not in any sort of logical or algorithmic mechanism. Such security keys, passwords, or other security-related elements and mechanisms could be used in protecting the broader collection of location/context information. Besides the ability to protect the voluminous addict behavior data, such location-based security could be used as part of financial account password verification or reset processes, or even an extra layer of security to prevent individual household appliance or device hacking or access such as preventing fake off hacking of TVs, etc. that could become more vulnerable as the Internet of Things becomes more prevalent.

One of the important premises of the location-based privacy and security components, embodiments, and examples is that location and context, presented in a user friendly manner, requires little memorization of the image, unlike say an alphanumeric password. They are readily identifiable by the user once presented to them in some recognizable fashion. In particular, location/context can take advantage of the concept in human memory of recognition versus recall. Recognition refers to our ability to recognize an event or piece of information as being familiar, triggered or prompted from external piece of information or input. Recall designates the retrieval of a piece of information from memory without any external prompting or input. Today's passwords requiring number, letters, capital letters, and punctuation signs are examples of account/data/database keys or passwords that rely in total or significantly on a person's recall ability. Nearly all memory experts acknowledge that recognition is far easier for most humans than recall. Location-based privacy and security takes advantage of recognition, which besides being easier for a given person it much harder for others that have not experienced the piece of data recognized by the user, hence it being much harder to hack, guess, or otherwise deduce, particularly if constrained in some way, such as a time limit, etc.

FIGS. 11, 12, 13, and 14 describe examples of location/context-based elements and embodiments of protecting/verifying valid users and/or access to this information. Broadly, the capabilities illustrated by these diagrams and associated disclosure and embodiments may be referred to as location-based security and/or location-based privacy, using some form of image(s) as key(s) to locking/unlocking/securing a broader set of information, such as account information and/or location/context data collected for purposes of preventing or dealing with an addiction risk or relapse. The images are not limited to only visual/graphical items, such as photographics as the images may also or instead be visual, audio, graphical, video-based, photographic, textual, alphanumeric, and/or other types of passwords depending on the user interface. The images could be in the form of sensor readings, which often have unique values depending on the sensor. The images could be multi-dimensional, such as two-dimensional (2D), three-dimensional (3D), four-dimensional (4D), or beyond if, e.g., including time/time-lapse/time-projecting images. The images may be static (e.g., still pictures), dynamic (e.g., videos, etc.), past or present, based in memory or live streaming. Or the images may also be combinations/hybrids of the above. In whatever form in various embodiments, the location-based security/privacy images are location and/or context-based, experienced by or known to the user and/or person(s) authorized to have access to the broader information.

Location/context images can be obtained, derived, or computed from numerous sources. FIGS. 1 and 2 show a variety of location/context data collection devices, networks, sensors, and other mechanisms and sources. FIG. 11 further describes several example sources and associated types of data along with examples. FIG. 11 also describes examples of questions that can be used to prompt for passwords/keys and/or access to/resets/verifications of changes/access to key information. FIG. 11 provides an example of a user memory profile that can help tailor questions/potential answers to how that person best remembers/recognizes images. Images may be a general term that is inclusive of all forms of Q & A methods and user interfaces. Questions can be tailored based on user interfaces employed, e.g., text, photo, graphics, audio, Virtual/Augmented Reality, etc.

Figure 12:
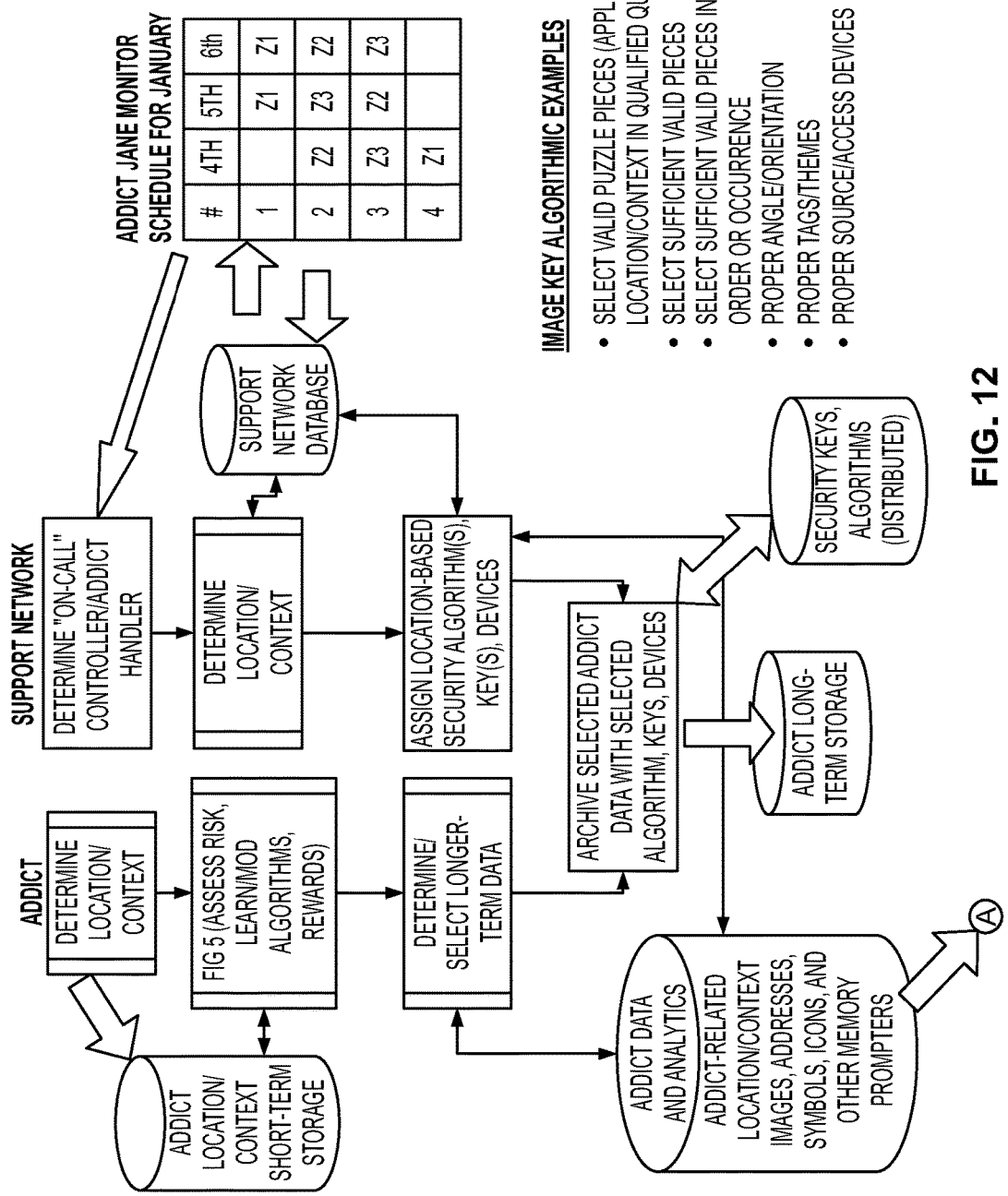
Figure 12:
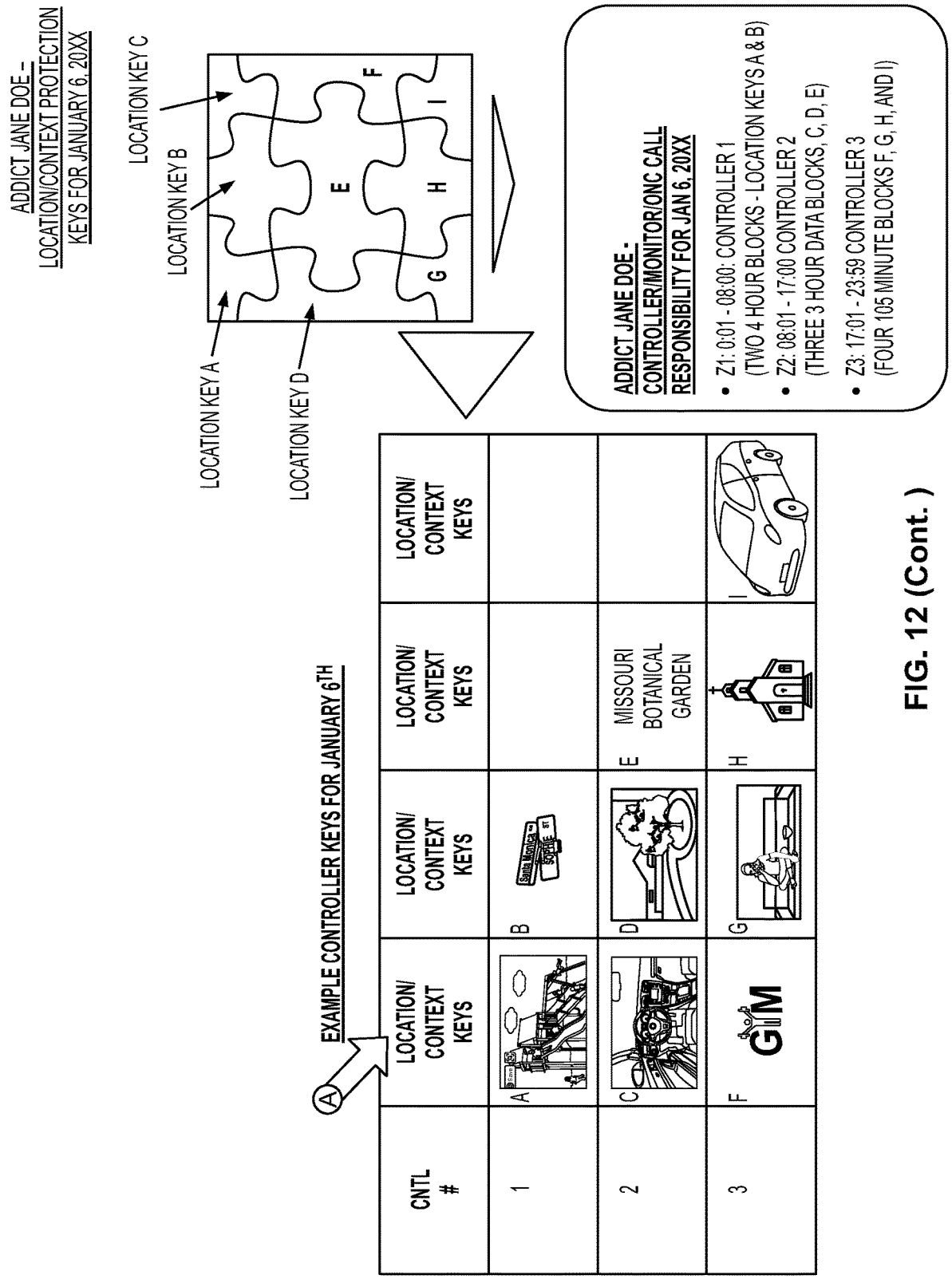
Figure 13:
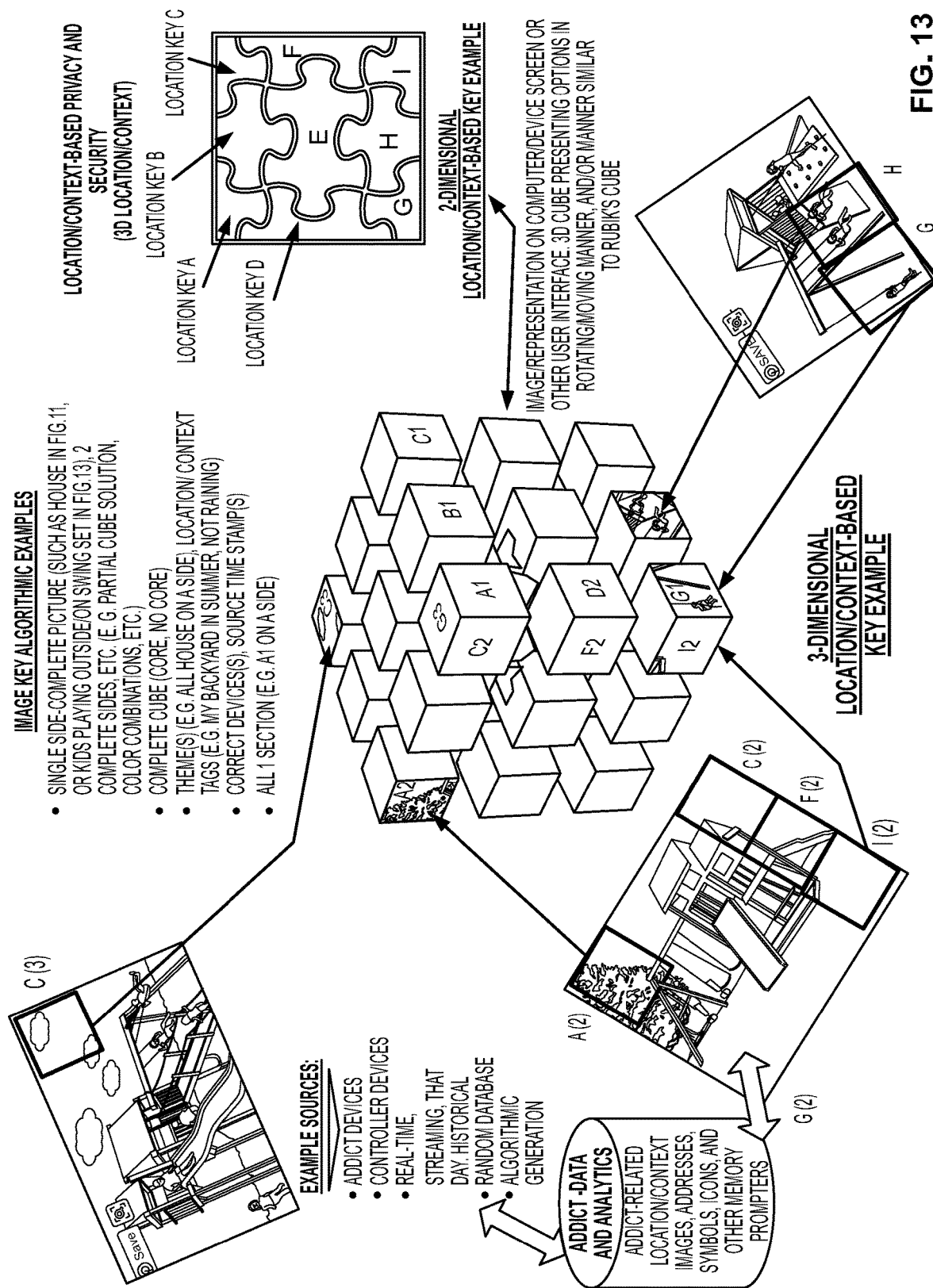

FIG. 12 provides more detail in terms of a method of how such keys might be obtained and used; examples of such keys; and algorithm examples for generating/developing/answering verification questions. FIG. 13 takes the two-dimensional oriented algorithms and examples of FIG. 12 to three dimensions, showing how 3D images (e.g., Rubik's-cube type shape, etc.) could be used to introduce more sophistication into location/context-based security. FIG. 14 shows a variety of 3D form factors and breaks out in more detail, data elements that would be captured and associated with image keys in order to provide more algorithmic and verification options.

For the figures, it is important to note the parts that devices/sensors/networks play in sourcing images, providing access to images, and in algorithmic processing of such images. A 2D photograph taken by a low-resolution smart phone of a backyard swing set has similarities with and distinct differences from a 3D image capture or video of that same swing set taken by a 3D heads-up-display camera with multi-media sound. The device, beyond capturing the time, place, and image of the location/context, also adds certain contextual elements to the image. In turn, those elements may play an important role in the ability of the user to recognize the image later when it is presented during a verification/password acceptance Q & A process.

One of the embodiments illustrated in FIG. 11 is the concept of a multiple-key or jigsaw puzzle-based key or password for location/context-based security. The jigsaw puzzle based information lock includes multiple keys to be correctly assembled in the correct order/sequence in order to provide access to any data.

For example, the overall key is that a picture of a house must be assembled. This house has been broken up into 9 separate images with 9 separate associated location/context-based keys. Each of the 9 keys were created and assigned during a particular time during which certain controllers or monitors were on-call for a particular addict.

The Location-Based Verification Examples sections of FIG. 11 describes some of these either as Verification Grid Element # or Grid #. In various embodiments, data produced and used as described in the present disclosure could be location/context images as actually experienced or seen by the device/user, or they could be representations of a location/concept. Example of questions or limitations on verification answers are also shown in FIG. 11, such as "Where you have been in the last (week, month, year, etc.)?" The use of multiple devices and/or perspectives of the same image (such as a house, daughter, etc.) would make it much more difficult for a (ro)bot and/or hacker to replicate through algorithms, analysis, or even guessing, whereas for the user it would take very little effort to recall/recognize the correct images. In the location/privacy-related examples and embodiments disclosed herein, a user may refer to a person or entity trying to gain access/validation to an account, database, data set, or other piece of information. Or, for example, a user may refer to a person and/or an entity generating such data/information. A user can be a human, computerized entity, and/or anyone or anything that has valid permission to access the information involved.

In addition, there are potentially more persons/entities involved in location/context privacy and security than just users. Certainly, data can be generated/sourced from a wide variety of mechanisms/methods/sources. In addition, control over this data does not necessarily have to be by the (primary) user or account holder. Indeed, in addiction-related embodiments in particular, different data sets can be controlled by someone other than the key user (e.g., addict, etc.). One embodiment of such in location-based security is the use of an addict monitor or controller. Such an entity can be a human (or even artificial entity) that is responsible for monitoring the addict over a certain time period. The idea is to maximize or at least increase the probability that if a relapse were to happen, there would be a person on-call that would be at least generally aware of what the addict was doing, or at least have no uncertainty that if a high-risk/relapse situation were to occur that they are #1 on the list of support persons to respond. This entity may be a human or an artificial intelligence entity that has the responsibility of being at the top of the addict support hierarchy during a given time period if the addict were to encounter a high-risk situation during that time. The general purpose of such controllers is multi-faceted: to distribute security of addict information across different entities as a general security precaution; make it progressively more difficult for hacker to access the data; and, in the case of addiction-related data provide security control to entities that are (almost literally) more sober than the actual user.

A side aspect of the controller function is that the controller's location/context would be sampled or otherwise tracked periodically for the time-period when they are on-duty. This location/context information, besides being used in identifying/locating support person if needed, could also be used to create a location/context-based password for the addict's location/context—based on the controller's location/context—during the period of time the controller was on-duty.

While the location-based security and privacy elements and embodiments described in the present disclosure are primarily intended to protect information gathered in relation to getting/keeping an addict sober, its use is not limited to such addiction-related purposes. For example, one set of embodiments of this location-based security and privacy disclosure is in using recent and/or historical location/context information as a password reset verification mechanism, to prove that a user is not a robot, and/or to verify financial transaction. In one of its simplest forms, such verification would consist of a system (or person) asking where a person was on a certain date and/or certain time. Note that this query and response mechanism could be done using any of the user interface forms described elsewhere in the present disclosure.

Below is a variety of embodiments and examples that illustrate location-based security and privacy concepts applicable to many types of situations, verification environments, and protections/access to financial, addiction-related, or other types of sensitive data. Most (but not all) such example data protection/access mechanisms have some sort of qualifiers to limit the scope of a location/context-related question or statement.

For example, Grid answers to the question could "Select the location & activities you were doing on Jul. 26, 20XX." Note that the specificity of the question/statement can be tailored to the User's Location/Context-based Privacy and Security (P/S) Memory Profile, so that questions/statements are not limited too narrowly (or broadly) for recognition purposes:

As an easy example, Grid #4 could be an image of the user's mother's house—a location and associated context (where they live currently, as it looked before after a remodel last year)—easily identifiable to the user but less so to others and unlikely to be the current image in a readily accessible databases (e.g., Zillow, Google Maps, etc.). Such images could also be taken from angles (such as the backyard) that are generally not accessible on those kinds of databases, particularly since such databases do not generally have linkages to specifically identified family members and associated belongings. Additional security could be added that requires the user to identify how the image was captured (in this case from User's Device A). It may be that a user may have many devices (particularly for an Internet of Things user), but only takes pictures from 1 or 2 devices. This fact might be known only to the valid user.

Grid #5 shows a vacation picture of the user's son on vacation in Location X doing Activity/Context of mountain climbing, taken with a Helmet Cam—also easily identifiable to the user but much less so to others. This verification question statement could be further qualified by asking for example images that "were on vacation", "shows 1 of your children", "shows mountain climbing" or "ocean", "an activity you did 20 years ago", etc.—knowledge likely known only to the user, as would the device used, which could be further obscured by using a nickname for the Helmet Cam, such as "3rd Eye" or "Gorgon".

Grid #1, shows a picture of a "North Carolina" street sign. The image may or may not have been "seen" by the user's device; rather, it is representative of whether the user had (or had not) been in North Carolina on (or around) the 7/26/XX time frame. Such an image could be generated from the raw data of a navigation app (such as the user's car #1—Device B onboard navigation system), combined with a geo-fence around the state of North Carolina that generated a database reading when the user crossed the state boundary on 7/26/XX.

Grid #2 shows a textual representation of an address visited on 7/26/XX, such as the street address of the user's mother's house in Grid #4, derived from that image's latitude/longitude through a latitude/longitude to address converter program.

Grid #3 shows an algorithmic derivative and associated graphical image that was created from the latitude/longitude centerpoint of all activity on a certain date. So in this case, the actual location/context of the user is not displayed, and used in an indirect manner, but the user could easily associate that they were a) indeed traveling overseas, b) it was in Australia, and c) it was on business (a hacker might assume it was for vacation, which in this case would be incorrect).

Grid #6 shows am image that has multiple images of past context, in this case a picture of an dining room in a former home with a now deceased pet. This could alternatively be a possible answer to questions about playing with pets in old homes contexts.

Grid #7 is an algorithmic representation of a crossroads that the user passed in a certain timeframe. Alternatively, it could be a subtle representation of a location/context, such as taking a trip with my cousin Sophie to Santa Monica Calif.

Grid #8 illustrates how an image is not necessarily photo/video/visual/graphical in nature. In this case, it is an audio clip of "California Dreaming" by the Mamas and Papas as a way of indicating a location or geo-fence, based on location information taken in this case from a mobile social networking post from Friend "e". This illustrates how images do not have to be directly sourced by or even known to a user—the key is to be recognizable to the user/person trying to access the account/data.

Grid #9 is an image pulled at random from a sample of retail visit locations, with the address matched with the store name and image (source: Internet). This could be in response to a question of where the user did NOT shop in the last week for example, or something even more subtle in response to a question of "select store(s) in a retail strip mall where you've shopped the last week", assuming the person knows that there is such a store right next to a frequent shopping destination he or she went to, even if they did not go to that specific store during the timeframe in question.

Grid #10 illustrates an image taken from an indirect source (in this case for example a child in the backseat of a car). The driver may not have known such an image was being captured, but enough detail about the driver (user) and his context is shown that he would be able to recognize key location/context questions (such as what car was this picture taken from, or what state was the car in at the time of this picture?).

Grid #11 is another example of an externally sourced image—a satellite image of a house from Google Satellite. Such images could be asked in a verification process regarding valid family member homes. It is likely only a user that is very familiar with such homesteads could quickly identify such homes, making more difficult for a bot to answer correctly.

Grid #12 shows how colloquial references to a location can be used as a verification mechanism. In this case, like Grid #'s 2 and #4, it is intended to represent the user's mother's home. This colloquial/textual representation could be used as a stand-alone answer to a verification question or be paired with other images such as asking the user to select all images related to a family member. In addition, a family tracking application such as AT&T Familymap can be used to extract colloquial names and locations of key places, such as "Mom's House", "Kids School", etc. These terms can then be paired/matched to actual or derived images of those locations, and some or all of the results presented as options in the Verification Process.

Grid #13 shows how the quality of an image (or lack thereof) can be used as a verification mechanism, under the premise that a poorer quality image will be more difficult to analyze by a bot or other hacking mechanism. Grid #13 is actually a much poorer version of the image of the user's mother's house in Grid #4. While still recognizable to the user, the image is likely to just appear as a bunch of squiggly lines to a bot or non-authorized user. Quality variations could be done in numerous different ways, including changing image fill/lines colors or solidarity (e.g., dashes instead of lines), color to black and white, pixel density, and/or circus mirror-type distortions.

Grid #14 shows a three-dimensional image of a roller coaster ride, illustrating how 3D images (including dynamic images such as video) can be used as both as a type of source data (e.g., requiring 3D-capable data capturing mechanisms) but also images where the person/entity trying to access the data has to have the correct devices to appropriately view/select the image. In some cases for example access to images could only be practically possible through viewing through 3D glasses—in effect prohibiting bots or automated/computerized mechanisms from being able to process such images.

Grid #15 extends the 3D concepts of Grid #14 even further by portraying possible verification images in a dynamic, 3D manner, such as a rotating Rubik's cube type presentation where images are not only presented in 3D but also done in a temporary, rotating manner that requires very fast decision making. This concept is elaborated on further in FIGS. 13 and 14, where solving Rubik's cube type images is required to verify an account and/or gain access to the account/data and where different portions of the cube are sources/controlled by different users/sources involved in the data collection and/or usage process.

Grid #16 illustrates the potential role and sourcing (and security and privacy concerns) associated with smart homes and the Internet of Things (IoT), as common household items such as TVs evolve beyond being dumb or one-way communications mechanisms to being able to collect, store, and transmit location/ context and other data about a user (TV viewer). The image in Grid #16 is a possible example of a picture/video that could be taken of a TV viewer by the TV itself. As shown also in FIG. 1, IoT may play a major role in collecting location/contextual data (particularly activity/behavioral data) in places/situations not historically available to such data collection. This type of household data has the potential for being particularly sensitive, and as such needs the extra protections offered by the location-based privacy and security mechanisms, systems, and methods described herein.

To successfully use the protections and security described by this location-based privacy and security, there needs to be ways of verifying, authorizing, or otherwise providing access to the very large (and often very sensitive) volumes of data collected. At its simplest, a location-based key (or password) needs to be matched to the correct image/answer in order to proceed further. There are numerous ways of matching two images to see if they are the same. Many have to do with the degree of uniqueness, e.g., do the two images share the same unusual representation or pattern—sometimes done on a pixel-by-pixel basis.

For exemplary embodiments of the present disclosure, doing exact matches are fairly straightforward, as the images being offered as a verification/password matching option may often be the exact image stored in a reference database, with few if any technical differences. Where degree of uniqueness comes into play is when certain location/contextual elements are the focus of the verification question or password sequence, such as requesting all images that show children-at-play in my backyard during summer of 20XX. In those cases, the possible images not only may not be an exact duplicate of a baseline/reference image, but there may also not be a baseline/reference image, and/or the possible correct images may seem very different to the typical viewer. In these cases, it can be subset(s) of the images that would be important—those portions of the image that determine key location/context elements, such as "children", "at play" and "summer 2000." In those cases, a person may designate the important elements, or a matching algorithm may pick out key elements, such as the presence of a swing set to be the proxy for "play", "children" being anyone under 5 feet tall (this needing a reference height), or "Summer 2000" showing trees and grass in full bloom, with a date stamp of June, July, August, or September 2000 as part of the image metadata. A statistical probability technique may also apply, such that any match with more than a 90% probability would be considered sufficient.

A new way of dealing with the variances/uncertainties of matching/verifying images that are not technically/digitally the same yet have sufficiently matching elements is location/context fingerprinting, described in the present disclosure. As background, in the wireless field, there is a concept called Radio Frequency (RF) Fingerprinting. This is a generally a location-determination method where surrounding cellular or Wi-Fi signals at a given point are measured (such as measuring signal strength, or time-differences), and those measurements stamped with a GPS location—constituting a fingerprint of that location. When a user of such a system later reports a variety of signal measurements, they can be compared to the fingerprint database, and if they match a fingerprint in the database, then that user is reported to be at the corresponding location.

A new variant of that concept is disclosed here. For example, a verification database may have many hundreds or thousands of images of a location and/or context—some drawn from/known to a user and others not. In a verification process, the verification engine could offer several images, and request the user to select the 3 that all have the same location or context in common. The common element could be any number of things—same location (home) or context (playing with my children), same location at the same point in time (summer last year), etc. It could even be which images were taken from the same (user) device—e.g., matching based on source device and/or metadata attached to the image versus the image itself. All of these examples would be relatively easy for the user to remember, and remember quickly; a hacker would have a difficult, even impossible job in deducing the correct answers. Like a physical fingerprint is only on the user's physical person, these location/context fingerprints are available only in the user's brain. A simple example of a location-based fingerprint is to have a front, side, and top image of the same object or situation that the user then has to recognize. For example, while such images of a house are readily available from various sources (e.g., Google Earth, Zillow), such different perspectives of the same object would look very different to someone without a vested interest in the property (e.g., the owner), and thus it would likely only be an owner/resident that could quickly pick out 3 such images from a collection of several, for example.

The above is another instance of the importance and effectiveness of location/context-based privacy and security in protecting against robots or bots seeking to compromise data/system security. For example, when asked to verify whether or not a person is a robot, many such existing techniques display several photos and ask the user to select those that display portions of street signs or store fronts. If the user correctly selects all frames, then they are allowed to proceed with the transaction. As an enhancement, the present disclosure could provide images of locations personal to the user. For example, a variety of storefront images could be presented to the user, and the user asked to select which ones they have been to within, say, the last 24 hours. These transactions could be selected according to a procedure, algorithm, or even randomly from the locations collected from the user during that time period. This kind of verification would deter a sophisticated robot as the validation process would be based on the user's personal experiences and not a robot's general image recognition capability. Similarly, several street signs with a real or systemically-overlaid image of a street or road could be displayed, and ask the user to select which streets/roads the user has traveled in the last week. The system could provide as much granularity as needed in selecting the roads, whereas a "week" could be very specifically 7 days, or generally several days, depending on how good the user's memory is (and which is described in their memory profile discussed shortly).

Such a query could be structured to include locations/streets/roads that the system knows definitively has not been to during the proscribed time period. This could create by a simple geo-fence-type algorithm that encapsulates a user's movements in a particularly geographical designation, such as town, city, zip code, county, or state for example, within a certain time period, and then providing other selection options clearly outside those areas during that time. A simple illustration could ask the person "have you been to O'Fallon, Illinois recently?" The system's data store would know if the user has ever been there, but such answer is not part of public record such as asking where you have lived in the past or even the model of car that you have owned. The verification is based on the user's personally experienced location/context—information unlikely to be available in other databases that are accessible by hackers.

The selection of the location transaction to base a query on could be done in a variety of ways. The selection of the preferred method could be established beforehand in user profiles, for example, giving the user choices to select locations for verification purposes based on day (e.g., Saturday), time (only in the afternoon), time period (within the last day, week, or month), historical only (only last year's locations), geography (only Missouri locations), and/or context (e.g., locations when I had been on vacation and/or clearly engaged in leisure activities). This allows the user to be prompted with locations that they are most likely to remember, yet with little or no obviousness to a hacker.

Indeed, the above could be used not just for verification or reset purposes, but as an application/system password or key itself. Every time a person logs onto Application B for example, instead of being asked for an alphanumeric-based password, it could be shown as several images—individual or parts of images, e.g., as shown in the jigsaw or Rubik's cube puzzles in FIGS. 11 and 13. Images are not limited solely to visual/graphical items. The images may be visual, audio, alphanumeric, or other types of passwords depending on the user interface, but are nonetheless referred to as images for convenience. In whatever form, the images are location and/or context-based and/or personally experienced by or known to the user. Several images could be displayed to the user, and the user may be asked to select the one(s) they have experienced at or during a selected time period. Or a time period could be displayed with images all experienced or known to the user, then the user may be asked to select the correct time-period from a list of options. An incorrect selection would be replaced by new options with a new answer that is based on the user's location/context experience or knowledge.

The user interface used in the verification/password selection process can do more besides providing a large variety of image and image-type selections—it can also enable new types of verification methods. For example, a 3D touch-type screen could enable choosing the correct images as they are raised or elevated in the view screen, and the user can touch/press those images that are correct/in the correct sequence, in a kind of virtual whack-a-mole mechanism. This concept is illustrated in FIG. 14. An example embodiment of this concept is that the user is presented with a static or rotating image (or cube) that has one or more pictures being enhanced (e.g., popped-up, etc.) every few seconds. The person trying to gain access to the data/account/system would only have, for example, 2-3 seconds to select (virtually whack) the valid option(s)—validity being dependent on the verification/authorization question or statement, such as "select all images showing your kids playing in your backyard in summer 20XX." This is an example of a question that would be relatively easy for a valid user to answer because the user could readily recognize the user's own children, own backyard, and even season/year (if, for example, the user's backyard was a landscaping mess up to Spring of that year, and a new swing set replaced the old swing set the winter of 20XX). Conversely, this would be very difficult if not impossible for a bot or other hacking-type algorithm to discern the correct answer(s).

To provide further protection, the location data used could be selected randomly from the historical data store both in time and/or place. A live, real-time, or near-live/real-time (e.g., only a few seconds, minutes, hours-old, etc.) stream or recording could also be used, requiring the user to relatively instantaneously or instantly recognize images not seen or recorded anywhere else because they are happening now or just happened.

In exemplary embodiments associated with addiction, there are additional location-based security embodiments above and beyond (or particularly tailored) to addiction-related issues and/or data sensitivity. For example, one or more specific persons may be provided with control of a location-key that is based on some personal information of the addict and/or support person(s). This key could be relatively static, changing relatively infrequently, or dynamic, changing perhaps every day or even hour. The premise is that much—even most—of an addict's data will go unused, or used very infrequently—thus it is not necessary to have a commonly-known, even easily accessible password or equivalent. Because exemplary embodiments of the present disclosure are generally centered around the prevention of relapses/usage of substance or activity, if during a given period of time there has been no usage-related activity, there is little reason to retain that information once key addict location/context/behavior information (such as rewards-eligible behavior calculations) has been extracted. Once the data has been fully used, it can then be erased in a Snapchat-like manner, or archived with a location-based password or key, or pointer to who has the password or key. Or portions of the data could be randomly selected (or selected based on the user's memory profile) and stored for future verification/location-based security purposes. Depending on the addict, addict-situation, controller or controller-situation, or other factors such as court-orders or law enforcement requirements, knowledge of and/or access to location/context-related keys could be bypassed (or enhanced) to make it easier (or more difficult) for an addict's location/context data to be readily accessed. In certain circumstances, the addict's consent could be an absolute requirement for anyone to access the data—in other circumstances (e.g., court orders) the addict's consent might not be required at all.

The duration or longevity of location/context-related data, particularly addiction-related data, is also significant. As indicated in the process flow in FIG. 12, not all location/context data would be stored indefinitely. To the contrary, once the utility of an addict's location/context data has been fully utilized—either in detecting and/or preventing and/or dealing with a high risk/relapse situation, or learning/adjusting/modifying applicable learning mechanisms, as well as rewards, there may not be any reason to (continue to) store the data and thus can be deleted in Snapchat-type fashion. On the other hand, if there is a longer-term reason to store such data (court orders, a desire by the addict to journal addiction recovery, etc.), then location/context-based privacy and security measures would be put in place.

If location/context data for an addict is indeed archived, in general it should not be easy to retrieve and be extension very difficult for non-authorized persons or programs to access. Location-based security, with different pieces of historical data protected by different location-based security mechanisms and passwords known to different persons, would achieve this high level of protection. To resurrect a 24 hour period for example may require location-based passwords from several different people—an electronic version of old-style bank lock-boxes that require multiple keys to be inserted at the same time to open the box. Instead, to retrieve the location data from February 18, 20XX for addict A, it may require location-based passwords from the three different addict controllers that were on-duty that day, as well as the addict themselves, to reassemble/reconstruct that day.

Images used in a visual matching scheme such as in FIG. 11 need not be ones actually taken in photo form by a user or otherwise captured in a graphical form. For example, if the user had been detected at being at the intersection of Santa Monica Blvd and Sophie Street within an acceptable time frame (according to the user's memory profile), a street sign could be generated showing a street intersection sign image. Such images could even be generated using even more abstract mechanisms, such as a mileage street sign showing how far to certain locations could be derived by a visited location, then displayed in visual form. For example, if a person were in Disney World in Orlando, Fla. 2 months ago, and their profile allows for vacation locations within the last year to be used, a street sign could be shown that says 204 miles to Miami, 74 miles to Tampa, etc.—those being the mileages between Orlando and those cities. Thus, an image-based location key could be generated just using a visited location or latitude/longitude.

The image selection process for the above embodiments can be simplistic or very difficult. On the simplistic end, for example, only one of several images could be valid. On the difficult end, several could be valid, but they must be selected in order of oldest to newest (or vice versa). The latter, for example, could be images (pictures, addresses, etc.) of previous home locations, pets (that were only alive at a certain property), etc. that only the user is likely to readily know in the proper sequence, yet not require little additional effort by the user to actually remember. Thus, it would be possible to create a very complex password or verification sequence, yet easy for the user to understand, and nearly impossible for an outside party to know, at least without extensive research. A time or other context-based limit to provide the answers could be included in the verification algorithm to prevent such research from successfully taking place.

Another exemplary embodiment or variation of the present disclosure uses 3 dimensional, jigsaw-type verification. As seen in FIGS. 12, 13, and 14, a location or context can be divided into numerous pieces, then scrambled similar to a (2D or 3D) jigsaw puzzle, requiring the entire puzzle to be solved, only certain pieces of it solved, or solved for a particular type of solution, theme, and/or in a given time-sequence for example. The general philosophy behind such puzzle approaches is that it becomes progressively (even exponentially) more difficult for a human/entity not-familiar with the locations/contexts involved to solve the puzzle, while being only incrementally more difficult for those humans/entities who are familiar with the locations/contexts involved.

That said, it is possible to use location-based concepts in the generation of a traditional password. For example, if the first 9 images in FIG. 11 were offered as possible answers to a verification question/statement, and there were only two correct images out of the 9, with each frame being assigned a value from 1 to 9, then a point score could be calculated based on the values assigned to each image. A simple example would be if the two correct images had a value of 3 and 7, respectively, the resulting key/password could be thirty-seven (concatenation of the values) or twenty-one (the multiple). That traditional password adding potential capitalization and/or numbers, such as "Thirtyseven37", could then be used by the various addiction (or other verification) analytical systems in accessing active data.

The various exemplary embodiments described above may provide an extremely sophisticated capability that establishes and systemically enforces privacy policies to support a balance of functionality and privacy. There are at least two main types of privacy policy scenarios that may be established and enforced. The first is where the addict voluntarily signs up for functionality as disclosed herein. For such a scenario and associated policy, many of the more severe elements of such functionality may be made optional, such as disabling payment mechanisms, etc. A second scenario is an involuntary sign up of an addict by other parties with the legal right, such as by parents of minors, via judicial judgments, etc. In such cases, the functionality to be activated may be decided by those parties with or without the addict's consent or even without their knowledge (if deemed legal). Various exemplary embodiments may support and in some cases require the coordination and integration of privacy and/or security policies and systems by a host of parties: application(s) as disclosed herein; financial entities; support group entities (e.g., AA, etc.), public safety and law enforcement entities; education entities (e.g., for teens, etc.); retail/wholesale chains and individual stores, service areas (e.g., movie theaters, etc.) and services; individuals, and the like.

Various exemplary embodiments may provide functionality specific to a given demographic. One example of this is for teenagers. Teenagers, and especially teenage addicts—regardless of their addiction (though usually drugs or alcohol)—can have triggers and influencers in their lives that are particularly distinct from other demographic categories: high school angst, peer pressure, parental pressure, academic pressure, sexuality issues, not to mention that most of the mechanisms for enabling the addiction to begin with are illegal. Also, many addicts in that age demographic have not reached the conclusion that they are an addict, let alone think they need help. They also are much more likely to be technically savvy, which can be a double-edged sword. On the one hand, they would likely be loath to give up/not use those devices/mechanisms that various embodiments may utilize (e.g., teenagers in this day and age are almost tethered at the hip with their cell phone, with one of the most often used disciplinary methods used by parents is taking away their cell phone privileges). On the other hand, teenagers are one of if not the most inventive demographic in getting around technical issues and constraints on their activities. It is anticipated that teenagers may represent a significant percentage of involuntary users of various embodiments. Accordingly, in an example embodiment, social networks may be used in detecting true friends (non-addicts or non-enablers) with those who are technically friends in an addict's network but are recognized by the addict, his family, and/or other entities (e.g., judicial system, etc.) to be a negative influence on the addict. For example, permission may be given by these friends (particularly the negative type) to transfer, copy, or otherwise apply that permission for the addict to track the friend to the application of the example embodiment. Thus, the negative friend's location could be used in the example embodiment to help the addict stay away from that so-called friend. This could be done with or without the addict's and/or the friend's permission, e.g., supporting the voluntary and involuntary privacy scenarios described above.

Unlike smoking where addiction may occur relatively immediately, alcoholism generally takes much longer and is much more nuanced in its progression, hence alcoholics may have very long periods of denial. In exemplary embodiments disclosed herein, sensors and other mechanisms may be utilized for alcoholism testing for a person consciously or not and/or with or without the person's consent.

In various exemplary embodiments of the present disclosure, various functionalities described herein may be integrated as a whole or in part, e.g., into one or more methods, mechanisms, and/or applications. While any individual element above could be implemented individually, it is anticipated that much of the value of embodiments of the present disclosure is in the integration of the above, in whole or in part, to accommodate the wide range of addiction enablers and alternatives, and the various technology platforms that could be involved. Such integration may include other applications such as family finders, social networking applications, weather monitoring, navigation applications, Facebook, Groupon, etc. Various embodiments can provide ways in which to make the most of the moment of value, e.g., at times and/or in context where an addict is in significant danger of relapsing.

That said, many features/aspects of the present disclosure are also anticipated to be of applicability to non-addicts or partially addict-related scenarios, such as persons with common medical conditions, sports enthusiasts, dating websites, law enforcement (e.g., additional functionality/flexibility beyond just GPS bracelets, providing other flexibility to the judicial system such providing innovative options to judges in DUI cases to revoke their parole if they are found to have stopped at a liquor store, etc.), medical applications, insurance applications, employee verification, medical alerts, amber alerts, suicide prevention, etc. For example, blood alcohol sensors may indicate a relapse by an alcoholic. Any one or more triggers as disclosed herein may also or instead be used to identify an increasing suicide risk and be monitored accordingly.

All of the above covers one or more addictions; a substantial portion of the addict community has more than one addiction. Also, it covers addictions that may be replaced by others, such as replacing alcohol with caffeine and/or sugar.

Exemplary embodiments are disclosed of systems and methods of using location, context, and/or one or more communication networks for monitoring for, preempting, and/or mitigating pre-identified behavior. For example, exemplary embodiments disclosed herein may include involuntarily, automatically, and/or wirelessly monitoring/mitigating undesirable behavior (e.g., addiction related undesirable behavior, etc.) of a person (e.g., an addict, a parolee, a user of a system, etc.). In an exemplary embodiment, a system generally includes a plurality of devices and/or sensors configured to determine, through one or more communications networks, a location of a person and/or a context of the person at the location; predict and evaluate a risk of a pre-identified behavior by the person in relation to the location and/or the context; and facilitate one or more actions and/or activities to mitigate the risk of the pre-identified behavior, if any, and/or react to the pre-identified behavior, if any, by the person.

The pre-identified behavior may include pre-identified addiction-related undesirable behavior, and the system may be configured to be operable for monitoring for, preempting, and/or mitigating the pre-identified addiction-related undesirable behavior. The system may be configured to determine, through the one or more communications networks, a location of an addict and/or a context of the addict at the location; predict and evaluate a risk of relapse by the addict in relation to the location and/or the context; and facilitate one or more actions and/or activities to mitigate the risk of relapse, if any, and/or react to the relapse, if any, by the addict. The system may be configured to determine whether one or more addiction triggers predetermined in the system are active or present based on the location and/or the context and/or biometric, environmental, and/or behavioral data for the person. The system may be configured to determine whether one or more addiction triggers predetermined in the system are active or present by comparing data from one or more of the plurality of devices and/or sensors with one or more settings for the person. The one or more settings for the person may include one or more of blood pressure, heart rate, skin temperature, body temperature, respiratory rate, perspiration, weight, exercise schedule, external temperature, noise loudness, and/or noise frequency. The plurality of devices and/or sensors may comprise one or more biometric, environmental, and/or behavioral sensors that provide the biometric, environmental, and/or behavioral data for the person usable by the system in determining whether one or more addiction triggers predetermined in the system are active or present. The system may be configured to receive and process feedback and to adjust the plurality of devices and/or sensors including increasing, decreasing, and/or otherwise modifying one or more of the settings and/or a frequency of data collection in response to the feedback including actions and behaviors of the person associated with the data.

The system may be configured to predict and evaluate a risk of the pre-identified behavior by the person in relation to the location and/or the context by using data from one or more of the plurality of devices and/or sensors. The one or more of the plurality of devices and/or sensors may comprise one or more biometric, environmental, and/or behavioral sensors. The one or more of the plurality of devices and/or sensors may comprise one or more of a blood pressure sensor, a breathalyzer, a blood alcohol content sensor, a thermometer, a skin temperature sensor, a breathing rate sensor, a heart rate sensor, a skin moisture sensor, an olfactory sensor, a vestibular sensor, a kinesthetic sensor, an optical sensor, a retinal scanner, a voice recognition sensor, a fingerprint sensor, a facial recognition sensor, a biogestation sensor, an acoustic sensor, a microphone, a weather sensor, a barometer, a precipitation sensor, a gyroscope, an accelerometer, and/or a compass.

The one or more communications networks comprise an Internet of Things network including one or more physical devices, items, vehicles, home appliances, and/or household items usable by the system for determining the location of the person and/or the context of the person at the location. The system may be configured to determine the location of the person via one or more of an Internet of Things network, a global positioning system, cell tower identification, cell tower triangulation, a beacon, radio frequency fingerprinting, real-time location services, Wi-Fi based location systems, radio frequency identification based location systems, a drone, crowdsourcing, and/or simultaneous localization and mapping.

The system may be configured to predict and evaluate a risk of the pre-identified behavior by the person by using the location and/or the context and one or more of biometric, environmental, and/or behavioral data of the person; voice data of the person and/or another person, including one or more of tone, inflection, cadence, tempo, and/or pre-identified words; and/or movement data, including the person's walking gate, stride, and/or direction of travel; and/or date and/or time of day; and/or historical visitation patterns of the person to predict and evaluate a risk of the pre-identified behavior by the person; and/or monitoring social media.

The system may be configured to detect and track behavior of the person via the plurality of devices and/or sensors to determine applicability and value of behavior and to provide a corresponding incentive or disincentive for the person. The system may be configured to facilitate avoidance of one or more predetermined locations by omitting the one or more predetermined locations from one or more navigation applications and/or by de-augmenting the one or more predetermined locations from one or more augmented reality applications. The system may be configured to establish one or more geo-fences for one or more predetermined locations and to provide one or more alerts when the person crosses a geo-fence to enter or exit the predetermined location corresponding to the geo-fence or otherwise violates the parameters associated with the geo-fence. The system may be configured to use the plurality of devices and/or sensors to assess a likelihood that the person is an alcoholic, drug addict, activity addict, and/or substance abuser.

The one or more communications networks may include one or more of a local network, a public network, a private network, the internet, the Internet of Things, a wireless network, a terrestrial network, a satellite network, and/or wireline network. The location of the person may be a physical location or a virtual location. The context may include a situation, an environment, and/or a state of mind of the person based on one or more of biometric, environmental, and/or behavioral data of the person.

The plurality of devices and/or sensors may include a plurality of sensors configured to monitor the location and/or the context of the person at the location. One or more of the plurality of sensors may be located in, on, and/or near the person. A plurality of interface devices may be configured to engage in interaction with the person, with one or more support persons for the person, and/or with one or more third parties in the event the system determines a relationship between the location and/or the context and one or more triggers predetermined in the system that indicates a risk of the pre-identified behavior by the person. The system may be configured to select the interaction based on the one or more triggers and the location and/or the context of the person at the location.

The system may be configured to develop and/or update a profile of the person including one or more predetermined actions to implement for the person depending on the prediction and evaluation of the risk of the pre-identified behavior by the person in relation to the location and/or the context. The person may be a parolee, and the one or more communications networks allow the system to monitor the location of the person both indoors and outdoors. The system may be configured to be usable by another one or more persons to voluntarily and/or involuntarily monitor the location of the person and/or the context of the person at the location.

The one or more actions and/or activities facilitated by the system may include one or more of requesting the person to attend a nearby addiction support meeting, visit another one or more persons in a support network, and/or travel to a predetermined location for a certain activity; and/or providing an alert to a family member, medical personnel, law enforcement, or other support person or persons; and/or disabling a vehicle of the person; and/or automatically changing operation of a vehicle of the person to driverless; and/or informing a community member or addiction sponsor of the person; and/or monitoring the location of the person and a location of one or more support network persons and determining one or more scenarios that allow one or more support persons to be dispatched to the person's location or vice versa; and/or automatically playing a voice of a family member or a friend; and/or linking and coordinating an ad hoc meeting between the person and another person, persons, or group; and/or providing a location-based alternative and/or a location-based advertisement to the person via a mobile phone; and/or provide linkages to a mobile phone that provide one or more personal and/or impersonal reminders to the person about addiction consequences.

The system may be configured to restrict and condition access to the system and/or to the person's data collected by one or more of the plurality of devices and/or sensors through the one or more communications networks based on selection of location-based data for the person from a plurality of options presented by the system for selection, the plurality of options including the location-based data and one or more other options. The system may be configured to use one or more interface devices for interfacing with the person and/or to disseminate information to/from the person and/or one or more support persons for the person. The one or more interface devices may comprise one or more of tangible and/or tactile interfaces including one or more of a display, illumination, sound, vibration, heat, and/or smell interface.

The system may be configured to detect a relationship between the location and/or the context and one or more triggers predetermined for the person as being related to the pre-identified behavior; and based on the detected relationship, use one or more interface devices, mechanisms, or techniques to interact with the person, with one or more support persons for the person, and/or with a third party.

In an exemplary embodiment, a method for monitoring for, preempting, and/or mitigating pre-identified behavior generally includes determining, via one or more devices and/or sensors across one or more communications networks, a location of a person and/or a context of the person at the location; predicting and evaluating a risk of a pre-identified behavior by the person in relation to the location and/or the context; and facilitating one or more actions and/or activities to mitigate the risk of the pre-identified behavior, if any, and/or react to the pre-identified behavior, if any, by the person.

The method may include detecting a relationship between the location and/or the context and one or more triggers predetermined for the person as being related to the pre-identified behavior; and based on the detected relationship, using one or more interface devices, mechanisms, or techniques to interact with the person, with one or more support persons for the person, and/or with a third party.

The method may include determining whether the location and/or the context correspond to a high-risk location and context, then identifying one or more potential actions and/or available support resources to mitigate the risk of the pre-identified behavior, selecting one or more actions and one or more interfaces for the person, and implementing the selected action(s) and interface(s) for the person; and/or selecting and implementing one or more actions and one or more interfaces for the person if the location and/or the context indicate an immediate high risk of the pre-identified behavior; and/or selecting and implementing one or more preventive actions for the person if the location and/or the context correspond to a trending risk of the pre-identified behavior or behaviors, and/or adjusting and continuing to monitor the person's location and context at the location.

The method may include determining, projecting, or predicting a current or future context of the person at the location by analyzing and linking real-time data and historical data for the person, the real-time and historical data including the location of the person, data from the one or more devices and/or sensors, historical context of the person at the location, behavior patterns, travel patterns, health data, and risk calculations; and/or monitoring the person's physical and mental condition via the one or more devices and/or sensors including one or more wearable sensors and/or embedded sensors.

Facilitating one or more actions and/or activities may comprise determining which one or more devices and/or sensors are in use; determining available interfaces on the one or more devices and/or sensors that are determined to be in use; determining an inventory of potential interfaces desired by selected actions and that satisfy a privacy requirement and/or live 2-way communication requirement; and selecting and implementing one or more interfaces from the inventory of potential interfaces.

The method may include determining, through the one or more communications networks, a location of an addict and/or a context of the addict at the location; predicting and evaluating a risk of relapse by the addict in relation to the location and/or the context; and facilitating one or more actions and/or activities to mitigate the risk of relapse, if any, and/or react to the relapse, if any, by the addict.

The one or more communications networks may include one or more of a local network, a public network, a private network, the internet, the Internet of Things, a wireless network, a terrestrial network, a satellite network, and/or wireline network. The location of the person may be a physical location or a virtual location. The determination of the context may be based on one or more of biometric, environmental, and/or behavioral data of the person. The pre-identified behavior may include pre-identified addiction-related undesirable behavior. The method may include monitoring for, preempting, and/or mitigating the pre-identified addiction-related undesirable behavior. The method may include determining whether one or more addiction triggers are active or present based on the location and/or the context and/or biometric, environmental, and/or behavioral data for the person.

In an exemplary embodiment, a non-transitory computer-readable storage media comprises computer-executable instructions for monitoring for, preempting, and/or mitigating pre-identified behavior, which when executed by at least one processor, cause the at least one processor to: determine, via one or more devices and/or sensors across one or more communications networks, a location of a person and/or a context of the person at the location; predict and evaluate a risk of a pre-identified behavior by the person in relation to the location and/or the context; and facilitate one or more actions and/or activities to mitigate the risk of the pre-identified behavior, if any, and/or react to the pre-identified behavior, if any, by the person.

The one or more communications networks may include one or more of a local network, a public network, a private network, the internet, and/or the Internet of Things. The location of the person may be a physical location or a virtual location. The determination of the context may be based on one or more of biometric, environmental, and/or behavioral data of the person. The pre-identified behavior may include pre-identified addiction-related undesirable behavior.

Also disclosed are exemplary embodiments of systems and methods for providing location-based security and privacy for restricting user access. In an exemplary embodiment, a system is configured to restrict and condition access to the system and/or data based on a user's selection of location-based data from a plurality of options presented by the system for selection by the user. The plurality of options include the location-based data and one or more other options that are selectable by the user.

The system may be configured to present one or more queries and/or qualifiers to prompt the user to select corresponding location-based data from the plurality of options in response to the one or more queries and/or qualifiers. The system may be configured to restrict the user's access to the system and/or data at least until the corresponding location-based data is selected that satisfies the one or more queries and/or qualifiers. The location-based data may comprise one or more images that satisfy the one or more queries and/or qualifiers. The one or more other options may comprise one or more other images that do not satisfy the one or more queries and/or qualifiers. The system may be configured to restrict the user's access to the system and/or data at least until the corresponding one or more images are selected that satisfy the one or more queries and/or qualifiers, or when the one or more other images are selected that do not satisfy the one or more queries and/or qualifiers. The system may be configured so as to not restrict the user's access to the system and/or data when the corresponding one or more images are selected that satisfy the one or more queries and/or qualifiers.

The location-based data may include a location of the user and/or a context of the user at the location as determined by the system using one or more of a plurality of user devices and/or sensors across one or more communications networks. The location-based data may comprise data obtained by the system via an Internet of Things network of physical devices, items, vehicles, home appliances, and/or household items usable by the system for determining a location of the user and/or a context of the user at the location. The location-based data may comprise one or more images based on a location and/or a context of the location to and/or known by the user, whereby the one or more images are usable by the system as one or more passwords or keys for permitting access to the user data.

The plurality of options may comprise a plurality of images presented by the system for selection by the user. The location-based data comprise one or more images based on a location and/or a context of the location to and/or known by the user. The images may comprise one or more of a visual, audio, graphical, video-based, photographic, textual, and/or alphanumeric image; a sensor reading; a static image; a dynamic image; a multidimensional image; a past image; a present image; a future image; a live streaming image; an image of a vacation destination; an image of a family member; an image of a pet; an image of a vehicle; an image of a residence; an image of a location; and/or a virtual or augmented reality image; and/or; a drawing; a distorted image; a modified image; and/or an artificially rendered image.

The system may be configured to present a multidimensional (e.g., 2D, 3D, 4D, etc.) combination puzzle that includes one or more keys and that is successfully completed when corresponding location-based data is selected from the plurality of options for the one or more keys. The system may be configured to restrict the user's access to the system and/or data at least until the successful completion of the multidimensional combination puzzle. The system may be configured to present one or more queries and/or qualifiers to prompt the user to select, for the one or more keys, the corresponding location-based data from the plurality of options in response to the one or more queries and/or qualifiers. The system may be configured such that the multidimensional combination puzzle is successfully completed when the corresponding location-based data is selected for the one or more keys that satisfy the one or more queries and/or qualifiers. The location-based data may comprise one or more images that are based on a location and/or a context of the location to and/or known by the user and that satisfy the one or more queries and/or qualifiers. The one or more other options may comprise one or more other images that do not satisfy the one or more queries and/or qualifiers.

The system may be configured such that the multidimensional combination puzzle is successfully completed when the corresponding one or more images are selected for the one or more keys that satisfy the one or more queries and/or qualifiers. The system may be configured such that the multidimensional combination puzzle comprises a three-dimensional cube that is successfully completed when the corresponding one or more images are selected for the one or more keys for at least one or more faces of the three-dimensional cube. The system may be configured to present the plurality of options to the user for selection as the one or more keys in a rotating, moving, and/or changing manner (e.g., zooming in/out, distorted, etc.) and/or for a predetermined amount of time. The system may be configured such that the multidimensional combination puzzle comprises a two-dimensional grid or a jigsaw puzzle that is successfully completed when the corresponding location-based data is selected from the plurality of options for the one or more keys in a predetermined order or sequence.

The system may be configured to present one or more queries and/or qualifiers to prompt the user to select corresponding location-based data from the plurality of options in response to the one or more queries and/or qualifiers. The location-based data may comprise one or more images that are based on a location and/or a context of the location to and/or known by the user and that satisfy the one or more queries and/or qualifiers. The one or more other options may comprise one or more other images that do not satisfy the one or more queries and/or qualifiers. The system may be configured to restrict the user's access to the system and/or data at least until the selection of the corresponding one or more images that satisfy the one or more queries and/or qualifiers and the corresponding one or more devices used to capture the corresponding one or more images.

The location-based data may comprise a plurality of different images of a location and/or context of the location to and/or known by the user. The one or more other options may comprise one or more other images. The system may be configured to present one or more queries and/or qualifiers to prompt the user to select the corresponding images of the location and/or context in response to the one or more queries and/or qualifiers. The system may be configured to restrict the user's access to the system and/or data at least until the corresponding images of the location and/or context are selected that satisfy the one or more queries and/or qualifiers. The system may be configured to present one or more queries and/or qualifiers to prompt the user to select corresponding location-based data from the plurality of options in response to the one or more queries and/or qualifiers. The location-based data may comprise one or more images that are based on a location and/or a context of the location to and/or known by the user and that satisfy the one or more queries and/or qualifiers. The one or more other options may comprise one or more other images that do not satisfy the one or more queries and/or qualifiers. The system may be configured to assign a numerical value to the one or more images and to the one or more other images. The system may be configured to use the numerical value(s) of the corresponding one or more images selected by the user that satisfy the one or more queries and/or qualifiers for generating a key or password for accessing the user data.

The location-based data may include recent and/or historical location and/or context information of the user. The system may be configured to use the recent and/or historical location and/or context information of the user for a password reset verification, to prove that a user is not a robot, and/or to verify a financial transaction.

The system may be configured to restrict and condition access to biometric data, environmental data, behavioral data, and/or location-based data for a person, obtained by the system via one or more of a plurality of devices and/or sensors through one or more communications networks, based on the user's selection of location-based data for the person from the plurality of options presented by the system for selection by the user. The user may be the person, another person, and/or an accessor.

The system may include a plurality of devices and/or sensors configured to determine, through one or more communications networks, a location of a person and/or a context of the person at the location; predict and evaluate a risk of a pre-identified behavior by the person in relation to the location and/or the context; and facilitate one or more actions and/or activities to mitigate the risk of the pre-identified behavior, if any, and/or react to the pre-identified behavior, if any, by the person. The system may be configured to restrict and condition access to data for the person, obtained via one or more of the plurality of devices and/or sensors through the one or more communications networks, based on a user's selection of location-based data for the person from the plurality of options presented by the system for selection by the user, whereby the user is the person, another person, and/or an accessor.

The system may be configured to restrict and condition access to a person's data based on the user's selection of location-based data for the person from the plurality of options presented by the system for selection by the user. The user may be the person, another person, and/or an accessor. The system may comprise a non-transitory computer-readable storage media including computer-executable instructions, which when executed by at least one processor, cause the at least one processor to present the plurality of options for selection by the user including the location-based data and the one or more other options; determine whether the user selected the location-based data from the plurality of options; and restrict access to the system and/or data at least until it is has been determined that the user selected the location-based data from the plurality of options.

In another exemplary embodiment, a method for providing security and/or privacy generally includes presenting a plurality of options for selection by a user, the plurality of options including location-based data and one or more other options; determining whether the user selected the location-based data from the plurality of options; and restricting the user's access to a system and/or data at least until it is has been determined that the user selected the location-based data from the plurality of options.

The method may include presenting one or more queries and/or qualifiers to prompt the user to select corresponding location-based data from the plurality of options in response to the one or more queries and/or qualifiers; determining whether the user selected the corresponding location-based data that satisfies the one or more queries and/or qualifiers; and restricting the user's access to the system and/or data at least until it has been determined that the user selected the corresponding location-based data that satisfies the one or more queries and/or qualifiers.

The method may include presenting one or more images that are based on a location and/or a context of the location to and/or known by the user and that satisfy the one or more queries and/or qualifiers; presenting one or more other images that do not satisfy the one or more queries and/or qualifiers; and determining whether the user selected the corresponding one or more images that satisfy the one or more queries and/or qualifiers; restricting the user's access to the system and/or data at least until it has been determined that the user selected the corresponding one or more images that satisfy the one or more queries and/or qualifiers.

In an exemplary embodiment, a non-transitory computer-readable storage media comprises computer-executable instructions for providing security and/or privacy, which when executed by at least one processor, cause the at least one processor to restrict and condition access to a system and/or data based on a user's selection of location-based data from a plurality of options presented for selection by the user, the plurality of options including the location-based data and one or more other options that are selectable by the user.

The computer-executable instructions, when executed by the at least one processor, may cause the at least one processor to present the plurality of options for selection by the user including the location-based data and the one or more other options; determine whether the user selected the location-based data from the plurality of options; and restrict the user's access to the system and/or data at least until it is has been determined that the user selected the location-based data from the plurality of options.

The computer-executable instructions, when executed by the at least one processor, may cause the at least one processor to present one or more queries and/or qualifiers to prompt the user to select corresponding location-based data from the plurality of options in response to the one or more queries and/or qualifiers; determine whether the user selected the corresponding location-based data that satisfies the one or more queries and/or qualifiers; and restrict the user's access to the system and/or data at least until it has been determined that the user selected the corresponding location-based data that satisfies the one or more queries and/or qualifiers.

The computer-executable instructions, when executed by the at least one processor, may cause the at least one processor to present one or more images that are based on a location and/or a context of the location to and/or known by the user and that satisfy the one or more queries and/or qualifiers; present one or more other images that do not satisfy the one or more queries and/or qualifiers; determine whether the corresponding one or more images are selected that satisfy the one or more queries and/or qualifiers; and restrict the user's access to the system and/or data at least until it has been determined that the user selected the corresponding one or more images that satisfy the one or more queries and/or qualifiers.

As discussed in various places earlier, triggers like Anger, Boredom, Money, Stress, and so on are those "things" which can, in turn, cause or serve as the primary catalyst for or otherwise "activate" certain (usually negative) behavior, such as an alcoholic being triggered to drink/relapse. While triggers can often be enough by themselves to "cause" or otherwise result in the (undesired) behavior, that is not always the case, particularly as many triggers are emotional in nature at least in part, and emotions tend to "blend into" or merge with other emotions (and thus triggers), and/or causing/triggering other emotions/triggers to occur, and/or vice versa. For example, Anxiety can cause/lead to/trigger Depression or vice versa. Boredom can cause/lead to/trigger Loneliness, which can, in turn, lead et al. to Depression. Kids (children) chaos can cause Noise which can result in Yelling, which can result in Anger. These are all "related triggers" to the original trigger that started the process. FIG. 16 illustrates how triggers can be "related." The practical effect of a trigger activating related triggers is a kind of emotional/trigger "snowball" that rolls over the sufferer. Some of the snowballs "picked up" after the ball starts rolling may be relatively small, or as big if not bigger than the original snowball-starting trigger, just like in the physical snowball world. This makes preempting the original "upstream" snowball (e.g., the one highest on the mountain) to begin with so critical.

In an alcoholic example, it is not uncommon for alcoholics to have somewhere between 5 and 10 (or even more) very significant or major triggers, e.g., a trigger(s) that, in and of itself or by its very nature, can individually lead to a relapse. These significant/major triggers really make the person want to (or "have to") drink, more often than not. They can make the person want to drink all by themselves, e.g., independently of anything else going on in the person's life. But they also can set off a number of "related" triggers. Using a straw-that-broke-the-camels-back metaphor, a significant/major trigger (and possibly more) can serve as the first 900 straws on the camel-relapse back that can stand 1000 until it breaks (relapses). One or more related triggers—for that person—might serve as the 101 straws that puts the camel over the top: breaks its back. And these triggers, and how much they "weigh", can depend on the context, with different triggers having different straw "weights" in different contexts. Indeed, for a given person, one trigger might be significant/major and another related trigger relatively minor in impact; in other contexts the reverse might be true, or other triggers coming into the mix in varying degrees. In effect, for different people, and even for the same person, any/all of the triggers (and others) shown in FIG. 16 might be both significant/major triggers as well as related triggers for other significant/major triggers depending on the context and the person.

This sea of interrelated triggers is a different concept than is "taught" in rehabilitation programs of all sorts. Even when traditional treatment programs go through some degree of trigger discussion, they nearly always "treat" triggers as "standalone", e.g., the focus is on the effects that a trigger has on your drinking habits (in an alcoholic example) due to that trigger all by itself. At best (worst) such treatments might incorporate the concept of "dual-diagnosis" of Alcoholism and Depression for example, or Anxiety and Depression in a more general mental health treatment program.

Unfortunately, the pressures of daily life rarely line up in such single file fashion. Certain situations in a person's daily, historical, or ongoing life can "activate" or trigger other triggers. Again, these are referred to herein as related triggers. For example, Boredom can make you Lonely, which, in turn, might make you want to go out with friends who drink (causing direct or indirect Peer Pressure), which may take you to a place where Proximity and Smell of nearby alcohol has you drooling for a Taste of alcohol to help you Escape from other problems in your life. It is incredibly difficult to defend against alcohol in all of these simultaneous/near-simultaneous circumstances. There are hundreds, even thousands of possible combinations. And many of them, in relevance, degree, impact, and combination can vary in their "snowball building" by context, making treatment far more complex. And life is complex— what further makes determining/diagnosing/treatment so difficult is that many triggers often "attack" at the same time or nearly, and/or occur so often in conjunction with related triggers that it sometimes becomes impossible to sort out the different triggers involved, and what is a "cause" and what is an "effect".

To add even more complexity, a person's defenses, such as an alcoholic's defenses, may be weaker for some triggers than others. Worse still the strength of the person's defense may vary depending on the hour of the day, day of the week, personal living environment at any given time, how their day at the job went, and so on. In total, this complexity of trigger/related trigger relationships and variability of how and when they attack makes it almost impossible to build a single defense that works against all of a person's vulnerabilities all of the time—a much more sophisticated set of systems, methods/processes, and mechanisms are needed—examples of which are disclosed herein.

Exemplary embodiments are disclosed of systems and methods for monitoring for and lowering the risk of addiction-related or restriction violation-related behavior(s). In exemplary embodiments, a system comprises a plurality of devices, sensors, and communication network(s). The system is configured to determine, through a plurality of measurements/readings taken by the plurality of devices, sensors, and communication network(s), behavior(s) of at least one person and (a) context(s) associated with the behavior(s) of the at least one person; or (b) location and the context(s) associated with the behavior(s) of the at least one person. The system is configured to analyze the measurements/readings, the behavior(s) of the at least one person, and (a) the context(s) associated with the behavior(s) of the at least one person or (b) the location and the context(s) associated with the behavior(s) of the at least one person at the location, to thereby determine a risk of an addiction-related or restriction violation-related behavior(s) of the at least one person relative to a trigger threshold(s). The system is configured to facilitate one or more actions to lower the risk of the addiction-related or restriction violation-related behavior(s) associated with a trigger(s) from reaching or exceeding the trigger threshold(s) associated with the addiction-related or restriction violation-related behavior(s) before the addiction-related or restriction violation-related behavior occurs. The plurality of devices, sensors, and communication network(s) are configured for monitoring noise level, yelling and/or speech of the at least one person, skin and/or body temperature of the at least one person, and ambient temperature. The system is configured to determine that an Anger trigger for the at least one person is active, in danger of becoming active, or imminent based on the measurements/readings of the noise level, yelling and/or speech of the at least one person, the skin and/or body temperature of the at least one person, and the ambient temperature.

In exemplary embodiments, the system is configured to monitor result(s) of the one or more actions to thereby determine effectiveness of risk lowering action(s) and determine modification(s), if any, to profile parameter(s) of the at least one person, risk determination algorithm(s) and/or measurements/readings taken by the plurality of devices, sensors, and communications network(s) relative to the trigger(s) and/or the addiction-related or restriction violation-related behavior(s) of the at least one person.

In exemplary embodiments, the system is configured to determine whether any other trigger(s) related to the Anger trigger for the at least one person is active, in danger of becoming active, or imminent, including one or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

By way of example, the Despair trigger may be a combination between Depression, Victim, Powerlessness/Resentment, and Frustration, which individually may be relatively minor but collectively may be significant, e.g., cause a person to rage leading to a mass shooting incident or alcohol binging, etc. In this sense, the Despair trigger is a bit different than that caused by Frustration alone, for example.

By way of further example, the Information Overload/Snowball Effect trigger may be active, in danger of becoming active, or imminent when a person is being bombarded on social media on a topic. While any individual social media post might be minor, the sheer volume of numerous social media posts may slowly cause the person to rage, which may result in the person making inappropriate social media posts in Anger (and possibly reaching for a drink). When the system determines that the Information Overload/Snowball Effect trigger for the person is active, in danger of becoming active, or imminent, the system may proactively freeze or lock the person's computer, smartphone or other device used to access social media, e.g., to prevent the person from losing self-control and/or to prevent the person from making inappropriate social media posts in Anger, etc. Or, for example, the system may screen, filter, edit, or otherwise inhibit or prevent unwise content from being posted by the person for whom it has been determined that the Information Overload/Snowball Effect trigger is active, in danger of becoming active, or imminent. Content being posted could also be automatically delayed/buffered to prevent immediate posting, requiring a time period to pass and/or active manual effort (perhaps after screening by another person or automatic screening program) before the original content is actually allowed to post on the social media application. Exemplary embodiments may be configured such that negative posts (e.g., bad posts, mean posts, etc.) trigger preemptive/de-escalating return or interim posts from the automated system(s) (e.g. "you seem upset, are you sure you want to post that?", etc.), the automated system(s) may automatically connect the person to a suicide or anger prevention hotline, may automatically flag to a close friend or relative that the person is very upset (e.g., would you like to call the person now?), or suggest to the person to call a relative, sponsor, parole officer, etc. as a preemptive measure. Such automation would be a useful mechanism not only for addicts and parolees, but other persons who want to self-filter their social media activities This could also be a pre-emptive tool for people susceptible to suicide or having been put on a red flag watch list for gun control purposes, and want a way to make sure they don't trigger extra scrutiny under the watch list rules, or even a way of monitoring their activities such that they can be cleared of being flagged if they are "good" on social media for a predetermined number of months. In other words, this may provide a way to deal with and provide a recourse to a person being (potentially unfairly) flagged under red flag laws.

The Resentment trigger may also comprise a trigger at the core of violence possibilities. Similar to Despair, Resentment may also be caused by a combination of related triggers again varying by the individual and context. Resentment may also be a significant contributor to, and output from, social media snowballing.

Exemplary embodiments may be configured for monitoring for various triggers and combinations therefor (e.g., Despite trigger, Self-Loathing trigger, Resentment trigger, etc.), e.g., with a focus on red flag laws, suicide preemption, mass violence preemption, etc. In exemplary embodiments, monitoring for resentment includes paying careful attention and measurement of not only individual related (input) triggers, but determination as to what will be the mix of the triggers (and the contexts) that may significantly increase the individual to a very high risk status. But, at the same time, the risk of abuse of the red flag laws may be problematic, e.g., an unhappy ex may red flag an ex by calling in a report of a fake incident, etc. Accordingly, exemplary embodiments may be configured for monitoring people to prevent false triggering of red flag laws or in situations where it appears persons were incorrectly flagged (or the persons got better) have them removed from the "blacklists" by monitoring good behavior. On the social media front, resentment can be problematic as a large number of social media posts are intended to anger people and build resentment about certain topics or people.

In exemplary embodiments, the plurality of devices, sensors, and communication network(s) are configured for monitoring proximity of the at least one person to one or more other persons. The system is configured to determine that the Anger trigger for the at least one person is active, in danger of becoming active, or imminent based on the measurements/readings of the noise level, yelling and/or speech of the at least one person, the skin and/or body temperature of the at least one person referenced to the ambient temperature, and proximity of the at least one person to the one or more other persons.

In exemplary embodiments, the system is configured to determine that the Anger trigger for the at least one person is active, in danger of becoming active, or imminent based on the measurements/readings of a change in the noise level, yelling and/or speech of the at least one person and a change in the skin and/or body temperature of the at least one person referenced to the ambient temperature.

In exemplary embodiments, the plurality of devices, sensors, and communication network(s) are configured for monitoring ambient noise level. The system is configured to determine that the Anger trigger for the at least one person is active, in danger of becoming active, or imminent based on the measurements/readings of a change in the noise level, yelling and/or speech of the at least one person referenced to the ambient noise level and/or a change in the skin and/or in body temperature of the at least one person referenced to the ambient temperature.

In exemplary embodiments, the plurality of devices, sensors, and communication network(s) are configured for monitoring blood pressure of the at least one person and ambient noise level. The system is configured to determine that the Anger trigger for the at least one person is active, in danger of becoming active, or imminent based on the measurements/readings of a change in the noise level, yelling and/or speech of the at least one person referenced to the ambient noise level, a change in the skin and/or body temperature of the at least one person referenced to the ambient temperature, and/or a change in blood pressure of the at least one person.

In exemplary embodiments, a system comprises a plurality of devices, sensors, and communication network(s). The system is configured to determine, through a plurality of measurements/readings taken by the plurality of devices, sensors, and communication network(s), behavior(s) of at least one person and (a) context(s) associated with the behavior(s) of the at least one person; or (b) location and the context(s) associated with the behavior(s) of the at least one person. The system is configured to analyze the measurements/readings, the behavior(s) of the at least one person, and (a) the context(s) associated with the behavior(s) of the at least one person or (b) the location and the context(s) associated with the behavior(s) of the at least one person at the location, to thereby determine a risk of an addiction-related or restriction violation-related behavior(s) of the at least one person relative to a trigger threshold(s). The system is configured to facilitate one or more actions to lower the risk of the addiction-related or restriction violation-related behavior(s) associated with a trigger(s) from reaching or exceeding the trigger threshold(s) associated with the addiction-related or restriction violation-related behavior(s) before the addiction-related or restriction violation-related behavior occurs. The plurality of devices, sensors, and communication network(s) are configured for monitoring skin and/or body temperature of the at least one person and ambient temperature. The system is configured to determine that an Anger trigger for the at least one person is active, in danger of becoming active, or imminent based on the measurements/readings of a change in the skin and/or body temperature of the at least one person referenced to the ambient temperature.

In exemplary embodiments, the system is configured to monitor result(s) of the one or more actions to thereby determine effectiveness of risk lowering action(s) and determine modification(s), if any, to profile parameter(s) of the at least one person, risk determination algorithm(s) and/or measurements/readings taken by the plurality of devices, sensors, and communications network(s) relative to the trigger(s) and/or the addiction-related or restriction violation-related behavior(s) of the at least one person.

In exemplary embodiments, the system is configured to determine whether any other trigger(s) related to the Anger trigger for the at least one person is active, in danger of becoming active, or imminent, including one or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

In exemplary embodiments, the plurality of devices, sensors, and communication network(s) are configured for monitoring ambient noise level. The system is configured to determine that the Anger trigger for the at least one person is active, in danger of becoming active, or imminent based on the measurements/readings of a change in the skin and/or body temperature of the at least one person referenced to the ambient temperature and a change in the noise level, yelling and/or speech of the at least one person referenced to the ambient noise level.

In exemplary embodiments, the plurality of devices, sensors, and communication network(s) are configured for monitoring proximity of the at least one person to one or more other persons. The system is configured to determine that the Anger trigger for the at least one person is active, in danger of becoming active, or imminent based on the measurements/readings of a change in the skin and/or body temperature of the at least one person referenced to the ambient temperature and proximity of the at least one person to the one or more other persons.

In exemplary embodiments, the plurality of devices, sensors, and communication network(s) are configured for monitoring blood pressure of the at least one person. The system is configured to determine that the Anger trigger for the at least one person is active, in danger of becoming active, or imminent based on the measurements/readings of a change in the skin and/or body temperature of the at least one person referenced to the ambient temperature and a change in blood pressure of the at least one person.

In exemplary embodiments, a system comprises a plurality of devices, sensors, and communication network(s). The system configured to determine, through a plurality of measurements/readings taken by the plurality of devices, sensors, and communication network(s), behavior(s) of at least one person and (a) context(s) associated with the behavior(s) of the at least one person; or (b) location and the context(s) associated with the behavior(s) of the at least one person. The system is configured to analyze the measurements/readings, the behavior(s) of the at least one person, and (a) the context(s) associated with the behavior(s) of the at least one person or (b) the location and the context(s) associated with the behavior(s) of the at least one person at the location, to thereby determine a risk of an addiction-related or restriction violation-related behavior(s) of the at least one person relative to a trigger threshold(s). The system is configured to facilitate one or more actions to lower the risk of the addiction-related or restriction violation-related behavior(s) associated with a trigger(s) from reaching or exceeding the trigger threshold(s) associated with the addiction-related or restriction violation-related behavior(s) before the addiction-related or restriction violation-related behavior occurs. The plurality of devices, sensors, and communication network(s) are configured for monitoring noise level, yelling and/or speech of the at least one person and ambient noise level. The system is configured to determine that an Anger trigger for the at least one person is active, in danger of becoming active, or imminent based on the measurements/readings of a change in the noise level, yelling and/or speech of the at least one person referenced to the ambient noise level.

In exemplary embodiments, the system is configured to monitor result(s) of the one or more actions to thereby determine effectiveness of risk lowering action(s) and determine modification(s), if any, to profile parameter(s) of the at least one person, risk determination algorithm(s) and/or measurements/readings taken by the plurality of devices, sensors, and communications network(s) relative to the trigger(s) and/or the addiction-related or restriction violation-related behavior(s) of the at least one person.

In exemplary embodiments, the system is configured to determine whether any other trigger(s) related to the Anger trigger for the at least one person is active, in danger of becoming active, or imminent, including one or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

In exemplary embodiments, the plurality of devices, sensors, and communication network(s) are configured for monitoring skin and/or body temperature of the at least one person and ambient temperature. The system is configured to determine that an Anger trigger for the at least one person is active, in danger of becoming active, or imminent based on the measurements/readings of a change in the noise level, yelling and/or speech of the at least one person referenced to the ambient noise level and a change in the skin and/or body temperature of the at least one person referenced to the ambient temperature.

In exemplary embodiments, the plurality of devices, sensors, and communication network(s) are configured for monitoring proximity of the at least one person to one or more other persons. The system is configured to determine that the Anger trigger for the at least one person is active, in danger of becoming active, or imminent based on the measurements/readings of a change in the noise level, yelling and/or speech of the at least one person referenced to the ambient noise level and proximity of the at least one person to the one or more other persons.

In exemplary embodiments, the plurality of devices, sensors, and communication network(s) are configured for monitoring blood pressure of the at least one person. The system is configured to determine that the Anger trigger for the at least one person is active, in danger of becoming active, or imminent based on the measurements/readings of a change in the noise level, yelling and/or speech of the at least one person referenced to the ambient noise level and a change in blood pressure of the at least one person.

In exemplary embodiments, a system comprises a plurality of devices, sensors, and communication network(s). The system is configured to determine, through a plurality of measurements/readings taken by the plurality of devices, sensors, and communication network(s), behavior(s) of at least one person and (a) context(s) associated with the behavior(s) of the at least one person; or (b) location and the context(s) associated with the behavior(s) of the at least one person. The system is configured to analyze the measurements/readings, the behavior(s) of the at least one person, and (a) the context(s) associated with the behavior(s) of the at least one person or (b) the location and the context(s) associated with the behavior(s) of the at least one person at the location, to thereby determine a risk of an addiction-related or restriction violation-related behavior(s) of the at least one person relative to a trigger threshold(s). The system is configured to facilitate one or more actions to lower the risk of the addiction-related or restriction violation-related behavior(s) associated with a trigger(s) from reaching or exceeding the trigger threshold(s) associated with the addiction-related or restriction violation-related behavior(s) before the addiction-related or restriction violation-related behavior occurs. The system is configured to determine that a first trigger for the at least one person is active, in danger of becoming active, or imminent based on the measurements/readings. And the system is configured to determine whether any other trigger(s) related to the first trigger for the at least one person is also active, in danger of becoming active, or imminent based on the measurements/readings.

In exemplary embodiments, the first trigger comprises an Anger trigger. And the system is configured to determine whether any other trigger(s) related to the Anger trigger for the at least one person is active, in danger of becoming active, or imminent based on the measurements/readings. In such exemplary embodiments, the system may be configured to determine whether any one or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger that are related to the Anger trigger for the at least one person is active, in danger of becoming active, or imminent.

In exemplary embodiments, the first trigger comprises an PTSD (Post Traumatic Stress Disorder) trigger. And the system is configured to determine whether any other trigger(s) related to the PTSD trigger for the at least one person is active, in danger of becoming active, or imminent based on the measurements/readings. In such exemplary embodiments, the system may be configured to determine whether any one or more of a Noise trigger (e.g., noise level referenced to the ambient noise level, etc.), an Information Overload/Snowball Effect trigger, other trigger(s) that are related to the PTSD trigger for the at least one person is active, in danger of becoming active, or imminent. Exemplary embodiments may be configured with a preemptive filter in what a person can see on social media when their risk of being triggered (on any trigger) reaches a certain level, e.g., implementing social media censorship including not just on what the person writes but also what the person sees when a person reaches a certain risk threshold.

In exemplary embodiments, the first trigger comprises a Self-Loathing trigger. And the system is configured to determine whether any other trigger(s) related to the Self-Loathing trigger for the at least one person is active, in danger of becoming active, or imminent based on the measurements/readings. The related triggers may relatively small or insignificant individually and may change by person and/or by context. For example, for one person at one time it could be a combination of "passive" triggers (and thus trending towards suicide), which passive triggers may include powerlessness, victim, depression, and guilt for example. Or in other persons/contexts, more "active" related triggers could lend themselves towards violence, such as guilt (e.g., lost opportunities, bad deeds leading to a what-the-hell attitude towards doing worse deeds, etc.), frustration (at the world and myself, or specific individuals), victim, anger, snowball effect, etc. The context for the same combination of triggers might cause different results—alone by yourself perhaps a withdrawing into the world, with the "worst" being attempted suicide, and in others (having supposedly been bullied at school recently, an extra-intensive form of Peer Pressure/Social Relationships) combined with victim and powerlessness, leading to shootings of others. In either case being combined with an "opportunistic" context (e.g., easy access to a gun, etc.) it could lead to suicide, violence to others, or both.

Accordingly, some triggers may be entirely dependent on the related triggers versus major triggers that stand on their own and also cause other related triggers. Exemplary embodiments disclosed herein may thus be configured to monitor for a combination of particular triggers that, while individually small, have a particularly catastrophic effect when combined. This may be akin to a unique combination of relatively benign chemicals (when by themselves or in safe combinations) coming together in the right "formula" to cause a major explosion—the explosion would not happen unless all the circumstances (combination of triggers and context(s)) were just right. Exemplary embodiments may also be configured to take pre-emptive action(s) (e.g., suicide and/or violence pre-emption, etc.) when the combination of particular triggers for the at least one person are active, in danger of becoming active, or imminent based on the measurements/readings.

Exemplary embodiments may also be configured for pre-emptive proactive deletion of location/contextual records based on location and/or context for the at least one person. Exemplary embodiments may also or alternatively be configured to detect when such deletion of records has been done or is attempting to be done, to (for example) prevent destruction of records in a lawsuit.

In exemplary embodiments, the plurality of devices, sensors, and communication network(s) are configured for monitoring skin and/or body temperature of the at least one person and ambient temperature. The system is configured to determine that the first trigger for the at least one person is active, in danger of becoming active, or imminent based on the measurements/readings of a change in the skin and/or body temperature of the at least one person referenced to the ambient temperature.

In exemplary embodiments, the plurality of devices, sensors, and communication network(s) are configured for monitoring noise level, yelling and/or speech of the at least one person and ambient noise level. The system is configured to determine that the first trigger for the at least one person is active, in danger of becoming active, or imminent based on the measurements/readings of a change in the noise level, yelling and/or speech of the at least one person referenced to the ambient noise level.

In exemplary embodiments, the system is configured to monitor result(s) of the one or more actions to thereby determine effectiveness of risk lowering action(s) and determine modification(s), if any, to profile parameter(s) of the at least one person, risk determination algorithm(s) and/or measurements/readings taken by the plurality of devices, sensors, and communications network(s) relative to the trigger(s) and/or the addiction-related or restriction violation-related behavior(s) of the at least one person.

In exemplary embodiments, a system comprises a plurality of devices, sensors, and communication network(s) configured for monitoring noise level, yelling and/or speech of at least one person, skin and/or body temperature of the at least one person, and ambient temperature. The system is configured to determine, through a plurality of measurements/readings taken by the plurality of devices, sensors, and communication network(s), that an Anger trigger for the at least one person is active, in danger of becoming active, or imminent based on the measurements/readings of the noise level, yelling and/or speech of the at least one person, the skin and/or body temperature of the at least one person, and the ambient temperature.

In exemplary embodiments, the system is configured to determine, through the plurality of measurements/readings taken by the plurality of devices, sensors, and communication network(s), behavior(s) of at least one person and (a) context(s) associated with the behavior(s) of the at least one person; or (b) location and the context(s) associated with the behavior(s) of the at least one person.

In exemplary embodiments, the system is configured to analyze the measurements/readings, the behavior(s) of the at least one person, and (a) the context(s) associated with the behavior(s) of the at least one person or (b) the location and the context(s) associated with the behavior(s) of the at least one person at the location, to thereby determine a risk of an addiction-related or restriction violation-related behavior(s) of the at least one person relative to a trigger threshold(s).

In exemplary embodiments, the system is configured to facilitate one or more actions to lower the risk of the addiction-related or restriction violation-related behavior(s) associated with a trigger(s) from reaching or exceeding the trigger threshold(s) associated with the addiction-related or restriction violation-related behavior(s) before the addiction-related or restriction violation-related behavior occurs.

In exemplary embodiments, the system is configured to monitor result(s) of the one or more actions to thereby determine effectiveness of risk lowering action(s) and determine modification(s), if any, to profile parameter(s) of the at least one person, risk determination algorithm(s) and/or measurements/readings taken by the plurality of devices, sensors, and communications network(s) relative to the trigger(s) and/or the addiction-related or restriction violation-related behavior(s) of the at least one person.

In exemplary embodiments, the system is configured to determine whether any other trigger(s) related to the Anger trigger for the at least one person is active, in danger of becoming active, or imminent, including one or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

In exemplary embodiments, the plurality of devices, sensors, and communication network(s) are configured for monitoring proximity of the at least one person to one or more other persons. The system is configured to determine that the Anger trigger for the at least one person is active, in danger of becoming active, or imminent based on the measurements/readings of the noise level, yelling and/or speech of the at least one person, the skin and/or body temperature of the at least one person referenced to the ambient temperature, and proximity of the at least one person to the one or more other persons.

In exemplary embodiments, the system is configured to determine that the Anger trigger for the at least one person is active, in danger of becoming active, or imminent based on the measurements/readings of a change in the noise level, yelling and/or speech of the at least one person and a change in the skin and/or body temperature of the at least one person referenced to the ambient temperature.

In exemplary embodiments, the plurality of devices, sensors, and communication network(s) are configured for monitoring ambient noise level. The system is configured to determine that the Anger trigger for the at least one person is active, in danger of becoming active, or imminent based on the measurements/readings of a change in the noise level, yelling and/or speech of the at least one person referenced to the ambient noise level and/or a change in the skin and/or in body temperature of the at least one person referenced to the ambient temperature.

In exemplary embodiments, the plurality of devices, sensors, and communication network(s) are configured for monitoring blood pressure of the at least one person and ambient noise level. The system is configured to determine that the Anger trigger for the at least one person is active, in danger of becoming active, or imminent based on the measurements/readings of a change in the noise level, yelling and/or speech of the at least one person referenced to the ambient noise level, a change in the skin and/or body temperature of the at least one person referenced to the ambient temperature, and/or a change in blood pressure of the at least one person.

In exemplary embodiments, the system is configured to restrict and condition access to data for the at least one person collected by the plurality of devices, sensors, and communication network(s), based on a user's selection of location-based and/or context-based data from a plurality of options presented by the system for selection by the user, the plurality of options including the location-based and/or context-based data and one or more other options that are selectable by the user. The system is configured to: in response to a receipt of a request for access by the user to data for the at least one person, present the plurality of options for selection by the user and one or more queries and/or qualifiers to prompt the user to select at least one of the plurality of options in response to the one or more queries and/or qualifiers; determine whether the user selected the location-based and/or context-based data from the plurality of options that satisfies the one or more queries and/or qualifiers; restrict the user's requested access to the data for the at least one person if it is determined that the user did not select the location-based and/or context-based data that satisfies the one or more queries and/or qualifiers; and allow the requested access by the user to the data for the at least one person if it is determined that the user selected the location-based and/or context-based data that satisfies the one or more queries and/or qualifiers. The user may be the at least one person, another person, and/or an accessor. The location-based and/or context-based data may include the location of the user and the context of the user at the location.

In exemplary embodiments, the system is configured to analyze the measurements/readings in conjunction with a personalized profile(s) for the at least one person to determine a level or degree of the behavior(s) for the at least one person, which analysis is usable by the system in determining the risk of the addiction-related or restriction violation related behavior(s) of the at least one person relative a trigger threshold(s).

In exemplary embodiments, the system is configured to allow additions, deletions, and modifications to the addiction-related or restriction violation-related behavior, the trigger(s), and/or the trigger threshold(s) of the at least one person.

In exemplary embodiments, the system is configured to determine whether any of the trigger(s) for the at least one person is active or present by analyzing one or more settings for the at least one person with the measurements/readings taken by the plurality of devices, sensors, and communication network(s). The one or more settings for the at least one person include one or more of blood pressure, heart rate, skin temperature, body temperature, respiratory rate, perspiration, weight, exercise schedule, external temperature, noise levels/loudness, and noise types/frequency(ies). The system is configured to: receive and process feedback including the context(s) and/or assessment of the risk of the addiction-related or restriction violation-related behavior(s) of the at least one person relative to a trigger threshold(s); and in response to the feedback, adjust the plurality of devices, sensors, and communications network(s) including modifying one or more of the settings, increasing or decreasing a frequency of data collection, modifying how data is collected, and modifying type of data collected.

In exemplary embodiments, the system is configured to implement one or more actions to change the behavior(s) associated with a trigger(s) such that the risk of the addiction-related or restriction violation-related behavior(s) associated with the trigger(s) falls below the trigger threshold(s) associated with the addiction-related or restriction violation-related behavior(s) behavior(s).

In exemplary embodiments, the plurality of devices, sensors, and communication network(s) comprise a plurality of interface devices configured to engage in interaction with the at least one person, with one or more support persons for the at least one person, with one or more third parties, and/or with one or more other systems. The system is configured to select and implement the interaction to lower the risk of the addiction-related or restriction violation-related behavior(s) based on a personalized profile(s) for the at least one person, the trigger(s), the behavior(s), and/or the context.

In exemplary embodiments, the system is configured to select, recommend, and/or implement one or more actions from a plurality of available actions based on a determination that the implementation of the selected one or more actions will lower the risk of the addiction-related or restriction violation-related behavior(s) based on a personalized profile(s) for the at least one person, the trigger(s), the behavior(s), and/or the context. The one or more actions selected and implemented by the system may include a notification(s) of the risk of the addiction-related or restriction violation-related behavior(s) and an instruction(s) for lowering the risk of the addiction-related or restriction violation-related behavior(s) before the addiction-related or restriction violation-related behavior(s) occurs.

In exemplary embodiments, the context(s) associated with the behavior(s) of the at least one person includes at least three or more 5W1H (who, what, when, where, why, how) attributes. The context(s) associated with the behavior(s) of the at least one person may include at least one environmental condition.

In exemplary embodiments, the context(s) associated with the behavior(s) of the at least one person includes: where is the location of the at least one person; when the at least one person is at the location; and an environmental condition at the location.

In exemplary embodiments, the context(s) associated with the behavior(s) of the at least one person comprises one or more of a situation, an environmental condition, and a state of mind of the at least one person.

In exemplary embodiments, the context(s) associated with the behavior(s) of the at least one person comprises: a situation and an environmental condition; an environmental condition and a state of mind of the at least one person; a situation and a state of mind of the at least one person; or a situation, an environmental condition, and a state of mind of the at least one person.

In exemplary embodiments, the context(s) associated with the behavior(s) of the at least one person includes: why an addict is at the location; who (if anyone) is virtually and/or actually with the addict at the location or nearby the location within audible, visual, and/or electronic detection range of the devices, sensors, and/or communication network(s); what the addict is doing at the location; when the addict is at the location; and how the addict got to the location and/or plans to leave the location.

In exemplary embodiments, the context(s) associated with the behavior(s) of the at least one person includes at least three or more of: where is the location of the at least one person; why the at least one person is at the location; who (if anyone) is virtually and/or actually with the at least one person at the location or nearby the location within audible, visual, and/or electronic detection range of the devices, sensors, and/or communication network(s); what the at least one person is doing at the location; when the at least one person is at the location; how the at least one person got to the location and/or plans to leave the location; and an environmental condition at the location.

In exemplary embodiments, the context(s) associated with the behavior(s) of the at least one person includes at least three or more of: where is the at least one person; why is the at least one person exhibiting the behavior(s); who (if anyone) is virtually and/or actually with the at least one person or nearby the at least one person within audible, visual, and/or electronic detection range of the devices, sensors, and/or communication network(s); what is the at least one person doing; when is the at least one person exhibiting the behavior(s); how is the at least one person exhibiting the behavior(s); and an environmental condition.

In exemplary embodiments, the plurality of devices, sensors, and communication network(s) comprises at least two different types of devices, sensors, and communication network(s) configured to take a plurality of different types of measurements/readings.

In exemplary embodiments, the system is configured to automatically determine, through the plurality of measurements/readings automatically taken by the plurality of devices, sensors, and communications network(s), the behavior(s) of the at least one person and (a) the context(s) associated with the behavior(s) of the at least one person; or (b) the location and the context(s) associated with the behavior(s) of the at least one person, without requiring the at least one person to manually take the plurality of measurements/readings using the plurality of devices, sensors, and communications network(s). The system is also configured to automatically analyze the measurements/readings, the behavior(s) of the at least one person, and (a) the context(s) associated with the behavior(s) of the at least one person or (b) the location and the context(s) associated with the behavior(s) of the at least one person at the location, to thereby determine the risk of the addiction-related or restriction violation-related behavior(s) of the at least one person relative to the trigger threshold(s), without requiring the at least one person to manually predict the risk of the addiction-related or restriction violation-related behavior(s).

In exemplary embodiments, the system is configured to determine the context(s) associated with the behavior(s) of the at least one person including why the at least one person is exhibiting the behavior(s) based on at least one or more of: where is the at least one person; who (if anyone) is virtually and/or actually with the at least one person or nearby the at least one person within audible, visual, and/or electronic detection range of the devices, sensors, and/or communication network(s); what is the at least one person doing; when is the at least one person exhibiting the behavior(s); how is the at least one person exhibiting the behavior(s); and at least one environmental condition.

Exemplary embodiments of the present disclosure can be implemented in numerous ways, including (without limitation) as method(s)/process(es), apparatus(es), system(s), composition(s) of matter, computer readable media, such as non-transitory computer readable storage media, and/or computer network(s) wherein program instructions may be sent, e.g., over optical, electronic, wireline, cloud-based, drone-based, Internet, wireless, peer-to-peer, machine-to-machine, and/or other communications link(s) and combination(s). At least some such implementations may be referred to, e.g., as techniques and/or mechanisms. In general, the order of the steps of disclosed processes may be altered within the scope of the present disclosure.

Exemplary embodiments may include one or more computing devices, such as one or more servers, workstations, personal computers, laptops, tablets, smartphones, person digital assistants (PDAs), etc. In addition, the computing device may include a single computing device, or it may include multiple computing devices located in close proximity or distributed over a geographic region, so long as the computing devices are specifically configured to function as described herein. Further, different components and/or arrangements of components than illustrated herein may be used in the computing device and/or in other computing device embodiments.

Exemplary embodiments may include one or more processors and memory coupled to (and in communication with) the one or more processors. A processor may include one or more processing units (e.g., in a multi-core configuration, etc.) such as, and without limitation, a central processing unit (CPU), a microcontroller, a reduced instruction set computer (RISC) processor, an application specific integrated circuit (ASIC), a programmable logic device (PLD), a gate array, and/or any other circuit or processor capable of the functions described herein.

In exemplary embodiments, a memory may be one or more devices that permit data, instructions, etc., to be stored therein and retrieved therefrom. The memory may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, and/or any other type of volatile or nonvolatile physical or tangible computer-readable media.

In exemplary embodiments, computer-executable instructions may be stored in the memory for execution by a processor to particularly cause the processor to perform one or more of the functions described herein, such that the memory is a physical, tangible, and non-transitory computer readable storage media. Such instructions often improve the efficiencies and/or performance of the processor that is performing one or more of the various operations herein. It should be appreciated that the memory may include a variety of different memories, each implemented in one or more of the functions or processes described herein.

In exemplary embodiments, a network interface may be coupled to (and in communication with) the processor and the memory. The network interface may include, without limitation, a wired network adapter, a wireless network adapter, a mobile network adapter, or other device capable of communicating to one or more different networks. In some exemplary embodiments, one or more network interfaces may be incorporated into or with the processor.

It should be appreciated that the functions described herein, in some embodiments, may be described in computer executable instructions stored on a computer readable media, and executable by one or more processors. The computer readable media is a non-transitory computer readable storage medium. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or databases and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

Example embodiments are provided so that the present disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the present disclosure. In some example embodiments, well-known processes, well-known device structures, and well-known technologies are not described in detail. For example, technical material that is known in the technical fields related to the present disclosure has not been described in detail so that the present disclosure is not unnecessarily obscured. This includes, but is not limited, to technology utilized in determining the location of mobile devices via a variety of means. In addition, advantages and improvements that may be achieved with one or more exemplary embodiments of the present disclosure are provided for purposes of illustration only and do not limit the scope of the present disclosure, as exemplary embodiments disclosed herein may provide all or none of the above mentioned advantages and improvements and still fall within the scope of the present disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. In addition, as used herein, the term "or" is an inclusive "or" operator and is equivalent to the term "and/or," unless the context clearly dictates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The term "based on" is not exclusive and allows for being based on additional factors not described unless the context clearly dictates otherwise. The term "network" is used in multiple contexts within the present disclosure, and its use generally (but not necessarily) falls into one of two categories. The first is in the form of a (generally human) support "network" including one or more individuals/entities that provide the addict with some sort of support or assistance. The second is in a technical context, such as a communications network that transmits, receives, and/or otherwise provides technical connectivity between various technical components disclosed herein.

As used herein, the terms "support network" and "support community" refer to a concept that an individual's or groups of individuals' personal network of friends, family colleagues, coworkers, medical/mental health/addiction professionals, members of their social network (e.g., Facebook, Twitter, Snapchat, etc.), etc. and the subsequent connections within those networks can be utilized to find more relevant connections for a variety of activities, including, but not limited to dating, job networking, service referrals, content sharing, like-minded individuals, activity partners, or the like. Such social network may be created based on a variety of criteria, including, for example, an address book, a social event, an online community, or the like. As used herein, the term "member" refers to a user who is included in a support network. The term "group" or "community" refers to a collection of members.

Although the terms first, second, third, etc. may be used herein to describe various elements, components, or features, these elements, components, or features should not be limited by these terms. These terms may be only used to distinguish one element, component, or feature from another element, component, or feature. Terms such as "first," "second," and other numerical terms when used herein do not imply a sequence or order unless clearly indicated by the context. Thus, a first element, component, or feature could be termed a second element, component, or feature without departing from the teachings of the example embodiments.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The foregoing description of the embodiments has been provided for purposes of illustration and description. It is not intended to be exhaustive or to limit the present disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

What is claimed is:

1. A system comprising a plurality of devices, sensors, and communication network(s), the system configured to:
 determine, through a plurality of measurements/readings taken by the plurality of devices, sensors, and communication network(s), behavior(s) of at least one person and
  (a) context(s) associated with the behavior(s) of the at least one person; or
  (b) location and the context(s) associated with the behavior(s) of the at least one person;
 analyze the measurements/readings, the behavior(s) of the at least one person, and (a) the context(s) associated with the behavior(s) of the at least one person or (b) the location and the context(s) associated with the behavior(s) of the at least one person at the location, that are associated with at least one related trigger that is related to either or both of an addiction-related trigger and a restriction violation-related trigger, to thereby determine a risk of an addiction-related or restriction violation-related behavior(s) of the at least one person relative to at least one trigger threshold(s) or trend(s);
 facilitate one or more actions to lower the risk of the addiction-related or restriction violation-related behavior(s) associated with the at least one related trigger from reaching or exceeding the trigger threshold(s) associated with the addiction-related or restriction violation-related behavior(s) before the addiction-related or restriction violation-related behavior(s) occurs; and
 monitor result(s) of the one or more actions, learn effectiveness of risk lowering action(s) from the monitored result(s), and determine system modification(s), if any, related to the at least one person's likelihood or relapse and/or occurrence of the addiction-related or restriction violation-related behavior(s), the effectiveness of the risk lowering action(s), and types and frequency of the measurements/readings taken by the plurality of devices, sensors, and communication network(s);
 wherein:
  the plurality of devices, sensors, and communication network(s) are configured for monitoring noise type(s) and/or level(s), yelling, speech pattern(s), word usage, speech volume, and/or clarity of speech of the at least one person, skin and/or body temperature of the at least one person, and ambient temperature; and
  the system is configured to determine that an Anger trigger for the at least one person is active, in danger of becoming active, or imminent based on the measurements/readings of the noise type(s) and/or level(s), yelling, speech pattern(s), word usage, speech volume, and/or clarity of speech of the at least one person, the skin and/or body temperature of the at least one person, and the ambient temperature.

2. The system of claim 1, wherein the system is configured to utilize artificial intelligence or machine learning to determine system modification(s), if any, to profile parameter(s) of the at least one person, risk determination algorithm(s) and/or measurements/readings taken by the plurality of devices, sensors, and communications network(s) relative to the at least one related trigger and/or the addiction-related or restriction violation-related behavior(s) of the at least one person.

3. The system of claim 1, wherein the system is configured to determine whether any other trigger(s) related to the Anger trigger for the at least one person is active, in danger of becoming active, or imminent, including two or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

4. The system of claim 1, wherein:
 the plurality of devices, sensors, and communication network(s) are configured for monitoring proximity of the at least one person to one or more other persons; and
 the system is configured to determine that the Anger trigger for the at least one person is active, in danger of becoming active, or imminent based on the measurements/readings of the noise type(s) and/or level(s), yelling, speech pattern(s), word usage, speech volume, and/or clarity of speech of the at least one person, the skin and/or body temperature of the at least one person referenced to the ambient temperature, and proximity of the at least one person to the one or more other persons.

5. The system of claim 1, wherein the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person and a change in the skin and/or body temperature of the at least one person referenced to the ambient temperature.

6. The system of claim 1, wherein:
 the plurality of devices, sensors, and communication network(s) are configured for monitoring ambient noise level; and
 the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level and/or a change in the skin and/or in body temperature of the at least one person referenced to the ambient temperature.

7. The system of claim 1, wherein:
 the plurality of devices, sensors, and communication network(s) are configured for monitoring blood pressure of the at least one person and ambient noise level; and
 the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level, a change in the skin and/or body temperature of the at least one person referenced to the ambient temperature, and/or a change in blood pressure of the at least one person.

8. The system of claim 1, wherein the system is configured to utilize artificial intelligence or machine learning to learn from the at least one person's addiction-related and/or restriction violation-related behavior(s) and response(s) to behavioral modification action(s), and to refine system parameter(s), if any, related to the at least one person's likelihood or relapse and/or occurrence of the addiction-related or restriction violation-related behavior(s), the effectiveness of the risk lowering action(s), and types and frequency of the measurements/readings taken by the plurality of devices, sensors, and communication network(s).

9. The system of claim 1, wherein the system is configured to utilize artificial intelligence or machine learning to determine:
which of the plurality of devices, sensors, and communication network(s) are used;
types and frequency of the measurements/readings taken by the plurality of devices, sensors, and communication network(s); and
which of the system's algorithm(s), digital agent(s), and engine(s) are used.

10. The system of claim 1, wherein the system includes a learning engine configured to utilize artificial intelligence or machine learning to learn from the at least one person's behavior and response(s) to behavioral modification action(s) and to refine the system's algorithm(s), and process(es) related to the at least one person's likelihood or relapse and/or occurrence of the addiction-related or restriction violation-related behavior(s), the effectiveness of the risk lowering action(s), and types and frequency of the measurements/readings taken by the plurality of devices, sensors, and communication network(s).

11. The system of claim 1, wherein the system includes a learning engine configured to utilize artificial intelligence or machine learning to analyze the measurements/readings, the behavior(s) of the at least one person, and (a) the context(s) associated with the behavior(s) of the at least one person or (b) the location and the context(s) associated with the behavior(s) of the at least one person at the location, that are associated with at least one related trigger that is related to either or both of an addiction-related trigger and a restriction violation-related trigger, to thereby determine a risk of an addiction-related or restriction violation-related behavior(s) of the at least one person relative to at least one trigger threshold(s) or trend(s).

12. The system of claim 1, wherein the system is configured to utilize a prediction algorithm(s) or a scoring formula(s) for determining a current or trending degree of risk of the addiction-related or restriction violation-related behavior(s) of the at least one person.

13. The system of claim 1, wherein the system is configured to:
determine whether (a) the context(s) associated with the behavior(s) of the at least one person corresponds to a high-risk context or (b) the location and the context(s) associated with the behavior(s) of the at least one person at the location correspond to a high-risk location and context
identify one or more of available support resource(s) and interface(s) for the at least one person to mitigate the risk of the addiction-related or restriction violation-related behavior(s) of the at least one person;
select one or more of the identified available support resource(s) and interface(s) for the at least one person; and
implement the selected available support resource(s) and interface(s) for the at least one person if the (a) context(s) associated with the behavior(s) of the at least one person or (b) the location and the context(s) associated with the behavior(s) of the at least one person at the location correspond to a trending risk of the addiction-related or restriction violation-related behavior(s) of the at least one person.

14. The system of claim 13, wherein:
the interface(s) includes at least one interface(s) configured to enable interaction between the at least one person and a support network or third party (ies); and
the support resource(s) include at least one member of the at least one person's support network including a sponsor, a family member, or a friend.

15. The system of claim 1, wherein the system is configured to determine whether any other trigger(s) related to the Anger trigger for the at least one person is active, in danger of becoming active, or imminent, including one or more of Anxiety, Boredom, Change, Conflict, Depression, Disorder, Envy, Desire to Escape, Excitement, Extreme Emotions, Fear, Frustration, Guilt, Health problems, Holidays, Hunger, Insomnia, Job issues, Kids/Children, Loneliness, Media marketing, Mid-Life Crisis, Money problems, Music, Noise, Overconfidence, Peer Pressure, Power, Powerlessness, Proximity to an Addictive Substance, Fear of Quitting, Relationships, Relatives, Reminders, Sex, Change of Seasons, Smell, Social Situations, Stress, Taste, Times of Day, Being Tired, Feeling Not Fun, Unhappy, Feeling Victimized, Weather, Yelling, and Zeal.

16. The system of claim 1, wherein the system is configured to utilize artificial intelligence or machine learning to learn from the at least one person's behavior and response(s) to behavioral modification action(s) and modify the system including modifications related to encouragement or avoidance of (a) the context(s) associated with the behavior(s) of the at least one person or (b) the location and the context(s) associated with the behavior(s) of the at least one person at the location, who and/or what support resource(s) and interface(s) are utilized and when.

17. The system of claim 1, wherein the system is configured to utilize artificial intelligence or machine learning to learn from the at least one person's behavior and response(s) to behavioral modification action(s) and modify the system including modifications to the types and frequency of the measurements/readings taken by the plurality of devices, sensors, and communication network(s) relating to:
noise types, levels monitored, frequency of monitoring of noise types and levels, changes to yelling, speech patterns, word usage, speech, yelling volume and speech clarity, changes in the skin and/or body temperature of the at least one person; and
type(s), level(s), threshold(s), trend(s) parameter(s) and frequency of monitoring by the plurality of devices, sensors, and communication network(s).

18. The system of claim 1, wherein the system is configured to utilize artificial intelligence or machine learning to learn from the at least one person's behavior and response(s) to behavioral modification action(s) and modify the system including modifications to the usage(s), value(s), threshold(s), range(s), trend(s) parameter(s), and weight(s) of the types and frequency of the measurements/readings taken by the plurality of devices, sensors, and communication network(s) that are utilized in trigger risk prediction algorithm(s) of the system.

19. The system of claim 1, wherein the system is configured such that in response to detection of the Anger trigger and an unsuccessful call to a first family member of the at least one person to alleviate the Anger trigger, the system is configured to use artificial intelligence or machine learning to determine a second family member to call in an attempt to alleviate the Anger trigger of the at least one person.

20. A system comprising a plurality of devices, sensors, and communication network(s), the system configured to:
   determine, through a plurality of measurements/readings taken by the plurality of devices, sensors, and communication network(s), behavior(s) of at least one person and
      (a) context(s) associated with the behavior(s) of the at least one person; or
      (b) location and the context(s) associated with the behavior(s) of the at least one person;
   analyze the measurements/readings, the behavior(s) of the at least one person, and (a) the context(s) associated with the behavior(s) of the at least one person or (b) the location and the context(s) associated with the behavior(s) of the at least one person at the location, that are associated with at least one related trigger that is related to either or both of an addiction-related trigger and a restriction violation-related trigger, to thereby determine a risk of an addiction-related or restriction violation-related behavior(s) of the at least one person relative to at least one trigger threshold(s) or trend(s);
   facilitate one or more actions to lower the risk of the addiction-related or restriction violation-related behavior(s) associated with the at least one related trigger from reaching or exceeding the trigger threshold(s) associated with the addiction-related or restriction violation-related behavior(s) before the addiction-related or restriction violation-related behavior(s) occurs; and
   monitor result(s) of the one or more actions, learn effectiveness of risk lowering action(s) from the monitored result(s), and determine system modification(s), if any, related to the at least one person's likelihood or relapse and/or occurrence of the addiction-related or restriction violation-related behavior(s), the effectiveness of the risk lowering action(s), and types and frequency of the measurements/readings taken by the plurality of devices, sensors, and communication network(s);
   wherein:
      the plurality of devices, sensors, and communication network(s) are configured for monitoring skin and/or body temperature of the at least one person and ambient temperature; and
      the system is configured to determine that an Anger trigger for the at least one person is active, in danger of becoming active, or imminent based on the measurements/readings of a change in the skin and/or body temperature of the at least one person referenced to the ambient temperature.

21. The system of claim 20, wherein the system is configured to utilize artificial intelligence or machine learning to determine system modification(s), if any, to profile parameter(s) of the at least one person, risk determination algorithm(s) and/or measurements/readings taken by the plurality of devices, sensors, and communications network(s) relative to the at least one related trigger and/or the addiction-related or restriction violation-related behavior(s) of the at least one person.

22. The system of claim 20, wherein the system is configured to determine whether any other trigger(s) related to the Anger trigger for the at least one person is active, in danger of becoming active, or imminent, including two or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

23. The system of claim 20, wherein:
   the plurality of devices, sensors, and communication network(s) are configured for monitoring ambient noise level; and
   the system is configured to determine that the Anger trigger for the at least one person is active, in danger of becoming active, or imminent based on the measurements/readings of a change in the skin and/or body temperature of the at least one person referenced to the ambient temperature and a change in the noise type(s) and/or level(s), yelling, speech pattern(s), word usage, speech volume, and/or clarity of speech of the at least one person referenced to the ambient noise level.

24. The system of claim 20, wherein:
   the plurality of devices, sensors, and communication network(s) are configured for monitoring proximity of the at least one person to one or more other persons; and
   the system is configured to determine that the Anger trigger for the at least one person is active, in danger of becoming active, or imminent based on the measurements/readings of a change in the skin and/or body temperature of the at least one person referenced to the ambient temperature and proximity of the at least one person to the one or more other persons.

25. The system of claim 20, wherein:
   the plurality of devices, sensors, and communication network(s) are configured for monitoring blood pressure of the at least one person; and
   the system is configured to determine that the Anger trigger for the at least one person is active, in danger of becoming active, or imminent based on the measurements/readings of a change in the skin and/or body temperature of the at least one person referenced to the ambient temperature and a change in blood pressure of the at least one person.

26. A system comprising a plurality of devices, sensors, and communication network(s), the system configured to:
   determine, through a plurality of measurements/readings taken by the plurality of devices, sensors, and communication network(s), behavior(s) of at least one person and
      (a) context(s) associated with the behavior(s) of the at least one person; or
      (b) location and the context(s) associated with the behavior(s) of the at least one person;
   analyze the measurements/readings, the behavior(s) of the at least one person, and (a) the context(s) associated with the behavior(s) of the at least one person or (b) the location and the context(s) associated with the behavior(s) of the at least one person at the location, that are associated with at least one related trigger that is related to either or both of an addiction-related trigger and a restriction violation-related trigger, to thereby determine a risk of an addiction-related or restriction violation-related behavior(s) of the at least one person relative to at least one trigger threshold(s) or trend(s);
   facilitate one or more actions to lower the risk of the addiction-related or restriction violation-related behavior(s) associated with the at least one related trigger from reaching or exceeding the trigger threshold(s) associated with the addiction-related or restriction violation-related behavior(s) before the addiction-related or restriction violation-related behavior(s) occurs; and
   monitor result(s) of the one or more actions, learn effectiveness of risk lowering action(s) from the monitored result(s), and determine system modification(s), if any, related to the at least one person's likelihood or relapse and/or occurrence of the addiction-related or restriction violation-related behavior(s), the effectiveness of the risk lowering action(s), and types and frequency of the measurements/readings taken by the plurality of devices, sensors, and communication network(s); wherein:
  the plurality of devices, sensors, and communication network(s) are configured for monitoring noise type(s) and/or level(s), yelling, speech pattern(s), word usage, speech volume, and/or clarity of speech of the at least one person and ambient noise level; and
  the system is configured to determine that an Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level.

27. The system of claim 26, wherein the system is configured to utilize artificial intelligence or machine learning to determine system modification(s), if any, to profile parameter(s) of the at least one person, risk determination algorithm(s) and/or measurements/readings taken by the plurality of devices, sensors, and communications network(s) relative to the at least one related trigger and/or the addiction-related or restriction violation-related behavior(s) of the at least one person.

28. The system of claim 26, wherein the system is configured to determine whether any other trigger(s) related to the Anger trigger for the at least one person is active, in danger of becoming active, or imminent, including two or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

29. The system of claim 26, wherein:
  the plurality of devices, sensors, and communication network(s) are configured for monitoring skin and/or body temperature of the at least one person and ambient temperature; and
  the system is configured to determine that an Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level and a change in the skin and/or body temperature of the at least one person referenced to the ambient temperature.

30. The system of claim 26, wherein:
  the plurality of devices, sensors, and communication network(s) are configured for monitoring proximity of the at least one person to one or more other persons; and
  the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level and proximity of the at least one person to the one or more other persons.

31. The system of claim 26, wherein:
  the plurality of devices, sensors, and communication network(s) are configured for monitoring blood pressure of the at least one person; and
  the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level and a change in blood pressure of the at least one person.

32. A system comprising a plurality of devices, sensors, and communication network(s) configured for monitoring noise type(s) and/or level(s), yelling, speech pattern(s), word usage, speech volume, and/or clarity of speech of at least one person, skin and/or body temperature of the at least one person, and ambient temperature, wherein the system is configured to determine, through a plurality of measurements/readings taken by the plurality of devices, sensors, and communication network(s), that an Anger trigger for the at least one person is active, in danger of becoming active, or imminent based on the measurements/readings of the noise type(s) and/or level(s), yelling, speech pattern(s), word usage, speech volume, and/or clarity of speech of the at least one person, the skin and/or body temperature of the at least one person, and the ambient temperature, and wherein the system is further configured to:
  facilitate one or more actions to lower the risk of the Anger trigger from reaching or exceeding an Anger trigger threshold(s); and
  monitor result(s) of the one or more actions, learn effectiveness of risk lowering action(s) from the monitored result(s), and determine system modification(s), if any, related to the at least one person's likelihood or relapse and/or occurrence of an undesirable behavior(s), the effectiveness of the risk lowering action(s), and types and frequency of the measurements/readings taken by the plurality of devices, sensors, and communication network(s).

33. The system of claim 32, wherein the system is configured to determine, through the plurality of measurements/readings taken by the plurality of devices, sensors, and communication network(s), behavior(s) of at least one person and
  (a) context(s) associated with the behavior(s) of the at least one person; or
  (b) location and the context(s) associated with the behavior(s) of the at least one person.

34. The system of claim 33, wherein the system is configured to analyze the measurements/readings, the behavior(s) of the at least one person, and (a) the context(s) associated with the behavior(s) of the at least one person or (b) the location and the context(s) associated with the behavior(s) of the at least one person at the location, that are associated with at least one related trigger that is related to the Anger trigger, to thereby determine a risk of the undesirable behavior of the at least one person relative to at least one trigger threshold(s) or trend(s).

35. The system of claim 34, wherein the system is configured to facilitate one or more actions to lower the risk of the undesirable behavior(s) associated with the at least one related trigger a trigger(s) from reaching or exceeding the trigger threshold(s) associated with the undesirable behavior(s) before the undesirable behavior(s) occurs.

36. The system of claim 35, wherein the system is configured to utilize artificial intelligence or machine learning to determine system modification(s), if any, to profile parameter(s) of the at least one person, risk determination algorithm(s) and/or measurements/readings taken by the plurality of devices, sensors, and communications network(s) relative to the at least one related trigger and/or the undesirable behavior(s) of the at least one person.

37. The system of claim 32, wherein the system is configured to determine whether any other trigger(s) related to the Anger trigger for the at least one person is active, in danger of becoming active, or imminent, including two or more of a Frustration trigger, a Job trigger, a Personal Relationship trigger, a Stress trigger, a Despair trigger, a Self-Loathing trigger, a Resentment trigger, an Information Overload/Snowball Effect trigger, and/or a Yelling trigger.

38. The system of claim 32, wherein:
the plurality of devices, sensors, and communication network(s) are configured for monitoring proximity of the at least one person to one or more other persons; and
the system is configured to determine that the Anger trigger for the at least one person is active, in danger of becoming active, or imminent based on the measurements/readings of the noise type(s) and/or level(s), yelling, speech pattern(s), word usage, speech volume, and/or clarity of speech of the at least one person, the skin and/or body temperature of the at least one person referenced to the ambient temperature, and proximity of the at least one person to the one or more other persons.

39. The system of claim 32, wherein the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person and a change in the skin and/or body temperature of the at least one person referenced to the ambient temperature.

40. The system of claim 32, wherein:
the plurality of devices, sensors, and communication network(s) are configured for monitoring ambient noise level; and
the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level and/or a change in the skin and/or in body temperature of the at least one person referenced to the ambient temperature.

41. The system of claim 32, wherein:
the plurality of devices, sensors, and communication network(s) are configured for monitoring blood pressure of the at least one person and ambient noise level; and
the system is configured to determine that the Anger trigger for the at least one person is active, in danger of becoming active, or imminent based on the measurements/readings of a change in the noise type(s) and/or level(s), yelling, speech pattern(s), word usage, speech volume, and/or clarity of speech of the at least one person referenced to the ambient noise level, a change in the skin and/or body temperature of the at least one person referenced to the ambient temperature, and/or a change in blood pressure of the at least one person.

* * * * *